(12) United States Patent
Muthukumar et al.

(10) Patent No.: US 11,782,055 B2
(45) Date of Patent: Oct. 10, 2023

(54) MULTI-CONFIGURABLE SENSING ARRAY AND METHODS OF USING SAME

(71) Applicants: EnLiSense, LLC, Allen, TX (US); Board of Regents, The University of Texas System, Austin, TX (US)

(72) Inventors: Sriram Muthukumar, Allen, TX (US); Shalini Prasad, Allen, TX (US)

(73) Assignees: EnLiSense, LLC, Allen, TX (US); Board of Regents, The University of Texas System, Austin, TX (US)

( * ) Notice: Subject to any disclaimer, the term of this patent is extended or adjusted under 35 U.S.C. 154(b) by 175 days.

(21) Appl. No.: 16/343,747

(22) PCT Filed: Oct. 19, 2017

(86) PCT No.: PCT/US2017/057478
§ 371 (c)(1),
(2) Date: Apr. 19, 2019

(87) PCT Pub. No.: WO2018/075824
PCT Pub. Date: Apr. 26, 2018

(65) Prior Publication Data
US 2019/0250153 A1    Aug. 15, 2019

Related U.S. Application Data

(60) Provisional application No. 62/410,598, filed on Oct. 20, 2016.

(51) Int. Cl.
*G01N 33/543* (2006.01)
*G01N 33/58* (2006.01)
(Continued)

(52) U.S. Cl.
CPC .............. *G01N 33/543* (2013.01); *C12Q 1/68* (2013.01); *G01N 33/5438* (2013.01);
(Continued)

(58) Field of Classification Search
CPC ........... G01N 33/543; G01N 33/54333; G01N 33/551
See application file for complete search history.

(56) References Cited

U.S. PATENT DOCUMENTS 8,623,196 B2   1/2014   Kohli et al.
8,758,584 B2   6/2014   Kahn et al.
(Continued)

FOREIGN PATENT DOCUMENTS

WO    2006052891 A1    5/2006
WO    WO-2012050646 A2 *  4/2012    ........... G01N 33/554
(Continued)

OTHER PUBLICATIONS

CN103675075 machine translation (Year: 2014).*
(Continued)

*Primary Examiner* — Caitlyn Mingyun Sun
(74) *Attorney, Agent, or Firm* — Akona IP

(57) ABSTRACT

Disclosed herein are devices, apparatus, systems, methods and kits for performing immunoassay tests on a sample. The A sensing apparatus is provided for detecting a plurality of different target analytes in a sample. The apparatus may comprise an array of sensing devices provided on a substrate, each sensing device in the array comprising a working electrode having (1) semiconducting nanostructures disposed thereon and (2) a capture reagent coupled to the semiconducting nanostructures that selectively binds to a different target analyte in the sample. The apparatus may also comprise sensing circuitry that (1) simultaneously detects changes to electron and ion mobility and charge accumulation in the array of sensing devices when the capture reagents in the array of sensing devices selectively bind to the plurality of different target analytes, and (2) determines the presence and concentrations of the plurality of different target analytes in the sample based on the detected changes.

20 Claims, 19 Drawing Sheets

(51) Int. Cl.
    *G01N 33/551*    (2006.01)
    *C12Q 1/68*      (2018.01)

(52) U.S. Cl.
    CPC ..... *G01N 33/54333* (2013.01); *G01N 33/551* (2013.01); *G01N 33/588* (2013.01)

(56) References Cited

U.S. PATENT DOCUMENTS

| | | | |
|---|---|---|---|
| 9,064,965 | B2 | 6/2015 | Lu et al. |
| 9,846,136 | B2* | 12/2017 | Wu .................... G01N 27/3272 |
| 2002/0197390 | A1 | 12/2002 | Lewis et al. |
| 2005/0029445 | A1 | 2/2005 | Lee et al. |
| 2009/0242399 | A1* | 10/2009 | Kamath ............ A61B 5/14532 204/406 |
| 2011/0172559 | A1* | 7/2011 | Fei .................... A61B 5/14514 600/583 |
| 2012/0125789 | A1* | 5/2012 | Ocvirk ................ C12Q 1/001 977/773 |
| 2014/0011691 | A1* | 1/2014 | Sierks ................ C07K 16/005 506/18 |
| 2015/0011421 | A1* | 1/2015 | Li ........................ G01N 27/27 506/11 |
| 2016/0146754 | A1 | 5/2016 | Prasad et al. |
| 2016/0291001 | A1* | 10/2016 | Revzin .................. C08L 65/00 |

FOREIGN PATENT DOCUMENTS

| | | |
|---|---|---|
| WO | 2012050646 A3 | 10/2012 |
| WO | 2016157117 A1 | 10/2016 |

OTHER PUBLICATIONS

Definition of proximate (Year: 2022).*
M. Jacobs, Ultra-sensitive electrical immunoassay biosensors using nanotextured zinc oxide thin films on printed circuit board platforms, Biosensors and Bioelectronics, 55, 2014, p. 7-13. (Year: 2014).*
Ji, CN103675075 machine translation. (Year: 2014).*
R.D. Munje, Flexible nanoporous tunable electrical double layer biosensors for sweat diagnostics, Scientific Reports, 2015, 5:14586, p. 1-11. (Year: 2015).*
PCT International Search Report and Written Opinion in PCT International Application Serial No. PCT/US2017/057478 dated Feb. 16, 2018 (17 pages).
PCT International Preliminary Report on Patentability issued for International Patent Application No. PCT/US2017/057478, dated Apr. 23, 2019; 9 pages.

* cited by examiner

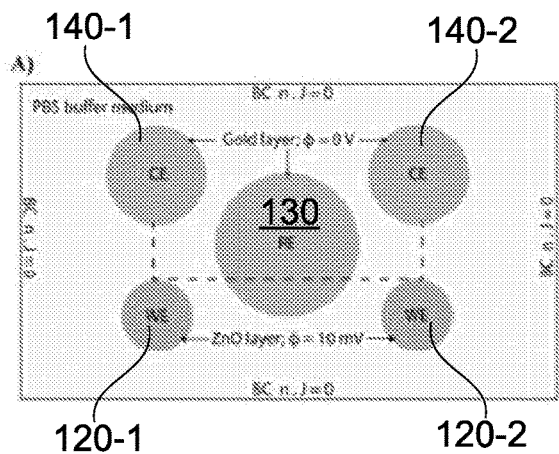
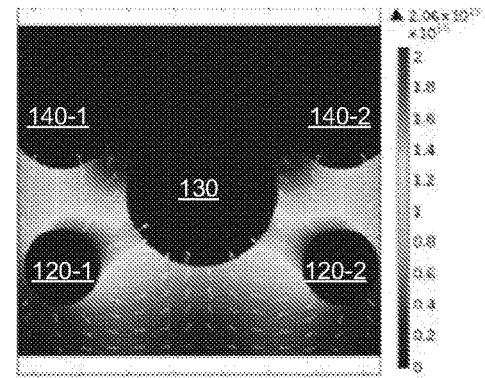
FIG. 9A
FIG. 9B
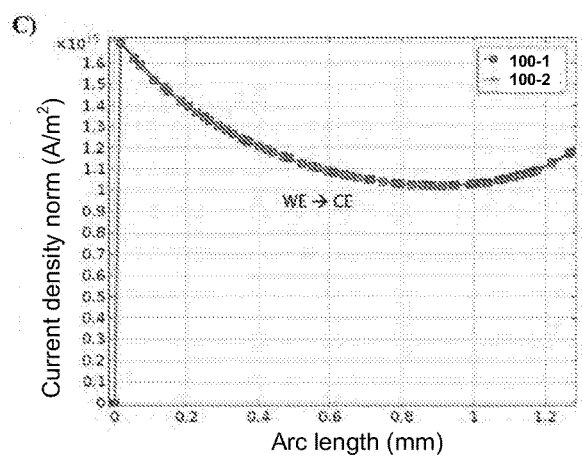
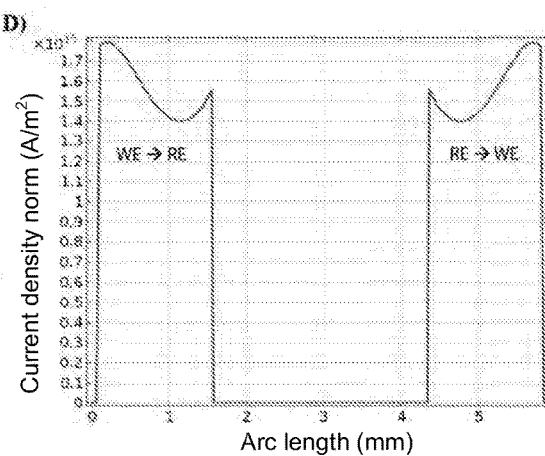
FIG. 9C
FIG. 9D

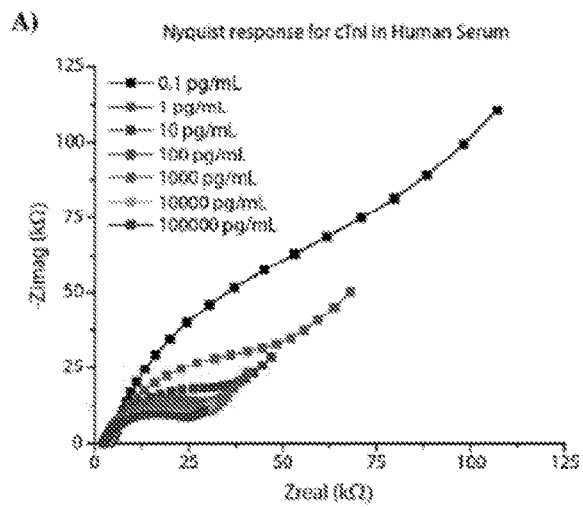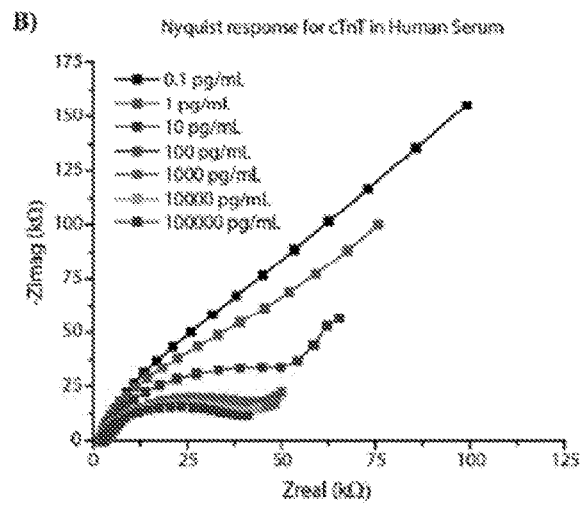
FIG. 11A  FIG. 11B
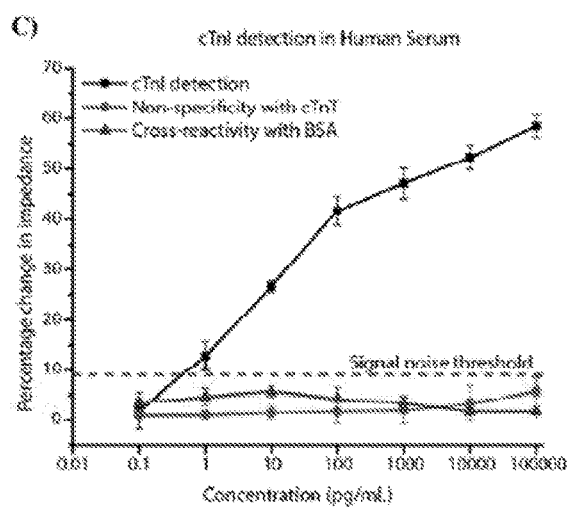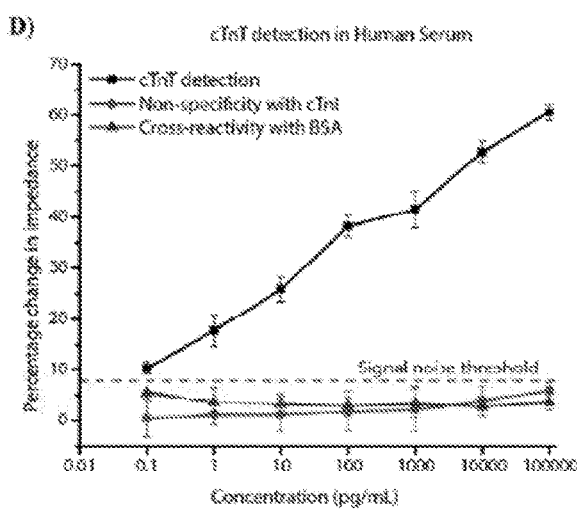
FIG. 11C  FIG. 11D

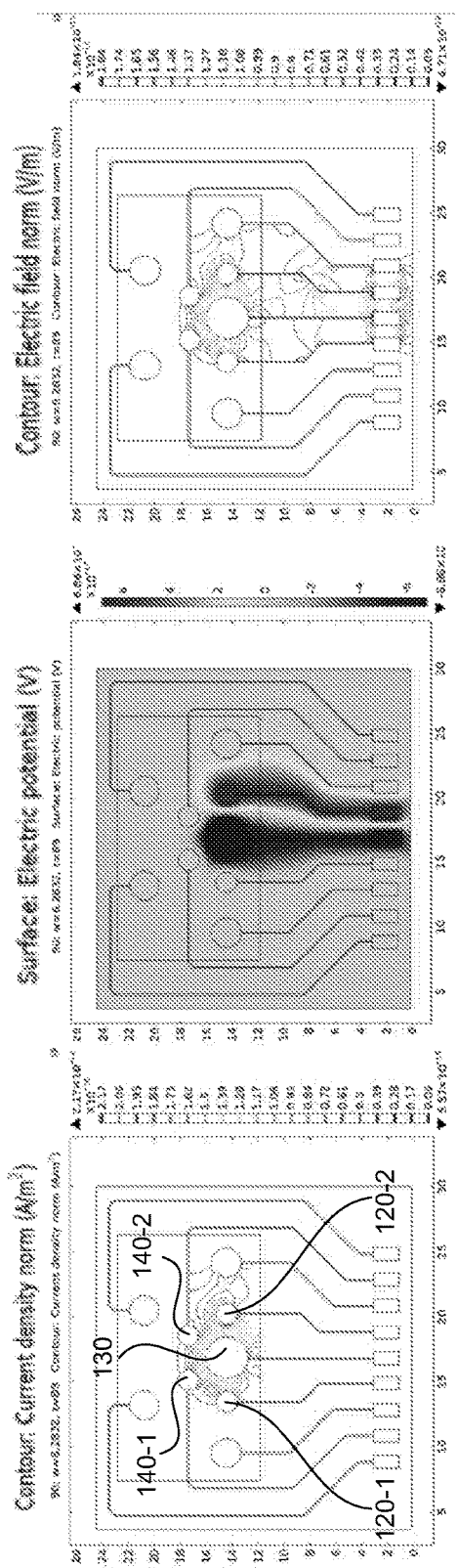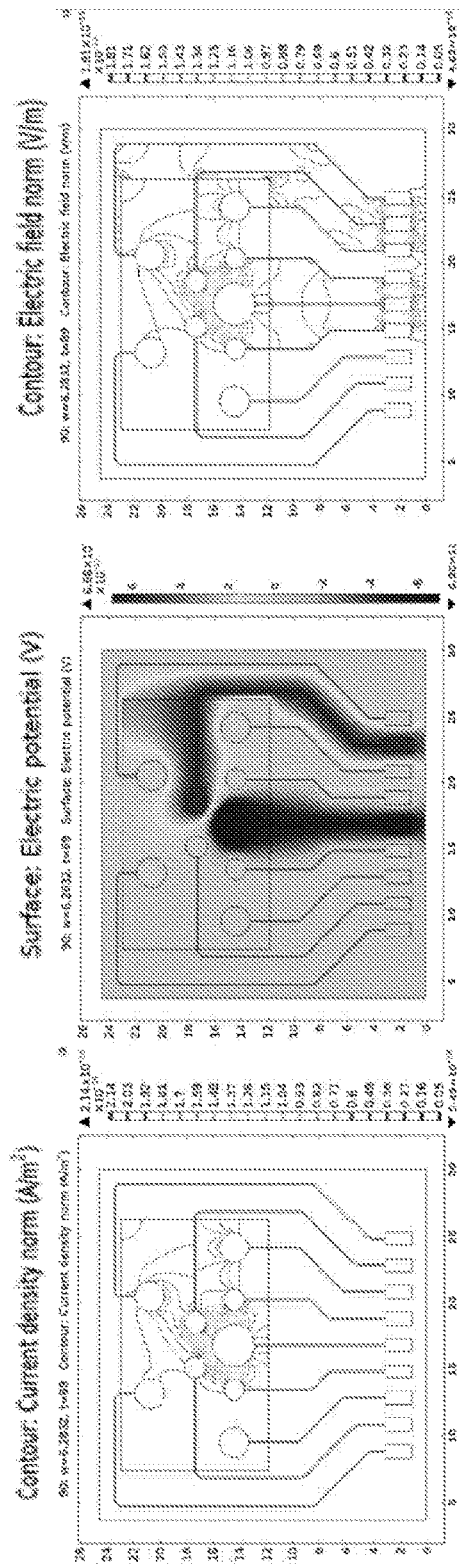
FIG. 17A   FIG. 17B   FIG. 17C
FIG. 17D   FIG. 17E   FIG. 17F

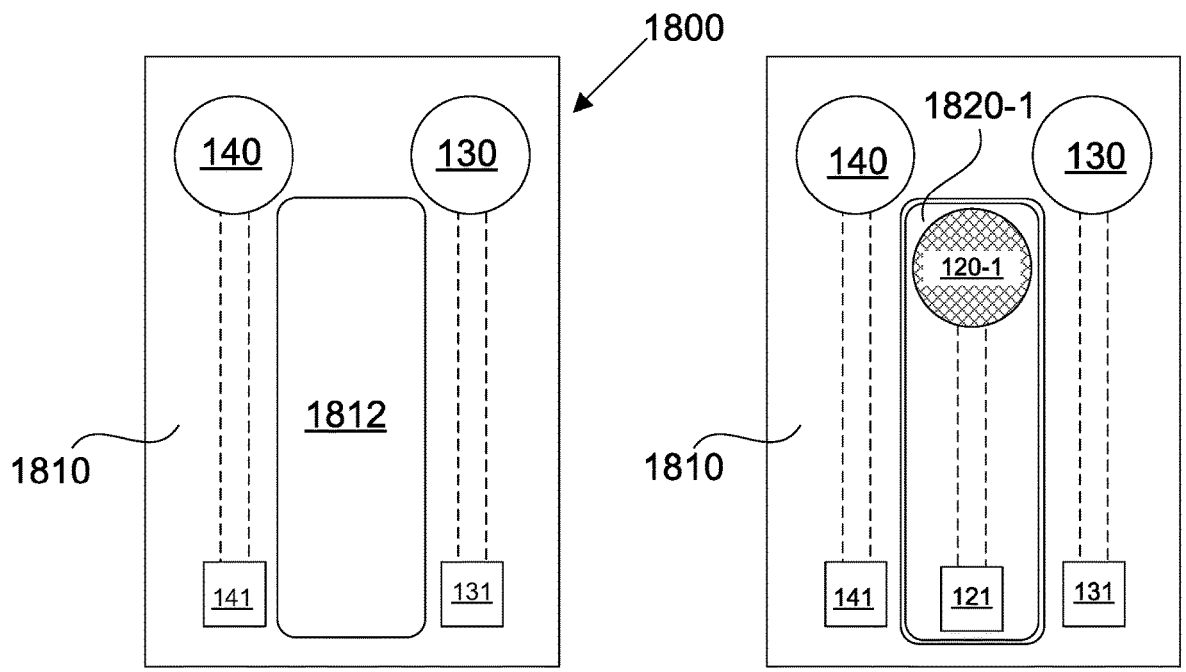
FIG. 18A
FIG. 18C
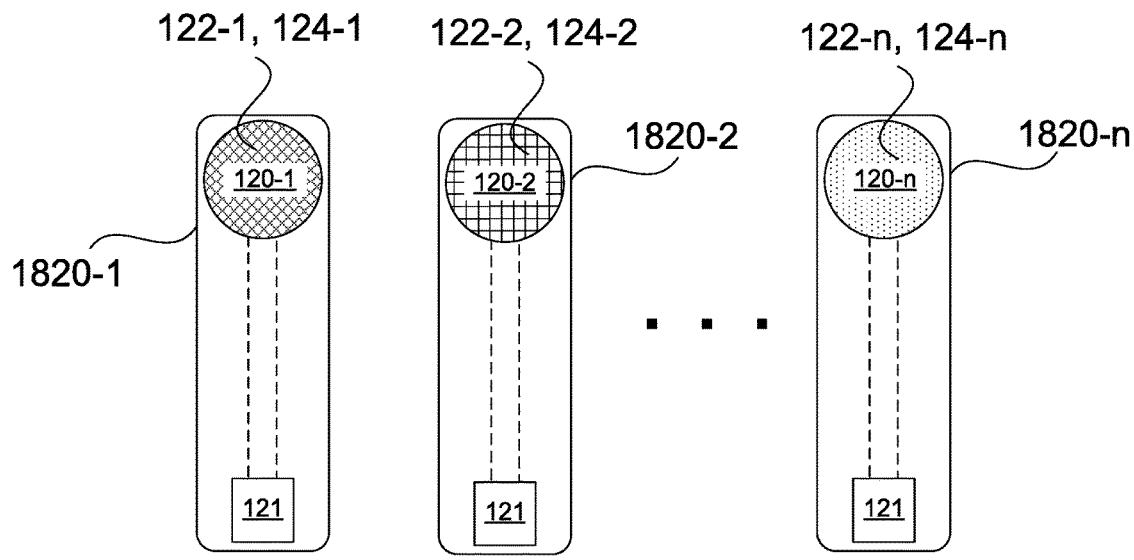
FIG. 18B

MULTI-CONFIGURABLE SENSING ARRAY AND METHODS OF USING SAME

CROSS-REFERENCE TO RELATED APPLICATION

This Application is a national stage application under 35 U.S.C. § 371 of PCT International Application Serial No. PCT/US2017/057478, filed on Oct. 19, 2017, entitled MULTI-CONFIGURABLE SENSING ARRAY AND METHODS OF USING SAME, which application claims the benefit of priority to U.S. Provisional Patent Application Ser. No. 62/410,598 filed on Oct. 20, 2016, entitled ELECTRICAL NANOBIOSENSORS. The disclosures of the prior applications are considered part of and are hereby incorporated by reference in their entirety in the disclosure of this application.

BACKGROUND

Early detection and reliable diagnosis can play a central role in making effective therapeutic decisions for treatment of diseases or managing certain physiological conditions. Detection may involve identification of disease-specific biomarkers in human body fluids that indicate irregularities in cellular regulatory functions, pathological responses, or intervention to therapeutic drugs.

Immunoassays can provide rapid and cost-effective mechanisms for detecting the presence and concentrations of analytes in a sample. Oftentimes, a single analyte (e.g. biomarker) or molecule may not be sufficient for unambiguous identification of specific diseases or for treating complex pathology conditions. In many cases, it is desirable to simultaneously detect the presence and concentration of more than one analyte in a sample, for example a variety of different analytes. More sensitive methods and devices for performing such tests are needed, that can enable users to perform quantitative measurements with higher accuracy and wider dynamic range than currently available biosensing devices.

Wearable sensors that monitor disease-specific biomarkers can be used for maintaining stasis in humans and their surrounding environments. Common modalities for biological/chemical sensing may utilize affinity-based reactions and binding mechanisms to transduce optical, electrical, and/or mechanical signals. There is a need for wearable and non-invasive (or minimally invasive) sensing technologies that allow users to accurately and rapidly evaluate their physiological status in a continuous manner. Ideally, such analysis and quantification may be performed in real-time in order to provide prompt feedback to the users.

SUMMARY

The present disclosure addresses at least some of the above needs. Various embodiments of the present disclosure address the demand for wearable and non-invasive sensors that are capable of quantifying multiple different types of target agents (chemical, biological, etc.) simultaneously and in real-time. The sensing devices and methods described herein can enable detection of (i) a wide range of chemical agents and/or (ii) a wide range of biomarkers (analytes) that provide indicators about a person's physiological state, for detecting diseases and also for monitoring the health conditions of the user/wearer. In some embodiments, microelectrode affinity-based electrical sensing platforms for point-of-care (POC) detection of disease-specific biomarkers can provide quantitative, multiplexed, and simultaneous detection of multiple biomarkers for rapid diagnostic and prognostic analysis on a single test sample that is introduced onto the sensing platform. Point-of-care, rapid quantification of protein biomolecules (that are specific biomarkers of certain diseases) can help in various aspects of disease diagnosis, monitoring, and analysis. The multiplexed and simultaneous detection of multiple biomarkers on a common sensing platform obviates the need to have multiple discrete immunoassay strips for detecting different biomarkers, and may also eliminate the need to collect multiple samples for testing.

In some embodiments, the multi-biomarker sensing devices and methods described herein can weigh individual biomarkers differentially on the basis of the end physiological state being predicted. In some embodiments, highly specific biomarkers can be detected rapidly at ultralow concentrations from very low fluid sample volumes from a user. Disease specific protein biomarker detection can be achieved having (1) ultra-sensitivity in reliable detection at low concentrations (typically in lower pg/ml), and (2) specificity in protein detection from complex solutions such as body fluids.

According to some aspects of the disclosure, a sensing apparatus for detecting a plurality of different target analytes in a sample is provided. The apparatus may comprise an array of sensing devices provided on a substrate. Each sensing device in the array may comprise a working electrode having (1) semiconducting nanostructures disposed thereon and (2) a capture reagent coupled to the semiconducting nanostructures that selectively binds to a different target analyte in the sample. The apparatus may also comprise sensing circuitry that (1) simultaneously detects changes to electron and ion mobility and charge accumulation in the array of sensing devices when the capture reagents in the array of sensing devices selectively bind to the plurality of different target analytes, and (2) determines the presence and concentrations of the plurality of different target analytes in the sample based on the detected changes.

Also disclosed is a method of detecting a plurality of different target analytes in a sample. The method may comprise: providing the sensing apparatus described herein; applying the sample to the array of sensing devices; and with aid of the sensing circuitry, simultaneously detecting the changes to the electron and ion mobility and charge accumulation in the array of sensing devices by simultaneously measuring (1) impedance changes using a modified Electrochemical Impedance Spectroscopy (EIS) technique and (2) capacitance changes using a Mott-Schottky technique; and determining the presence and concentrations of the plurality of different target analytes by concurrently analyzing the measured impedance and capacitance changes.

In some embodiments, a sensing system may comprise: a test strip comprising the array of sensing devices, and a point-of-care (POC) portable health diagnostics reader comprising the aforementioned sensing circuitry, wherein the diagnostics reader comprises an opening for receiving the test strip.

In some embodiments, a wearable device may comprise the aforementioned sensing apparatus and may be configured to be worn on a portion of a user's body.

In another aspect, a non-transitory computer readable medium storing instructions that, when executed by one or more processors, causes the one or more processors to perform a computer-implemented method for detecting a plurality of different target analytes in a sample is provided. The method may comprise: collecting electrical signals from an array of sensing devices provided on a substrate, each sensing device in the array comprising a working electrode having (1) semiconducting nanostructures disposed thereon and (2) a capture reagent coupled to the semiconducting nanostructures that selectively binds to a different target analyte; simultaneously detecting changes to electron and ion mobility and charge accumulation from the collected electrical signals when the capture reagents in the array of sensing devices selectively bind to the different target analytes in the sample; and determining the presence and concentrations of the plurality of different target analytes in the sample based on the detected changes.

Further aspects of the disclosure are directed to a modular sensing kit for detecting a plurality of different target analytes in a sample. The kit may comprise: a base module comprising at least one reference electrode and at least one counter electrode disposed on a substrate; and a plurality of discrete sensors configured to be interchangeably and releasably coupled to the base module, each of the plurality of discrete sensors comprising a working electrode having (1) semiconducting nanostructures disposed thereon and (2) a capture reagent coupled to the semiconducting nanostructures that selectively binds to a different target analyte in the sample.

In some embodiments, the working electrodes of the plurality of discrete sensors may have the same type or different types of semiconducting nanostructures. Each of the plurality of discrete sensors can be configured to be mechanically and electrically coupled to the base module. Each of the plurality of discrete sensors is usable for determining a presence and concentration of a different target analyte in the sample. In some cases, the base module may comprise at least one receiving portion on the substrate for coupling to a discrete sensor. Additionally, the base module may comprise a plurality of receiving portions on the substrate for coupling to a plurality of discrete sensors.

A module sensing device may comprise the base module, and a discrete sensor that is selected from the plurality of discrete sensors and coupled to the base module. A modular sensing apparatus may comprise the base module, and two or more discrete sensors that are selected from the plurality of discrete sensors and coupled to the base module, to thereby provide an array of sensing devices. In some embodiments, at least two sensing devices from the array may utilize a common reference electrode. The common reference electrode may be located between the working electrodes of the at least two sensing devices. The modular sensing apparatus may further comprise sensing circuitry that (1) simultaneously detects changes to electron and ion mobility and charge accumulation in the array of sensing devices when the capture reagents in the array of sensing devices selectively bind to the plurality of different target analytes, and (2) determines the presence and concentrations of the plurality of different target analytes in the sample based on the detected changes.

A method of detecting a target analyte in a sample may comprise: providing the modular sensing kit; forming the modular sensing device by coupling the selected discrete sensor to the base module; applying the sample to the modular sensing device; and with aid of sensing circuitry, detecting changes to electron and ion mobility and charge accumulation in the modular sensing device by measuring (1) impedance changes using a modified Electrochemical Impedance Spectroscopy (EIS) technique and (2) capacitance changes using a Mott-Schottky technique; and determining a presence and concentration of a target analyte by analyzing the measured impedance and capacitance changes.

A method of detecting a plurality of target analytes in a sample may comprise: providing the modular sensing kit; forming the modular sensing apparatus by coupling the selected two or more discrete sensors to the base module; applying the sample to the array of sensing devices; and with aid of the sensing circuitry, simultaneously detecting the changes to the electron and ion mobility and charge accumulation in the array of sensing devices by simultaneously measuring (1) impedance changes using a modified Electrochemical Impedance Spectroscopy (EIS) technique and (2) capacitance changes using a Mott-Schottky technique; and determining the presence and concentrations of the plurality of different target analytes by concurrently analyzing the measured impedance and capacitance changes.

In some embodiments, a sensing system may comprise: a test strip comprising the modular sensing apparatus; and a point-of-care (POC) portable health diagnostics reader comprising the sensing circuitry, wherein the diagnostics reader comprises an opening for receiving the test strip. In some embodiments, a wearable device may comprise the modular sensing apparatus and may be configured to be worn on a portion of a user's body.

According to some aspects of the disclosure, a sensing device for detecting one or more target analytes in a fluid sample is provided. The device may comprise a substrate comprising two or more electrodes, a plurality of semiconducting nanostructures disposed on at least one of the electrodes, and a plurality of capture reagents attached to the plurality of semiconducting nanostructures. The plurality of capture reagents are configured to selectively bind to the one or more target analytes in the fluid sample, thereby effecting changes to electron and ion mobility and charge accumulation in different regions of the semiconducting nanostructures and the fluid sample. The changes to the electron and ion mobility and charge accumulation can be detected with aid of sensing circuitry, and used to determine a presence and concentration of the one or more target analytes in the fluid sample. The changes may comprise simultaneous modulation to the ion mobility in one or more regions adjacent or proximal to the semiconducting nanostructures.

In some embodiments, the changes to the electron and ion mobility and charge accumulation can be transduced into electrical impedance and capacitance signals. The signals may be indicative of interfacial charge modulation comprising of the changes to the electron and ion mobility. The signals may be indicative of capacitance changes to a space-charge region formed in the semiconducting nanostructures upon binding of the one or more target analytes to the capture reagents. The sensing circuitry can be configured to implement a plurality of electrochemical detection techniques for detecting the capacitance changes and impedance changes. The plurality of electrochemical detection techniques may include (1) a modified Electrochemical Impedance Spectroscopy (EIS) technique for measuring the impedance changes and (2) Mott-Schottky technique for measuring the capacitance changes. The sensing device is capable of simultaneous and multiplexed detection of a plurality of target analytes present in the fluid sample using the plurality of electrochemical detection techniques. In some instances, the sensing device comprises the sensing circuitry, and the sensing circuitry can be configured to perform the simultaneous and multiplexed detection by analyzing the electrical impedance and capacitance signals to determine the presence and concentration of each of the plurality of target analytes. The sensing circuitry can be configured to perform the simultaneous and multiplexed detection substantially in real-time upon binding of the plurality of target analytes to the capture reagents on the semiconducting nanostructures.

In some embodiments, the sensing circuitry can be configured to analyze the electrical impedance and capacitance signals by concurrently analyzing a set of Nyquist plots obtained via the modified EIS technique and a set of Mott-Schottky plots obtained via the Mott-Schottky technique. The modified EIS technique may comprise (1) sectioning an interfacial charge layer into a plurality of spatial dielectric z-planes along a direction orthogonal to the interface between the fluid sample and the semiconducting nanostructures, and (2) probing each of the plurality of z-planes with a specific frequency selected from a range of frequencies. Specific binding of different target analytes to the capture reagents occurs at known spatial heights within the interfacial charge layer, and the sensing circuitry can be configured to determine the presence and concentration of each of the different target analytes by measuring the capacitance and impedance changes at specific frequencies corresponding to their respective z-planes at the known spatial heights within the interfacial charge layer. The modified EIS technique is capable of distinguishing the electrical impedance signals from background noise at low concentrations of the target analytes in the fluid sample.

In some embodiments, the sensing device may be provided on a single electrochemical test strip. The sensing device may not require multiple discrete electrochemical test strips for performing the simultaneous and multiplexed detection of the plurality of target analytes.

In some embodiments, the plurality of semiconducting nanostructures may comprise surfaces that are functionalized with a linking reagent, and the capture reagents may be immobilized onto the surfaces of the semiconducting nanostructures via the linking reagent.

In some embodiments, the plurality of semiconducting nanostructures may be thermally grown on said electrode(s) in a configuration that aids in radial diffusion of the fluid sample around the plurality of semiconducting nanostructures. The plurality of semiconducting nanostructures may comprise, for example ZnO nanostructures.

The fluid sample may be selected from the group consisting of sweat, blood, serum, and urine of a human subject. In some cases, the fluid sample may further include a room temperature ionic liquid (RTIL) electrolyte buffer. The sensing device is capable of determining the presence and concentration of the one or more target analytes in a volume of the fluid sample equal to or less than 30 μL. In some embodiments, the substrate may comprise a flexible and porous polyimide substrate having low absorption of the fluid sample. The sensing device is capable of determining the presence and concentration of the one or more target analytes, without the use of any visual markers or labels conjugated to the capture reagents.

In some embodiments, the plurality of semiconducting nanostructures may be disposed on two or more electrodes comprising a first electrode and a second electrode. A first capture reagent may be attached to the semiconducting nanostructures on the first electrode and configured to selectively bind to a first target analyte. A second capture reagent may be attached to the semiconducting nanostructures on the second electrode and configured to selectively bind to a second target analyte. In some embodiments, the first and second target analytes may comprise different isoforms of a same type of biomarker. The sensing device is capable of simultaneously determining the presence and concentrations of the first and second target analytes upon binding of the target analytes to the respective capture reagents. The sensing device can be configured for both catalytic and affinity-based detection of the one or more target analytes. In some embodiments, the one or more target analytes may comprise a plurality of cardiac biomarkers, and the plurality of capture reagents may comprise a plurality of antibodies that are specific to the plurality of cardiac biomarkers.

According to another aspect, a method of detecting one or more target analytes in a fluid sample is provided. The method may include providing a sensing device comprising (1) a substrate comprising two or more electrodes, (2) a plurality of semiconducting nanostructures disposed on at least one of said electrodes, and (3) a plurality of capture reagents attached to the plurality of semiconducting nanostructures. The method may also include applying the fluid sample containing the one or more target samples to the sensing device. The method may further include detecting, with aid of sensing circuitry, changes to electron and ion mobility and charge accumulation in different regions of the semiconducting nanostructures and the fluid sample when the plurality of capture reagents selectively bind to the one or more target analytes in the fluid sample; and determining a presence and concentration of the one or more target analytes based on the detected changes to the electron and ion mobility and charge accumulation.

A further aspect of the present disclosure is directed to a sensing array for detecting a plurality of different target analytes in a fluid sample. The array may comprise two or more sensing devices disposed on a common substrate. The sensing devices may each comprise a working electrode having a plurality of semiconducting nanostructures disposed thereon and a capture reagent attached to the semiconducting nanostructures. The fluid sample may be applied to the electrodes of the two or more sensing devices. The two or more sensing devices may comprise different capture reagents that are configured to selectively bind to the different target analytes in the fluid sample. The selective binding is configured to effect changes to electron and ion mobility and charge accumulation in different regions of the semiconducting nanostructures and the fluid sample. Each of the sensing devices can be configured to determine a presence and concentration of a different target analyte in the fluid sample based on detected changes to the electron and ion mobility and charge accumulation. The changes can comprise simultaneous modulation to the ion mobility in one or more regions adjacent to the semiconducting nanostructures.

In some embodiments, the working electrodes of the two or more sensing devices may have different types of semiconducting nanostructures disposed thereon. In some cases, different types of capture reagents may be attached to the different types of semiconducting nanostructures.

In some embodiments, at least two of the sensing devices may share a common reference electrode. Each of the at least two sensing devices may further comprise a counter electrode. The common reference electrode may be disposed between the working electrodes of the at least two sensing devices. Additionally or optionally, the common reference electrode may be disposed between the counter electrodes of the at least two sensing devices.

In some embodiments, a first sensing device may comprise a working electrode, a counter electrode and a reference electrode located in proximity to each other in a first region of the substrate. A second sensing device may comprise a working electrode, a counter electrode and a reference electrode located in proximity to each other in a second region of the substrate. The first sensing device may comprise a first capture reagent configured to selectively bind to a first target analyte, and the second sensing device may comprise a second capture reagent configured to selectively bind to a second target analyte. In some embodiments, the first and second target analytes may be different isoforms of a same type of biomarker.

In some embodiments, the electrodes of the two or more sensing devices may be connected to sensing circuitry configured for simultaneous acquisition and multiplexing of electrical signals from the two or more sensing devices. The sensing circuitry can be configured to analyze the electrical signals comprising of impedance and capacitance signals. The signals may be indicative of interfacial charge modulation comprising of the changes to the electron and ion mobility. The signals may include capacitance changes to space-charge regions formed in the semiconducting nanostructures upon binding of the different target analytes to the corresponding capture reagents.

In some embodiments, the sensing circuitry can be configured to implement a plurality of electrochemical detection techniques for detecting the impedance changes and the capacitance changes. The plurality of electrochemical detection techniques may include a modified EIS technique for measuring the impedance changes and Mott-Schottky technique for measuring the capacitance changes. The sensing array is capable of simultaneous and multiplexed detection of the different target analytes present in the fluid sample using the plurality of electrochemical detection techniques. The sensing circuitry can be configured to perform the simultaneous and multiplexed detection by analyzing the electrical impedance and capacitance signals to determine the presence and concentration of each of the different target analytes. The sensing circuitry can be configured to perform the simultaneous and multiplexed detection substantially in real-time upon binding of the different target analytes to the corresponding capture reagents on the semiconducting nanostructures.

The sensing circuitry can be configured to analyze the impedance and capacitance signals by concurrently analyzing a set of Nyquist plots obtained via the modified EIS technique and a set of Mott-Schottky plots obtained via the Mott-Schottky technique. In some embodiments, the modified EIS technique may comprise (1) sectioning an interfacial charge layer for each of the two or more sensing devices into a plurality of spatial dielectric z-planes along a direction orthogonal to the interface between the fluid sample and the semiconducting nanostructures, and (2) probing each of the plurality of z-planes with a specific frequency selected from a range of frequencies. Specific binding of different target analytes to the corresponding capture reagents occurs at known spatial heights within the plurality of interfacial charge layers for the two or more sensing devices. The sensing circuitry can be configured to determine the presence and concentration of each of the different target analytes by measuring the capacitance and impedance changes at specific frequencies corresponding to their respective z-planes. The modified EIS technique is capable of distinguishing the electrical impedance signals from background noise at low concentrations of the different target analytes in the fluid sample.

In some embodiments, the sensing array may be provided as a single electrochemical test strip. The sensing array may not require multiple discrete electrochemical test strips for performing the simultaneous and multiplexed detection of the different target analytes.

In some embodiments, the sensing circuitry can be configured to selectively apply a plurality of modulation signals to the two or more sensing devices to enable detection of the plurality of different target analytes in the fluid sample. The sensing circuitry can be configured to individually and selectively control, activate, or modulate the two or more sensing devices. The plurality of modulation signals can be configured to aid in enhancing detection sensitivity of the different target analytes.

A method of detecting a plurality of different target analytes in a fluid sample is provided in accordance with another aspect. The method may include providing the sensing array disclosed herein; applying the fluid sample containing the one or more target samples to the sensing array; and using each of the sensing devices to determine the presence and concentration of a different target analyte in the fluid sample, based on the detected changes to the electron and ion mobility and charge accumulation in the different regions of the semiconducting nanostructures and the fluid sample.

A further aspect is directed to a sensor module for detecting one or more target analytes in a fluid sample. The sensor module may comprise a base module configured to releasably couple to one or more discrete sensors. The one or more discrete sensors can be used to determine a presence and concentration of the one or more target analytes in the fluid sample based on detected changes to electron and ion mobility and charge accumulation when the discrete sensor(s) are coupled to the base module and the fluid sample is applied to the sensor module. In some embodiments, the sensor module may further comprise the one or more discrete sensors.

The one or more discrete sensors can be configured to be mechanically and electrically coupled to the base module. Each of the one or more discrete sensors may comprise a working electrode having a plurality of semiconducting nanostructures disposed thereon and a capture reagent attached to the semiconducting nanostructures. The base module may comprise at least one reference electrode and at least one ground electrode. A plurality of discrete sensors may comprise different capture reagents that are configured to selectively bind to different target analytes in the fluid sample. The selective binding is configured to effect changes to the electron and ion mobility and charge accumulation in different regions of the semiconducting nanostructures and the fluid sample. The plurality of discrete sensors can be used for determining the presence and concentration of the different target analytes in the fluid sample.

In some embodiments, the base module may comprise (1) a first receiving portion configured to couple to a first discrete sensor, and (2) a second receiving portion configured to couple to a second discrete sensor. The first discrete sensor may comprise a first working electrode, and the second discrete sensor may comprise a second working electrode. A first sensing device can be formed by coupling the first discrete sensor to the first receiving portion. The first sensing device may comprise the first working electrode, a first counter electrode, and a reference electrode. A second sensing device can be formed by coupling the second discrete sensor to the second receiving portion. The second sensing device may comprise the second working electrode, a second counter electrode, and a reference electrode. In some embodiments, the first sensing device and the second sensing device may share the same reference electrode. The first sensing device can be configured to determine the presence and concentration of a first target analyte, and the second sensing device can be configured to determine the presence and concentration of a second target analyte.

In some embodiments, a method of using the sensor module for detecting one or more target analytes in a fluid sample may include: providing the base module that is configured to releasably couple to one or more discrete sensors; coupling the one or more discrete sensors to the base module thereby electrically and mechanically connecting said discrete sensor(s) to the base module; applying the fluid sample to the sensor module; and using the one or more discrete sensors to determine a presence and concentration of the one or more target analytes in the fluid sample based on detected changes to electron and ion mobility and charge accumulation that are specific to each of the one or more target analytes.

In some embodiments, a method of using the sensor module for detecting one or more target analytes in a fluid sample may include: providing the base module that is configured to releasably couple to one or more discrete sensors; coupling a first discrete sensor to the base module thereby electrically and mechanically connecting the first discrete sensor to the base module; applying the fluid sample to the sensor module comprising the first discrete sensor; and using the first discrete sensor to determine a presence and concentration of a first target analyte in the fluid sample based on detected changes to electron and ion mobility and charge accumulation that are specific to the first target analyte. The method may also comprise detaching the first discrete sensor from the base module after the presence and concentration of the first target analyte has been determined. The method may further comprise coupling a second discrete sensor to the base module thereby electrically and mechanically connecting the second discrete sensor to the base module; applying the fluid sample to the sensor module comprising the second discrete sensor; and using the second discrete sensor to determine a presence and concentration of a second target analyte in the fluid sample based on detected changes to the electron and ion mobility and charge accumulation that are specific to the second target analyte.

In some embodiments, a method of using the sensor module for detecting two or more target analytes in a fluid sample may include: providing the base module that is configured to releasably couple to two or more discrete sensors; coupling a first discrete sensor and a second discrete sensor to the base module thereby electrically and mechanically connecting the first and second discrete sensors to the base module; applying the fluid sample to the sensor module comprising the first and second discrete sensors; and (1) using the first discrete sensor to determine a presence and concentration of a first target analyte in the fluid sample based on detected changes to electron and ion mobility and charge accumulation that are specific to the first target analyte, and (2) using the second discrete sensor to determine a presence and concentration of a second target analyte in the fluid sample based on detected changes to the electron and ion mobility and charge accumulation that are specific to the second target analyte. The sensor module is capable of simultaneous and multiplexed detection of the first and second target analytes present in the fluid sample using a plurality of electrochemical detection techniques. The plurality of electrochemical detection techniques may comprise (1) a modified Electrochemical Impedance Spectroscopy (EIS) technique for measuring impedance changes and (2) Mott-Schottky technique for measuring capacitance changes.

In some embodiments, a kit for determining the presence and concentration of one or more target analytes in a fluid sample may include: a) a sensing device, a sensing array, and/or a sensor module as described herein; and b) instructions for using the kit. The kit may further comprise a diagnostic reader device or wearable device configured to be in operable communication with the sensing device, sensing array, and/or sensor module.

According to some aspects, a sensing apparatus or method may be capable of simultaneously detecting (1) the presence and (2) concentrations ranging from 0.1 to $10^6$ nGL with a coefficient of variation less than 10%, of a plurality of different target analytes in a single sample having a volume of less than 30 µL. The sensing apparatus or method may be capable of simultaneously detecting the presence and concentrations of the plurality of different target analytes in less than 2 minutes. The sensing apparatus or method can be implemented using a single immunoassay test strip. The sensing apparatus or method can be implemented without using a separate immunoassay test strip to detect the presence and concentration of each of the plurality of different target analytes. The sensing apparatus or method is capable of simultaneously detecting the presence and concentrations of the plurality of different target analytes without the use of any visually detectable markers or labels. The sensing apparatus or method is capable of simultaneously detecting the presence and concentrations of the plurality of different target analytes comprising of (1) different biomarkers, (2) different isoforms of a same type of biomarker, and/or (3) chemical agents. The sensing apparatus or method can be implemented in a wearable device that is worn on a portion of a user's body. Additionally or optionally, the sensing apparatus or method can be implemented in a point-of-care (POC) portable health diagnostics system. The sample may include sweat, blood, serum, or urine of a human subject. The sample may be provided with a room temperature ionic liquid (RTIL) electrolyte buffer. The sensing apparatus or method is capable of simultaneously detecting the presence and concentrations of the plurality of different target analytes using catalytic and affinity-based sensing mechanisms.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 9A-9D show electrical simulation results for the sensing array of FIG. 5;

FIGS. 11A-11D show Nyquist plots and calibration curves representing the detection of cTnI and cTnT using the sensing array of FIG. 5;

FIGS. 17A-17F show different electrical field simulations for a multi-configurable sensing array comprising a plurality of electrodes; and FIGS. 18A-C show a modular sensing device in accordance with some embodiments.

DETAILED DESCRIPTION

Figure 1:
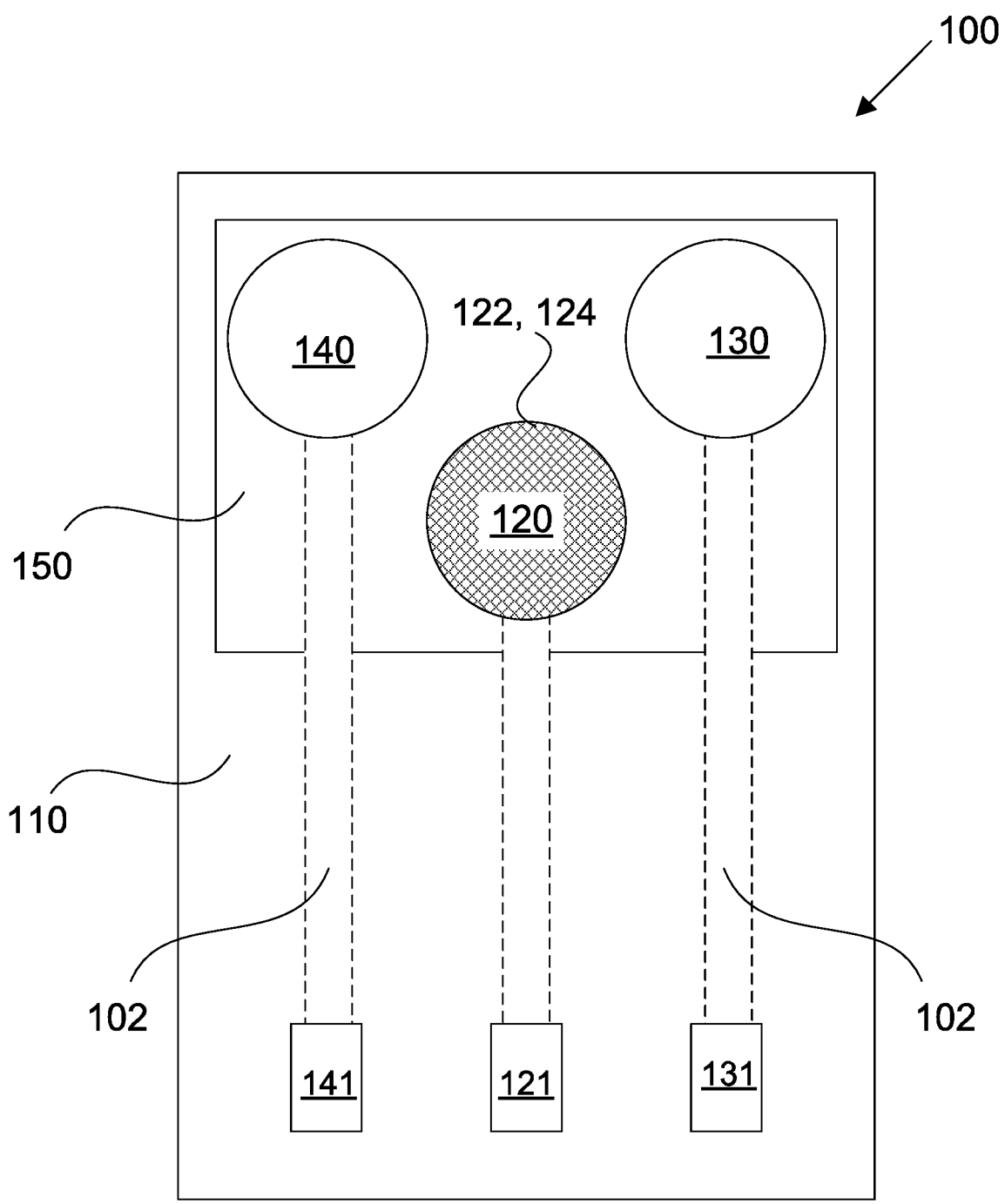
FIG. 1 shows a schematic of a sensing device in accordance with some embodiments.

Reference will now be made in detail to exemplary embodiments of the disclosure, examples of which are illustrated in the accompanying drawings. Wherever possible, the same reference numbers will be used throughout the drawings and disclosure to refer to the same or like parts.

The following is an overview of the contents in this disclosure:

I. General
II. Sensing Device
A. Substrate
B. Electrodes
C. Semiconducting Nanostructures
D. Capture Reagents
E. Test Zone
F. Sample and Target Analytes
G. Sensing Mechanisms
H. Room-Temperature Ionic Liquids (RTIL)
III. Multi-configurable Sensing Array
A. Simultaneous and Multiplexed Detection of Multiple Target Analytes
B. Electrode Configurations
IV. Sensing System
A. Multiplexer and Sensing Circuitry
B. Modified EIS
C. Simulation and Design
D. Baseline Characterization
E. Electrochemical Signal Responses
V. Sensing Platforms
A. Diagnostics Reader Device
B. Wearable Device
VI. Modular Sensing Device/Array
VII. Kits Provided herein are sensing devices, arrays of devices, and methods of using the same. Also provided herein are systems and devices configured to receive and analyze signals from the sensing devices or arrays, and provide an output based on the sensing results. Further provided herein are kits comprising modular sensing devices and arrays.

The various embodiments described herein may be useful for performing immunoassay tests on a sample, for example, to diagnose a disease or to provide information regarding a biological state or condition of a subject. The disclosed devices, arrays, systems, methods, and kits may be useful for detecting the presence and concentration of a wide variety of analytes in a sample. In many cases, the disclosed embodiments can enable simultaneous and multiplexed detection of the presence and concentration of multiple analytes in a single sample, via a common sensing platform. The various embodiments described herein are capable of detecting the presence and concentration of more than one analyte in a sample with greater specificity and/or sensitivity than currently available sensing devices or immunoassays. In many cases, the devices, arrays, systems, methods, and kits provided herein can enable a user to perform quantitative measurements with higher accuracy and wider dynamic range than currently available sensing devices or immunoassays.

As used in the specification and claims, the singular form "a", "an" and "the" include plural references unless the context clearly dictates otherwise. For example, the term "a cell" includes a plurality of cells, including mixtures thereof.

As used in the specification and claims, the term "apparatus" may include a device, an array of devices, a system, and any embodiments of the sensing applications described herein.

As used herein, the term "about" a number refers to that number plus or minus 10% of that number. The term "about" a range refers to that range minus 10% of its lowest value and plus 10% of its greatest value.

I. General

Presently, there is a need for multiplexed immunoassays that can be used for simultaneous detection of multiple analytes in a short period of time, from a small sample volume, and at reduced costs. A key challenge lies in quantitative detection of biomarkers in a simultaneous or multiplexed manner at the early stages of a disease, especially if the sample contains very low concentrations of the biomarkers. To address this challenge, accuracy in diagnosis of the disease can be enhanced by quantification through a panel of biomarkers indicative or associated with the disease. Accordingly, there is interest and value in designing ultrasensitive sensing devices that are capable of detection of a panel of biomarkers from a single sample of human body fluids.

A number of transduction mechanisms can be used to achieve ultra-sensitive and multiplexed label-free biomarker detection. An example of such transduction mechanisms may include electrical/electrochemical-based sensing platforms, which typically involve capturing biomarkers on the surface of electrode materials. This phenomenon transduces the biological signal into a measurable electrical signal response, which can then be used to detect the presence and concentration of the biomarker in the sample. The structural and morphological characteristics of the electrode materials play an important role in achieving both sensitivity and selectivity required for ultrasensitive biomarker detection. Precise control over size and shape of the materials on a nanoscale level can yield nanostructures with enhanced chemical and physical properties, that can be tailored towards the design of robust ultrasensitive sensing platforms. For example, the availability of a large number of surface atoms in extended (out-of-plane) nanostructures can allow amplification of a biological signal response, when compared to their planar sensing electrode counterparts, thereby enabling improved sensing characteristics.

Detection of analytes can be based upon enzymatic sensing devices for the detection of glucose, cholesterol, lactic acid, uric acid, etc. Quantification of such analytes may be based upon detection of byproducts of enzymatic reactions where non-specific interactions may be an issue. Technological bottlenecks associated with non-specific interactions can be minimized by use of specific capture probes. For example, affinity-based sensing mechanisms for designing immunoassay-based sensing devices using non-faradic approaches can be used. In some cases, semiconducting nanostructures can be used to facilitate direct electron transport as their electrical properties are strongly altered by charge perturbations occurring due to biomolecular confinement and binding events. The electrical detection/sensing methods described herein can permit direct characterization of capture probe—target biomarker interaction, based on charge perturbations at the electrode/electrolyte interface.

When an electrode comprising nanostructures on its surface is exposed to an ionic solution containing biomolecules, a potential difference can be created at the electrode/electrolyte interface due to unequal distribution of charges. As a result of biomolecular binding events at the nanostructured electrode surface, redistribution of charges in the electrode and ions in the electrolyte can result in formation of a space-charge region within the nanostructures and at an electrical double layer at the electrode/electrolyte interface. Biomarker binding can be evaluated and quantified by measuring changes in electrode impedance and/or capacitance at selected frequencies. In some embodiments, changes to the space-charge capacitance and overall impedance at the electrode/electrolyte interface can be measured using both Mott-Schottky technique and a modified electrochemical impedance spectroscopy (EIS) technique which are described in detail herein. A correlation in output signal response with concentration can be determined between (and using) both detection techniques, which provide a combinatorial approach for the accurate and sensitive detection of protein biomarkers.

The electrochemical sensing devices, arrays and methods described herein can be used for detecting multiple biomarkers. The sensing devices and arrays can be designed and fabricated on various substrates. The substrates may be rigid or flexible. Examples of suitable substrates may include silicon, glass, printed circuit boards, polyurethane, polycarbonate, polyamide, polyimide, and the like. The sensing devices and arrays can be used for continuous and real-time detection, monitoring, and quantification of various chemical and biological agents in body fluids. Examples of body fluids may include blood, sweat, tears, urine, saliva, and the like. Real-time detection can be performed in a single-use or in a continuous-use manner using the sensing technology platform described herein. The challenges of multiplexed detection of specific proteins can be addressed by the present inventions, which are directed to: (1) the designs of a microelectrode sensor platform comprising an array of multi-configurable sensing device each independently functionalized for specific detection of a target biomarker(s), and (2) each sensor output/results being independently measured and transduced to provide a combinatorial outcome relating to the end physiological state being predicted.

An important aspect in affinity-based sensing devices relates to the specificity of the sensor. The term "specificity" may be described as the ability of the sensor to respond specifically to target biomolecules, but not to other similar biomolecules. Generally, current electrical-based label-free sensing devices are often unable to distinguish between specific and nonspecific interactions except via probe specificity, regardless of the readout method. Specificity is often important for detection of biomolecules in real-world samples such as blood, serum, urine, saliva, sweat, etc., where the target concentration can be much lower than the concentration of non-target biomolecules present in the samples. For instance, blood serum typically contains around 70 mg/mL total protein content; however, disease biomarker proteins may be expressed in concentrations in the lower pg/mL regime. Thus, a sensing device that can detect 1 pg/mL of the protein in a saline solution but manifests a 1 ng/mL response in blood, may not be useful in a clinical setting unless the serum is depleted of interfering plasma proteins, or if some other compensations were made.

In the various embodiments described herein, specificity to the detection of target biomarkers, within each sensor on the platform array, can be achieved through specific antibody immobilization on microelectrode surfaces having semiconducting nanostructures (e.g. ZnO), functionalized using thiol-based and/or phosphonic-based linker chemistries to achieve stable and robust immobilization of the proteins. Target protein specific monoclonal antibodies can be introduced onto the linker functionalized nanostructured ZnO surfaces in the presence of a room temperature ionic liquid (RTIL) electrolyte buffer. The properties of the RTIL can be adjusted to ensure long term stability (prevent denaturing of the protein antibody from pH, temperature and environment), and enhance the efficacy in selective binding to the nanostructured ZnO surfaces. A modified electrochemical impedance spectroscopy (EIS) technique as described herein can be used for enabling ultra-sensitive and highly-specific detection of proteins.

Examples of biosensing systems and methods are described in U.S. Patent Application Publication No. 2016/146754; U.S. Provisional Application Nos. 62/554,841 and 62/554,956; non-patent literature "Ultrasensitive and low-volume point-of-care diagnostics on flexible strips—a study with cardiac troponin biomarkers," Nandhinee Radha Shanmugam, Sriram Muthukumar, and Shalini Prasad, *Nature, Scientific Reports* 6, Article Number 33423, (2016); and "A wearable biochemical sensor for monitoring alcohol consumption lifestyle through Ethyl glucuronide (EtG) detection in human sweat," Anjan Panneer Selvam, Sriram Muthukumar, Vikramshankar Kamakoti, and Shalini Prasad, *Nature, Scientific Reports* 6, Article number: 23111 (2016), the entire contents of which are herein incorporated by reference.

II. Sensing Device

Disclosed herein is a sensing device for detecting one or more target analytes in a fluid sample. The sensing device may include a substrate comprising two or more electrodes. A plurality of semiconducting nanostructures may be disposed on at least one of the electrodes. A plurality of capture reagents may be attached to the plurality of semiconducting nanostructures. The plurality of capture reagents are configured to selectively bind to the one or more target analytes in the fluid sample, thereby effecting changes to electron and ion mobility and charge accumulation in different regions of the semiconducting nanostructures and the fluid sample. The changes to the electron and ion mobility and charge accumulation are detectable with aid of sensing circuitry, and can be used to determine a presence and concentration of the one or more target analytes in the fluid sample.

Embodiments of the present disclosure are also directed to a method of detecting one or more target analytes in a fluid sample. The method may include providing a sensing device comprising (1) a substrate comprising two or more electrodes, (2) a plurality of semiconducting nanostructures disposed on at least one of said electrodes, and (3) a plurality of capture reagents attached to the plurality of semiconducting nanostructures. The method may include applying the fluid sample containing the one or more target samples to the sensing device. Additionally, the method may include detecting, with aid of sensing circuitry, changes to electron and ion mobility and charge accumulation in different regions of the semiconducting nanostructures and the fluid sample when the plurality of capture reagents selectively bind to the one or more target analytes in the fluid sample. The method may further include determining a presence and concentration of the one or more target analytes based on the detected changes to the electron and ion mobility and charge accumulation.

FIG. 1 shows a schematic of a sensing device 100 in accordance with some embodiments. The sensing device 100 may be used to conduct one or more immunoassays for detecting one or more target analytes in a sample. The sensing device may contain a plurality of capture reagents for conducting the one or more immunoassays. The capture reagents may be disposed or immobilized on a surface of at least one electrode of the sensing device. Generally, the sensing device comprises materials suitable for performing biosensing, by providing appropriate materials for immobilizing or otherwise providing various capture reagents to perform the immunoassay.

A. Substrate

Referring to FIG. 1, the sensing device 100 may comprise a substrate 110. The substrate may be flexible or rigid. The substrate may include materials such as polyimide, silicon, glass, printed circuit boards (PCB), polyurethane, polycarbonate, polyamide, or the like. In some embodiments, the substrate may be an organic substrate comprising flexible PCB materials. In some embodiments, the substrate may be a flexible and porous polyimide substrate that allows very low volumes of fluid adsorption within its pores, which in turn facilitates more effective conjugation and thus improved sensitivity in the detection of one or more target analytes present in the fluid sample. In some embodiments, the substrate may be capable of flexing or bending a large number of cycles without substantially impacting the accuracy and sensitivity of the sensing device.

In some embodiments, the substrate may comprise test strips for aiding lateral transport of a sample fluid to electrodes on the sensing device. Non-limiting examples of test strips may include porous paper, or a membrane polymer such as nitrocellulose, polyvinylidene fluoride, nylon, Fusion 5™, or polyethersulfone.

In some embodiments, the sensing device may be provided on a single electrochemical test strip. For example, the sensing device need not include multiple electrochemical test strips for performing the simultaneous and multiplexed detection of a plurality of target analytes.

B. Electrodes

The sensing device 100 may comprise two or more electrodes disposed on the substrate. For example, in the embodiment shown in FIG. 1, a working electrode (WE) 120, a reference electrode (RE) 130, and a counter electrode (CE) 140 may be disposed on the substrate 110. Any number or type of electrodes may be contemplated. The electrodes may be exposed to a sample suspected to contain one or more target analytes. A working electrode (WE) as described anywhere herein may be referred to interchangeably as a sensing electrode, a sensing working electrode, detection electrode, or the like. The WE 120 may comprise a conducting electrode stack. The WE 120 may further comprise a semiconducting sensing element (e.g., a plurality of semiconducting nanostructures 122) formed on its surface, as described in detail elsewhere herein. The RE 130 and CE 140 may each comprise a conducting electrode stack, and need not comprise sensing elements on their surfaces. For example, the RE 130 and CE 140 need not include molecules that are used for functionalizing the sensing element on the WE 120. The CE 140 and RE 130 may be electrochemically inert/stable, and may collectively form an electrochemical cell with the WE 120 when the electrodes come into contact with the fluid sample (electrolyte or ionic liquid).

The electrodes may be formed of various shapes and/or sizes. The electrodes may have a substantially circular or oval shape, for example as shown in FIG. 1. In some embodiments, the electrodes may have a regular shape (e.g. polygonal shapes such as triangular, pentagonal, hexagonal, etc.) or an irregular shape. The electrodes may be of the same size or different sizes. The electrodes may have the surface areas or different surface areas. The ratio of the surface areas of WE:CE:RE may be given by x:y:z, where x, y and z may be any integer. In some instances, z may be larger than x and y, such that the RE 130 has a larger surface area than each of WE 120 and CE 140. For example, the ratio of the surface areas of WE:CE:RE may be 1:1:2, 1:1:3, 1:1:4, 1:1:5, 1:1:6, or any other ratio. In some preferred embodiments, the ratio of the surface areas of WE:CE:RE may be 1:1:4, but is not limited thereto.

The electrodes on the sensing device 100 may be electrically connected to a plurality of contact pads via conducting layer traces 102 embedded or formed on the substrate. Each electrode may be connected to a contact pad. For example, the working electrode 120 may be connected to a first contact pad 121, the reference electrode 130 may be connected to a second contact pad 131, and the counter electrode 140 may be connected to a third contact pad 141. In some alternative embodiments, two or more electrodes may be connected to a contact pad. Optionally, an electrode may be connected to two or more contact pads. The contact pads may be located at a distance from the electrodes. In some embodiments, the contact pads and electrodes may be located at opposite ends of the substrate. The contact pads may be provided on a same surface of the substrate 110 as the electrodes. Alternatively, the contact pads may be provided on a different surface of the substrate 110 as the electrodes. For example, the contact pads and the electrodes may be provided on opposite surfaces of the substrate.

The conducting layer traces 102 may be formed of a metal, e.g. Cu. The electrodes 120, 130, and 140 may include a surface finish formed on the conducting layer traces. Non-limiting examples of surface finishes may include electroless nickel deposited on a copper trace, or an immersion gold/immersion silver/electrolytic gold deposited on an electroless nickel surface.

In some embodiments, different surface finishes on a flexible printed circuit board substrate may comprise the following exemplary thickness ranges: (1) For Immersion Silver, 8-15 micro-inches of 99% pure silver over Cu trace layer with good surface planarity, which may be a preferred surface finish for RE 130. In some cases, the post immersion silver surface finish may be chemically modified to form an Ag/AgCl surface that offers excellent electrochemical stability. (2) For Electroless Nickel Immersion Gold (ENIG), 2-8 micro-inches Au layer over 120-240 micro-inches electroless Ni layer over Cu trace layer. (3) For Electroless Nickel Electroless Palladium Immersion Gold (ENEPIG), 2-8 micro-inches Au layer over 4-20 micro-inches electroless Pd layer over 120-240 micro-inches electroless Ni layer. The Pd layer can eliminate corrosion potential from immersion reaction. Au surfaces are relatively stable/inert, offer wide electrochemical window and can be used for the WE 120 and CE 140. It should be appreciated that the above thickness values are merely exemplary, and that different thickness values may be contemplated for different surface finishes depending on the desired electrical and sensing properties.

C. Semiconducting Nanostructures

Semiconducting nanostructures may be disposed on at least one of the electrodes to aid in sensing of one or more target analytes. For example, a sensing element comprising a layer of semiconducting nanostructures 122 may be deposited over the surface of the WE 120. The WE 120 may include one or more of the surface finishes described herein. The choice of semiconducting nanostructures 122 may be determined based on the catalytic properties of the semiconducting material. In some embodiments, metal oxide nanostructured surfaces can offer immobilization when selectively functionalized with thiol and phosphonic acid linker chemistries to form specific interactions with the protein biomolecules, that can lead to enhancements in specific output signal response and enhanced specificity in biomarker detection.

Non-limiting examples of semiconducting materials that can be used on a working electrode may include the following: Diamond, Silicon, Germanium, Gray tin (α-Sn), Sulfur (α-S), Gray selenium, Tellurium, Silicon carbide (3C—SiC), Silicon carbide (4H—SiC), Silicon carbide (6H—SiC), Boron nitride (cubic), Boron nitride (hexagonal), Boron nitride (nanotube), Boron phosphide, Boron arsenide, Aluminium nitride, Aluminium phosphide, Aluminium arsenide, Aluminium antimonide, Gallium nitride, Gallium phosphide, Gallium, arsenide, Gallium antimonide, Indium nitride, Indium, phosphide, Indium arsenide, Indium antimonide, Cadmium selenide, Cadmium, sulfide, Cadmium telluride, Zinc oxide, Zinc selenide, Zinc sulfide, Zinc telluride, Cuprous, chloride, Copper sulfide, Lead selenide, Lead(II) sulfide, Lead telluride, Tin sulfide, Tin sulfide, Tin telluride, Bismuth, telluride, Cadmium phosphide, Cadmium arsenide, Cadmium antimonide, Zinc phosphide, Zinc arsenide, Zinc antimonide, Titanium dioxide (anatase), Titanium dioxide (rutile), Titanium dioxide (brookite), Copper (I) oxide, Copper(II) oxide, Uranium, dioxide, Uranium, trioxide, Bismuth, trioxide, Tin dioxide, Lead(II) iodide, Molybdenum disulfide, Gallium, selenide, Tin sulfide, Bismuth sulfide, Iron(II) oxide, Nickel(II) oxide, Europium(II) oxide, Europium(II) sulfide, Chromium(III) bromide, Arsenic sulfideOrpiment, Arsenic sulfideRealgar, Platinum, silicide, Bismuth(III) iodide, Mercury(II) iodide, Thallium(I) bromide, Silver sulfide, Iron disulfide, Lead tin, telluride, Thallium tin telluride, Thallium germanium telluride, Barium titanate, Strontium, titanate, Lithium niobate, Lanthanum copper oxide, Gallium manganese arsenide, Indium manganese arsenide, Cadmium manganese telluride, Lead manganese telluride, Copper indium selenide (CIS), Silver gallium sulfide, Zinc silicon phosphide, Copper tin sulfide (CTS), Lanthanum calcium manganite, Copper zinc tin sulfide (CZTS), or Copper zinc antimony sulfide (CZAS).

Non-limiting examples of semiconductor alloy materials that can be used on a working electrode may include the following: Silicon-germanium, Silicon-tin, Aluminium gallium arsenide, Indium gallium arsenide, Indium gallium phosphide, Aluminium indium arsenide, Aluminium indium antimonide, Gallium arsenide nitride, Gallium arsenide phosphide, Gallium arsenide antimonide, Aluminium gallium nitride, Aluminium gallium phosphide, Indium gallium nitride, Indium arsenide antimonide, Indium gallium antimonide, Cadmium zinc telluride (CZT), Mercury cadmium telluride, Mercury zinc telluride, Mercury zinc selenide, Aluminium gallium indium phosphide, Aluminium gallium arsenide phosphide, Indium gallium arsenide phosphide, Indium gallium arsenide antimonide, Indium arsenide antimonide phosphide, Aluminium indium arsenide phosphide, Aluminium gallium arsenide nitride Indium gallium arsenide nitride, Indium aluminium arsenide nitride, Gallium arsenide antimonide nitride, Copper indium gallium selenide (CIGS), Gallium indium nitride arsenide antimonide, or Gallium indium arsenide antimonide phosphide.

In some preferred embodiments, the plurality of semiconducting nanostructures 122 may comprise ZnO. ZnO is suitable for detecting biomolecules for a wide range of disease biomarkers due to its multifunctional characteristics and ability to form anisotropic nanostructures. The properties of ZnO such as good biocompatibility, wide band gap, non-toxicity, fast electron transfer, high isoelectricpoint (IEP: 9.5), favorable surface for linker chemistry binding, ease in formation of highly c-axis oriented nanostructures at low temperatures (<100° C.) and on various substrates including flexible polymeric substrates, and heightened sensitivity to adsorbed molecules render ZnO an attractive material of choice for affinity sensing applications and with both direct current (DC) and alternating current (AC) electrochemical methods. ZnO is preferred for designing sensors based on electrical transduction. Furthermore, ZnO with its single crystalline state is advantageous in the integration with flexible polymeric substrates, and offers low-cost of ownership manufacturing processes.

It is noted that any semiconducting materials with appropriate functionalization can be utilized on the working electrode(s) of the sensing device. In some embodiments, the metal oxide thin films and nanostructures of ZnO, $TiO_2$, $CNT-TiO_2$, $SnO_2$, $ZrO_2$, etc. can be used for design of glucose oxide, cholesterol oxidase and other enzymatic sensing devices. For catalytic based sensing devices, the choice of metal/semiconductor (examples: Ag, Au, Pd, Ni, Zn, Co, W, Mo, Mn, and their respective alloys such as ZnO, $TiO_2$, $MnO_2$, $MoS_2$, etc.) as the sensing electrode material may also be dependent on the electrocatalytic properties of the material and the stability of the material at the temperature of operation of the sensor, the pH range of the buffer solution containing the target analytes, and the electrochemical potential window for the detection of the target analytes.

In some embodiments, the plurality of semiconducting nanostructures 122 may be thermally grown on the working electrode in a configuration that aids in radial diffusion of the sample around the plurality of semiconducting nanostructures. As an example, the formation of ZnO nanostructures is described in detail with reference to FIGS. 6A-6C.

D. Capture Reagents

A plurality of capture reagents 124 may be attached to the plurality of semiconducting nanostructures 122 on the surface of the working electrode 120. The plurality of capture reagents are configured to selectively bind to one or more target analytes in a fluid sample, thereby effecting changes to electron and ion mobility and charge accumulation in different regions of the semiconducting nanostructures and the fluid sample. The changes to the electron and ion mobility and charge accumulation are detectable with aid of sensing circuitry, and can be used to determine a presence and concentration of the one or more target analytes in the fluid sample.

The capture reagents 124 may include an antibody or antibody fragment, an antigen, an aptamer, a peptide, a small molecule, a ligand, a molecular complex or any combination thereof. Essentially, the capture reagents may be any reagents that have specific binding activity for different target analytes. In some cases, a first capture reagent and a second capture reagent may be antibodies or antibody fragments that specifically bind to epitopes present on a first target analyte and a second target analyte, respectively. Immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. In some cases, the antibody is an antigen-binding antibody fragment such as, for example, a Fab, a F(ab'), a F(ab')2, a Fd chain, a single-chain Fv (scFv), a single-chain antibody, a disulfide-linked Fv (sdFv), a fragment comprising either a VL or VH domain, or fragments produced by a Fab expression library. Antigen-binding antibody fragments, including single-chain antibodies, can comprise the variable region(s) alone or in combination with the entirety or a portion of the following: hinge region, CH1, CH2, CH3 and CL domains. Also, antigen-binding fragments can comprise any combination of variable region(s) with a hinge region, CH1, CH2, CH3 and CL domains. Antibodies and antibody fragments may be derived from a human, rodent (e.g., mouse and rat), donkey, sheep, rabbit, goat, guinea pig, camelid, horse, or chicken. Various antibodies and antibody fragments may be designed to selectively bind essentially any desired analyte. Methods of generating antibodies and antibody fragments are well known in the art.

The terms "selective" or "specific" binding may be used herein interchangeably. Generally speaking, a ligand that selectively or specifically binds to a target means that the ligand has a high binding affinity for its target, and a low binding affinity for non-target molecules. The dissociation constant ($K_d$) may be used herein to describe the binding affinity of a ligand for a target molecule (e.g., an analyte). The dissociation constant may be defined as the molar concentration at which half of the binding sites of a target molecule are occupied by the ligand. Therefore, the smaller the $K_d$, the tighter the binding of the ligand to the target molecule. In some cases, a ligand has a dissociation constant ($K_d$) for a target molecule of less than 1 mM, less than 100 µM, less than 10 µM, less than 1 µM, less than 100 nM, less than 50 nM, less than 25 nM, less than 10 nM, less than 5 nM, less than 1 nM, less than 500 µM, less than 100 µM, less than 50 µM, or less than 5 µM.

The plurality of semiconducting nanostructures may comprise surfaces that are functionalized with a linking reagent. The capture reagents may be immobilized onto the surfaces of the semiconducting nanostructures via the linking reagent, which is described in detail with reference to FIGS. 7A-7D.

The sensing device is capable of determining the presence and concentration of one or more target analytes in a sample, without the use of any visual markers or labels conjugated to the capture reagents. In various embodiments, the capture detection reagents need not be conjugated or otherwise attached to a detectable label. A detectable label may be a fluorophore, an enzyme, a quencher, an enzyme inhibitor, a radioactive label, one member of a binding pair or any combination thereof. In contrast, other known protein sensing devices often require a label attached to the target protein for detection and quantification. Labeling a biomolecule can drastically change its binding properties, and the yield of the target-label coupling reaction can be highly variable which may affect the detection of protein targets.

The sensing device disclosed herein can circumvent the issues associated with labeling, by using label-free methods for protein detection. Many protein sensors are affinity-based which uses an immobilized capture reagent that binds a target biomolecule. The challenge of detecting a target analyte in solution lies in detecting changes at a localized surface. The use of nanomaterials (e.g. semiconducting nanostructures) as capture surfaces can be particularly beneficial when designing ultra-sensitive electrical sensing devices that rely on measured current and/or voltage to detect binding events. Electrical sensing techniques, such as the modified electrochemical impedance spectroscopy (EIS) technique described herein, have the ability to rapidly detect protein biomarkers at low concentrations. Impedance measurements can be especially useful since they do not require special labels and are therefore suitable for label-free capture operation.

E. Test Zone

Referring to FIG. 1, the substrate 110 may include a test zone 150 for receiving a sample. The test zone may correspond to a portion or region of the sensing device that is configured to receive or accept a sample. The test zone may be located anywhere on the sensing device, for example at or near an end portion of the substrate. A sample may be applied to the test zone by, e.g., inserting the end portion of the device containing the test zone into a container holding the sample, by pipetting a fluid sample directly onto the test zone, or by holding the test zone of the device under a fluid stream. Generally, the sample is a fluid sample. In other cases, the sample is a solid sample that is modified to form a fluid sample, for example, dissolved or disrupted (e.g., lysed) in a liquid medium.

In some embodiments, a test zone may optionally include a pad or other contact surface. In some cases, the pad may be composed of a woven mesh or a fibrous material such as a cellulose filter, polyesters, or glass fiber. The test zone may further include, without limitation, pH and ionic strength modifiers such as buffer salts (e.g., Tris), viscosity enhancers to modulate flow properties, blocking and resolubilization agents (e.g., proteins (such as albumin), detergents, surfactants (such as Triton X-100, Tween-20), and/or filtering agents (e.g., for whole blood)).

F. Sample and Target Analytes

Generally, the sample applied to the test zone 150 may be a fluid sample or a solid sample modified with a liquid medium. In various aspects, the sample is a biological sample. Non-limiting examples of biological samples suitable for use with the immunoassay devices of the disclosure include: whole blood, blood serum, blood plasma, urine, feces, saliva, vaginal secretions, semen, interstitial fluid, mucus, sebum, sweat, tears, crevicular fluid, aqueous humour, vitreous humour, bile, breast milk, cerebrospinal fluid, cerumen, enolymph, perilymph, gastric juice, peritoneal fluid, vomit, and the like. The biological sample can be obtained from a hospital, laboratory, clinical or medical laboratory. In some cases, the immunoassay test using the sensing device is performed by a clinician or laboratory technician. In other cases, the immunoassay test using the sensing device is performed by the subject, for example, at home.

The biological sample can be from a subject, e.g., a plant, fungi, eubacteria, archaebacteria, protist, or animal. The subject can be an organism, either a single-celled or multicellular organism. The subject can be cultured cells, which can be primary cells or cells from an established cell line, among others. Examples of cell lines include, but are not limited to, 293-T human kidney cells, A2870 human ovary cells, A431 human epithelium, B35 rat neuroblastoma cells, BHK-21 hamster kidney cells, BR293 human breast cells, CHO Chinese hamster ovary cells, CORL23 human lung cells, HeLa cells, or Jurkat cells. The sample can be isolated initially from a multi-cellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant. The female can be ovulating. In some cases, the sample is a single or individual cell from a subject and the biological sample is derived from the single or individual cell. In some cases, the sample is an individual microorganism, or a population of micro-organisms, or a mixture of micro-organisms and host cells.

In some cases, the biological sample comprises one or more bacterial cells. In some cases, the one or more bacterial cells are pathogens. In some cases, the one or more bacterial cells are infectious. Non-limiting examples of bacterial pathogens that can be detected include Mycobacteria (e.g. *M. tuberculosis, M. bovis, M. avium, M. leprae*, and *M. africanum*), rickettsia, mycoplasma, chlamydia, and legionella. Some examples of bacterial infections include, but are not limited to, infections caused by Gram positive *bacillus* (e.g., *Listeria, Bacillus* such as *Bacillus anthracis, Erysipelothrix* species), Gram negative *Bacillus* (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio* and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, and *Neisseria* species. Specific examples of infectious bacteria include, but are not limited to: *Helicobacter pyloris, Legionella pneumophilia, Mycobacterium tuberculosis, Mycobacterium avium, Mycobacterium intracellulare, Mycobacterium kansaii, Mycobacterium gordonae, Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus viridans, Streptococcus faecalis, Streptococcus bovis, Streptococcus pneumoniae, Haemophilus influenzae, Bacillus antracis, Erysipelothrix rhusiopathiae, Clostridium tetani, Enterobacter aerogenes, Klebsiella pneumoniae, Pasteurella multocida, Fusobacterium nucleatum, Streptobacillus moniliformis, Treponema pallidum, Treponema pertenue, Leptospira, Rickettsia*, and *Actinomyces israelii, Acinetobacter, Bacillus, Bordetella, Borrelia, Brucella, Campylobacter, Chlamydia, Chlamydophila, Clostridium, Corynebacterium, Enterococcus, Haemophilus, Helicobacter, Mycobacterium, Mycoplasma, Stenotrophomonas, Treponema, Vibrio, Yersinia, Acinetobacter baumanii, Bordetella pertussis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Corynebacterium diphtheriae, Enterobacter sazakii, Enterobacter agglomerans, Enterobacter cloacae, Enterococcus faecalis, Enterococcus faecium, Escherichia coli, Francisella tularensis, Helicobacter pylori, Legionella pneumophila, Leptospira interrogans, Mycobacterium leprae, Mycobacterium tuberculosis, Mycobacterium ulcerans, Mycoplasma pneumoniae, Pseudomonas aeruginosa, Rickettsia rickettsii, Salmonella typhi, Salmonella typhimurium, Salmonella enterica, Shigella sonnei, Staphylococcus epidermidis, Staphylococcus saprophyticus, Stenotrophomonas maltophilia, Vibrio cholerae, Yersinia pestis*, and the like.

The biological sample may comprise one or more viruses. Non-limiting examples of viruses include the herpes virus (e.g., human cytomegalomous virus (HCMV), herpes simplex virus 1 (HSV-1), herpes simplex virus 2 (HSV-2), varicella zoster virus (VZV), Epstein-Barr virus), influenza A virus and Hepatitis C virus (HCV) or a picornavirus such as Coxsackievirus B3 (CVB3). Other viruses may include, but are not limited to, the hepatitis B virus, HIV, poxvirus, hepadavirus, retrovirus, and RNA viruses such as flavivirus, togavirus, coronavirus, Hepatitis D virus, orthomyxovirus, paramyxovirus, rhabdovirus, bunyavirus, filo virus, Adenovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV). In some cases, the virus is an enveloped virus. Examples include, but are not limited to, viruses that are members of the hepadnavirus family, herpesvirus family, iridovirus family, poxvirus family, flavivirus family, togavirus family, retrovirus family, coronavirus family, filovirus family, rhabdovirus family, bunyavirus family, orthomyxovirus family, paramyxovirus family, and arenavirus family. Other examples include, but are not limited to, Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma—associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tickborne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus. In some embodiments, the virus is a non-enveloped virus, examples of which include, but are not limited to, viruses that are members of the parvovirus family, circovirus family, polyoma virus family, papillomavirus family, adenovirus family, iridovirus family, reovirus family, birnavirus family, calicivirus family, and picornavirus family. Specific examples include, but are not limited to, canine parvovirus, parvovirus B19, porcine circovirus type 1 and 2, BFDV (Beak and Feather Disease virus, chicken anaemia virus, Polyomavirus, simian virus 40 (SV40), JC virus, BK virus, Budgerigar fledgling disease virus, human papillomavirus, bovine papillomavirus (BPV) type 1, cotton tail rabbit papillomavirus, human adenovirus (HAdV-A, HAdV-B, HAdV-C, HAdV-D, HAdV-E, and HAdV-F), fowl adenovirus A, bovine adenovirus D, frog adenovirus, Reovirus, human orbivirus, human coltivirus, mammalian orthoreovirus, bluetongue virus, rotavirus A, rotaviruses (groups B to G), Colorado tick fever virus, aquareovirus A, cypovirus 1, Fiji disease virus, rice dwarf virus, rice ragged stunt virus, idnoreovirus 1, mycoreovirus 1, Birnavirus, bursal disease virus, pancreatic necrosis virus, Calicivirus, swine vesicular exanthema virus, rabbit hemorrhagic disease virus, Norwalk virus, Sapporo virus, Picornavirus, human polioviruses (1-3), human coxsackieviruses Al-22, 24 (CAl-22 and CA24, CA23 (echovirus 9)), human coxsackieviruses (Bl-6 (CB1-6)), human echoviruses 1-7, 9, 11-27, 29-33, vilyuish virus, simian enteroviruses 1-18 (SEV1-18), porcine enteroviruses 1-11 (PEVl-11), bovine enteroviruses 1-2 (BEV1-2), hepatitis A virus, rhinoviruses, hepatoviruses, cardio viruses, aphthoviruses and echoviruses. The virus may be phage. Examples of phages include, but are not limited to T4, T5, λ phage, T7 phage, G4, P1, p$^6$, Thermoproteus tenax virus 1, M13, MS2, QP, gpX174, 129, PZA, D15, BS32, B103, M2Y (M2), Nf, GA-1, FWLBc1, FWLBc2, FWLLm3, B4. In some cases, the virus is selected from a member of the Flaviviridae family (e.g., a member of the Flavivirus, Pestivirus, and Hepacivirus genera), which includes the hepatitis C virus, Yellow fever virus; Tick-borne viruses, such as the Gadgets Gully virus, Kadam virus, Kyasanur Forest disease virus, Langat virus, Omsk hemorrhagic fever virus, Powassan virus, Royal Farm virus, Karshi virus, tick-borne encephalitis virus, Neudoerfl virus, Sofjin virus, Louping ill virus and the Negishi virus; seabird tick-borne viruses, such as the Meaban virus, Saumarez Reef virus, and the Tyuleniy virus; mosquito-borne viruses, such as the Aroa virus, dengue virus, Kedougou virus, Cacipacore virus, Koutango virus, Japanese encephalitis virus, Murray Valley encephalitis virus, St. Louis encephalitis virus, Usutu virus, West Nile virus, Yaounde virus, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, yellow fever virus; and viruses with no known arthropod vector, such as the Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana *myotis* leukoencephalitis virus, Phnom Penh bat virus, Rio Bravo virus, Tamana bat virus, and the Cell fusing agent virus. In some cases, the virus is selected from a member of the Arenaviridae family, which includes the Ippy virus, Lassa virus (e.g., the Josiah, LP, or GA391 strain), lymphocytic choriomeningitis virus (LCMV), Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus, Chapare virus, and Lujo virus. In some cases, the virus is selected from a member of the Bunyaviridae family (e.g., a member of the Hantavirus, Nairovirus, Orthobunyavirus, and Phlebovirus genera), which includes the Hantaan virus, Sin Nombre virus, Dugbe virus, Bunyamwera virus, Rift Valley fever virus, La Crosse virus, Punta Toro virus (PTV), California encephalitis virus, and Crimean-Congo hemorrhagic fever (CCHF) virus. In some cases, the virus is selected from a member of the Filoviridae family, which includes the Ebola virus (e.g., the Zaire, Sudan, Ivory Coast, Reston, and Uganda strains) and the Marburg virus (e.g., the Angola, Ci67, Musoke, Popp, Ravn and Lake Victoria strains); a member of the Togaviridae family (e.g., a member of the Alphavirus genus), which includes the Venezuelan equine encephalitis virus (VEE), Eastern equine encephalitis virus (EEE), Western equine encephalitis virus (WEE), Sindbis virus, rubella virus, Semliki Forest virus, Ross River virus, Barmah Forest virus, O' nyong'nyong virus, and the chikungunya virus; a member of the Poxyiridae family (e.g., a member of the Orthopoxvirus genus), which includes the smallpox virus, monkeypox virus, and vaccinia virus; a member of the Herpesviridae family, which includes the herpes simplex virus (HSV; types 1, 2, and 6), human herpes virus (e.g., types 7 and 8), cytomegalovirus (CMV), Epstein-Barr virus (EBV), Varicella-Zoster virus, and Kaposi's sarcoma associated-herpesvirus (KSHV); a member of the Orthomyxoviridae family, which includes the influenza virus (A, B, and C), such as the H5N1 avian influenza virus or H1N1 swine flu; a member of the Coronaviridae family, which includes the severe acute respiratory syndrome (SARS) virus; a member of the Rhabdoviridae family, which includes the rabies virus and vesicular stomatitis virus (VSV); a member of the Paramyxoviridae family, which includes the human respiratory syncytial virus (RSV), Newcastle disease virus, hendravirus, nipahvirus, measles virus, rinderpest virus, canine distemper virus, Sendai virus, human parainfluenza virus (e.g., 1, 2, 3, and 4), rhinovirus, and mumps virus; a member of the Picornaviridae family, which includes the poliovirus, human enterovirus (A, B, C, and D), hepatitis A virus, and the coxsackievirus; a member of the Hepadnaviridae family, which includes the hepatitis B virus; a member of the Papillamoviridae family, which includes the human papilloma virus; a member of the Parvoviridae family, which includes the adeno-associated virus; a member of the Astroviridae family, which includes the astrovirus; a member of the Polyomaviridae family, which includes the JC virus, BK virus, and SV40 virus; a member of the Calciviridae family, which includes the Norwalk virus; a member of the Reoviridae family, which includes the rotavirus; and a member of the Retroviridae family, which includes the human immunodeficiency virus (HIV; e.g., types 1 and 2), and human T-lymphotropic virus Types I and II (HTLV-1 and HTLV-2, respectively).

The biological sample may comprise one or more fungi. Examples of infectious fungal agents include, without limitation *Aspergillus, Blastomyces, Coccidioides, Cryptococcus, Histoplasma, Paracoccidioides, Sporothrix*, and at least three genera of *Zygomycetes*. The above fungi, as well as many other fungi, can cause disease in pets and companion animals. The present teaching is inclusive of substrates that contact animals directly or indirectly. Examples of organisms that cause disease in animals include *Malassezia furfur, Epidermophyton floccosur, Trichophyton mentagrophytes, Trichophyton rubrum, Trichophyton tonsurans, Trichophyton equinum, Dermatophilus congolensis, Microsporum canis, Microsporu audouinii, Microsporum gypseum, Malassezia ovale, Pseudallescheria, Scopulariopsis, Scedosporium*, and *Candida albicans*. Further examples of fungal infectious agent include, but are not limited to, *Aspergillus, Blastomyces dermatitidis, Candida, Coccidioides immitis, Cryptococcus neoformans, Histoplasma capsulatum var. capsulatum, Paracoccidioides brasiliensis, Sporothrix schenckii, Zygomycetes* spp., *Absidia corymbifera, Rhizomucor pusillus*, or *Rhizopus arrhizus*.

The biological sample may comprise one or more parasites. Non-limiting examples of parasites include *Plasmodium, Leishmania, Babesia, Treponema, Borrelia, Trypanosoma, Toxoplasma gondii, Plasmodium falciparum, P. vivax, P. ovale, P. malariae, Trypanosoma* spp., or *Legionella* spp. In some cases, the parasite is *Trichomonas vaginalis*.

In some cases, the biological sample is a sample taken from a subject infected with or suspected of being infected with an infectious agent (e.g., bacteria, virus). In some aspects, the biological sample comprises an infectious agent associated with a sexually-transmitted disease (STD) or a sexually-transmitted infection (STI). Non-limiting examples of STDs or STIs and associated infectious agents that may be detected with the devices and methods provided herein may include, Bacterial Vaginosis; Chlamydia (*Chlamydia trachomatis*); Genital herpes (herpes virus); Gonorrhea (*Neisseria gonorrhoeae*); Hepatitis B (Hepatitis B virus); Hepatitis C (Hepatitis C virus); Genital Warts, Anal Warts, Cervical Cancer (Human Papillomavirus); Lymphogranuloma venereum (*Chlamydia trachomatis*); Syphilis (*Treponema pallidum*); Trichomoniasis (*Trichomonas vaginalis*); Yeast infection (*Candida*); and Acquired Immunodeficiency Syndrome (Human Immunodeficiency Virus).

In some cases, the sample can be from an environmental source or an industrial source. Examples of environmental sources include, but are not limited to, agricultural fields, lakes, rivers, water reservoirs, air vents, walls, roofs, soil samples, plants, and swimming pools. Examples of industrial sources include, but are not limited to clean rooms, hospitals, food processing areas, food production areas, food stuffs, medical laboratories, pharmacies, and pharmaceutical compounding centers. The sample can be a forensic sample (e.g., hair, blood, semen, saliva, etc.). The sample can comprise an agent used in a bioterrorist attack (e.g., influenza, anthrax, smallpox).

In some cases, more than one sample can be obtained from a subject or source, and multiple immunoassay tests using a single sensing device or apparatus described herein can be performed. In some cases, 2, 3, 4, 5, 6, 7, 8, 9, 10, 15, 20, 25, 30, 35, 40, 45, 50 or more samples can be obtained. In some cases, more than one sample may be obtained over a period of time, for example, to monitor disease progression or to monitor a biological state or condition (e.g., cardiac conditions). Generally, the sensing devices of the disclosure are configured for repeated or continuous use. Alternatively, the sensing devices can be one-time use (e.g., disposable).

In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The biological sample can be from a subject who has a specific disease, disorder, or condition, or is suspected of having (or at risk of having) a specific disease, disorder or condition. For example, the biological sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloeptithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, non-melanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient. In some cases, the sample is a biopsy of a tumor.

The biological sample can be processed to render it competent for performing any of the methods using any of the devices or kits provided herein. For example, a solid sample may be dissolved in a liquid medium or otherwise prepared as a liquid sample to facilitate flow along the test strip of the device. In such cases where biological cells or particles are used, the biological cells or particles may be lysed or otherwise disrupted such that the contents of the cells or particles are released into a liquid medium. Molecules contained in cell membranes and/or cell walls may also be released into the liquid medium in such cases. A liquid medium may include water, saline, cell-culture medium, or any solution and may contain any number of salts, surfactants, buffers, reducing agents, denaturants, preservatives, and the like.

Generally, the sample contains or is suspected of containing one or more target analytes. In various aspects, the sample may contain at least a first analyte and a second analyte. The term "analyte" as used herein may refer to any substance that is to be analyzed using the methods and devices provided herein. The immunoassay sensing devices and arrays disclosed herein may be configured to simultaneously detect the presence of 1, 2, 3, 4, 5, 6, 7, 8, 9, 10 or more analytes in a sample. The immunoassay sensing devices and arrays disclosed herein can be capable of simultaneous and multiplexed detection of multiple target analytes in a single sample.

Non-limiting examples of analytes may include proteins, haptens, immunoglobulins, hormones, polynucleotides, steroids, drugs, infectious disease agents (e.g., of bacterial or viral origin), drugs of abuse, environmental agents, biological markers, and the like. In one case, the immunoassay detects at least a first analyte, wherein the first analyte is luteinizing hormone (LH). In another case, the immunoassay detects at least a first analyte, wherein the first analyte is human chorionic gonadotropin (hCG). In another case, the immunoassay detects at least a first analyte and a second analyte, wherein the first analyte is estrone-3-glucoronide (E3G) and the second analyte is luteinizing hormone (LH). In another case, the immunoassay detects at least a first analyte and a second analyte, wherein the first analyte is a surface antigen on a first viral particle (e.g., Influenza A) and the second analyte is a surface antigen on a second viral particle (e.g., Influenza B). In another case, the immunoassay detects at least a first analyte, wherein the first analyte is 25-hydroxyvitamin D, 25-hydroxyvitamin D2 [25(OH)$D_2$], or 25-hydroxyvitamin D3 [25(OH)$D_3$]. In another case, the immunoassay detects at least a first analyte and a second analyte, wherein the first analyte is triiodothyronine (T3) and the second analyte is thyroxine (T4). In another case, the immunoassay detects at least a first analyte, wherein the first analyte is an allergen. Non-limiting examples of allergens may include: Balsam of Peru, fruit, rice, garlic, oats, meat, milk, peanuts, fish, shellfish, soy, tree nuts, wheat, hot peppers, gluten, eggs, tartrazine, sulfites, tetracycline, phenytoin, carbamazepine, penicillin, cephalosporins, sulfonamides, non-steroidal anti-inflammatories (e.g., cromolyn sodium, nedocromil sodium, etc.), intravenous contrast dye, local anesthetics, pollen, cat allergens, dog allergens, insect stings, mold, perfume, cosmetics, semen, latex, water, house dust mites, nickel, gold, chromium, cobalt chloride, formaldehyde, photographic developers, fungicide, dimethylaminopropylamine, paraphenylenediamine, glyceryl monothioglycolate, toluenesulfonomide formaldehyde.

The sensing device may be used to test for the presence or absence of at least a first analyte and a second analyte in a sample. In some cases, the sensing device may be used to determine an amount or a relative amount of at least a first and second analyte in a sample.

The presence or absence of analytes may be indicative of a disease or disorder in a subject. The presence or absence of analytes may be indicative of a biological state or condition of a subject. In some cases, the presence or absence of analytes indicates that a subject has or is at risk of developing a disease. In some cases, the presence or absence of analytes indicates that a subject has a disorder (e.g., thyroid disorder). In some cases, the presence or absence of analytes indicates that a subject has a deficiency (e.g., vitamin deficiency). In some cases, the presence or absence of analytes indicates that a product (e.g., a food or drink product) contains an allergen.

G. Sensing Mechanisms

The sensing device 100 may be an electrochemical sensing device configured for both catalytic and affinity-based detection of one or more target analytes in a sample. A catalytic sensor(s) or catalytic sensing utilizes molecules (such as enzymes) that catalyze a biochemical reaction on the sensing surface with the target molecule and detection based on the resulting products. An affinity-based sensor(s) or affinity-based sensing is designed to monitor binding of the target molecule and uses other specific binding molecules (e.g., proteins, lectins, receptors, nucleic acids, whole cells, aptamers, DNA/RNA, antibodies or antibody-related substances, etc.) for biomolecular recognition.

In many embodiments, the sensing devices or arrays disclosed herein can be configured to simultaneously detect and quantitate different isoforms of a single protein. The molecules associated with the catalysis-based reaction may be anchored onto the sensing surface (e.g. working electrode) through an affinity-based mechanism to ensure that the chemical reaction(s) occurs in proximity of the sensing surface for enhanced sensitivity of detection. The output electrical signals for both catalytic and affinity sensors/sensing is measured in current, voltage, and impedance.

Amperometric (i.e. DC current—DC voltage—time) and impedimetric sensors are electroanalytical methods for characterization of the surface phenomena and changes at the sensing electrode surfaces. Amperometric sensors can measure changes to electric current resulting from either catalytic mechanisms and/or affinity binding mechanisms occurring at the sensing electrode surfaces under an applied field/potential and that are related to the concentration of the target species or analytes present in the solution. Voltammetry and chronoamperometry are subclasses of amperometry. In voltammetry, current is measured by varying the potential applied to the sensing electrode. In chronoamperometry, current is measured at a fixed potential, at different times after the start of sensing.

The aforementioned sensors and sensing methods are particularly well-suited for detection of catalytic processes and their associated effects modulated due to kinetic and thermodynamic properties. Signal transduction and quantification occurs through the dynamic transfer of electrons resulting from the catalytic processes and/or the associated chemical reactions to the sensing electrode surface. Specificity in detection of target species or analytes can be achieved through the choice of the catalytic processes and the higher reaction rate kinetics occurring within the electrochemical potential window, which can result in amplified signals through the sensing electrode surface.

Impedimetric sensors are well-suited for detection of binding events on the sensing electrode surface. Analytes can interact with the sensing electrode through selective treatments applied to the electrode surface in the form of cross-linkers (e.g., antibodies, nucleic acids, ligands, etc.) that are covalently conjugated onto sensing electrode surface. The impedance Z of the sensor can be determined by applying a voltage perturbation with a small amplitude and detecting the current response. The impedance Z is the quotient of the voltage-time function V(t) and the resulting current-time function I(t), and given as follows:

$$Z = \frac{V(t)}{I(t)} = \frac{V_0 \sin(2\Pi f t)}{I_0 \sin(2\Pi f t + \phi)} = \frac{1}{Y}$$

where $V_0$ and $I_0$ are the maximum voltage and current signals, f is the frequency, t the time, φ the phase shift between the voltage-time and current-time functions, and Y is the complex conductance or admittance. The measured impedance associated with biomolecule binding is a complex value, since the current can differ in terms of not only the amplitude but also it can show a phase shift φ compared to the voltage-time function. Thus, the value can be described either by the modulus |Z| and the phase shift φ or alternatively by the real part ZR and the imaginary part ZI of the impedance. Therefore, the results of an impedance measurement can be illustrated in two different ways: using a Bode plot, which plots log |Z| and φ as a function of log f, or using a Nyquist plot, which plots ZR and ZI. Both of these plots can be used to establish calibration responses of the sensing device towards real-time detection and quantification of the target species or analytes. Sensitivity and specificity in detection can be achieved through deconstruction of the Nyquist and Bode plots, by identifying the frequency range where the electrical double layer effects due to the binding events of the target species occur and quantifying the change in impedance with concentration within this range.

In various embodiments, when a working electrode comprising ZnO nanostructures is exposed to a sample (e.g., an ionic solution comprising biomolecules), a potential difference is generated at the electrode/electrolyte interface due to the unequal distribution of charges. As a consequence of biomolecular binding events at the surface of the ZnO nanostructures, redistribution of charges in the working electrode and ions in the electrolyte can result in formation of a space-charge region within the ZnO nanostructures and an electrical double layer at the interface between the electrode and the electrolyte. Evaluation and quantification of biomarker binding can be achieved by measuring the changes in electrode resistance or capacitance at selected frequencies.

The changes to space-charge capacitance and overall impedance at the ZnO nanostructures/electrolyte interfaces can be characterized by respectively using a direct current (DC)-based Mott-Schottky technique and an alternating current (AC)-based electrochemical impedance spectroscopy (EIS) technique towards detection of target analytes or biomarkers. Correlation in output signal response with concentration can be established between the DC and AC electrochemical detection techniques.

As previously described, the plurality of capture reagents of the sensing device are configured to selectively bind to one or more target analytes in a sample, thereby effecting changes to electron and ion mobility and charge accumulation in different regions of the semiconducting nanostructures and the sample. The changes to the electron and ion mobility and charge accumulation can be detected with aid of sensing circuitry, and can be used to determine a presence and concentration of the one or more target analytes in the sample. The changes to the electron and ion mobility and charge accumulation can be transduced into electrical impedance and capacitance signals. The signals may be indicative of interfacial charge modulation comprising of the changes to the electron and ion mobility. Additionally, the signals may be indicative of capacitance changes to a space-charge region formed in the semiconducting nanostructures upon binding of the one or more target analytes to the capture reagents. The changes may comprise simultaneous modulation to the ion mobility in one or more regions adjacent or proximal to the semiconducting nanostructures.

The sensing circuitry may comprise hardware, software, or a combination of software and hardware. The sensing circuitry may comprise a single or multiple microprocessors, field programmable gate arrays (FPGAs), or digital signal processors (DSPs). The sensing circuitry may be electrically connected to the sensing device. In some embodiments, the sensing circuitry may be part of the sensing device, for example the sensing circuitry may be assembled or disposed on the substrate. Alternatively, the sensing circuitry may be remote to the sensing device.

The sensing circuitry can be configured to implement a plurality of electrochemical detection techniques for detecting the capacitance changes and impedance changes. The plurality of electrochemical detection techniques may comprise, for example (1) a modified Electrochemical Impedance Spectroscopy (EIS) technique for measuring the impedance changes and (2) Mott-Schottky technique for measuring the capacitance changes. The modified EIS technique is capable of distinguishing the electrical impedance signals from background noise at low concentrations of the target analytes in the sample. The sensing circuitry can be configured to analyze the electrical impedance and capacitance signals by concurrently analyzing a set of Nyquist plots obtained via the modified EIS technique and a set of Mott-Schottky plots obtained via the Mott-Schottky technique. The modified EIS technique may comprise (1) sectioning an interfacial charge layer into a plurality of spatial dielectric z-planes along a direction orthogonal to the interface between the fluid sample and the semiconducting nanostructures, and (2) probing each of the plurality of z-planes with a specific frequency selected from a range of frequencies. Specific binding of different target analytes to the capture reagents may occur at known spatial heights within the interfacial charge layer. Accordingly, the sensing circuitry can be configured to determine the presence and concentration of each of the different target analytes by measuring the capacitance and impedance changes at specific frequencies corresponding to their respective z-planes at the known spatial heights within the interfacial charge layer.

H. Room-Temperature Ionic Liquids (RTIL)

The inherent non-stoichiometric nature of ZnO may result in generation of oxygen vacancies, and the ease in forming surface bonds with hydroxyl molecules and other ions can render the ZnO surface sensitive to the pH of the biofluids and environment. Thus, ZnO-based sensing devices may develop drifts in signal output over time, independent of detection modality, especially when exposed to varying pH solutions in the presence of enzymatic reactions that involve generation of hydrogen peroxide. In addition, protein biomolecules can easily denature when exposed to temperature, environment, and pH outside the established range of their stability.

To mitigate the above effects, a sample may be provided in a room temperature ionic liquid (RTIL) electrolyte buffer in some embodiments. The stability and reliability of the bound proteins to the functionalized nanostructured ZnO surfaces can be improved with the use of RTIL as the electrolyte solvent buffer containing the specific protein antibodies, and that can conjugate with the functionalized ZnO surface during the immunoassay steps. The RTIL can also provide stability of the bound proteins during subsequent storage and handling and from exposure to environment. In simple electrolyte solvent solutions, the protein charge is typically determined by the equilibrium protonation of hydroxyl- and amino-groups, and depends on the pH of the environment, whose variations can even reverse the sign of the overall charge. In contrast, for RTILs, dispersion energy, ion size, and additional H-bonding sites can be useful in determining protein characteristics. Unlike molecular solvents that are charge neutral, RTILs are molten salts at room temperature composed solely of polyatomic cations and anions.

The properties of RTILs can be changed according to the requirement by modifying their constituents (cation and anion). Although they can stabilize the protein over a wide range of temperature, the thermal stability of proteins depends on the appropriate choice of RTILs as proteins are not homogeneously stable in all type of RTILs. In some cases, the stability and activity of proteins is affected by many factors such as polarity, hydrophilicity vs. hydrophobicity and hydrogen-bond capacity of RTILs, excipients, and impurities. RTILs containing chaotropic (large-sized and low charged, weakly hydrated ions that decrease the structure of water) cations and kosmotropic (small-sized and high charged, strongly hydrated ions that increase the structure of water) anions can optimally stabilize the biological macromolecules. In some embodiments, the kosmotropicity order of anions and cations can be determined by using viscosity B-coefficients and other parameters such as hydration entropies, hydration volumes, heat capacity, NMR B-coefficients and ion mobility.

In one embodiment, RTILs containing chaotropic cations and kosmotropic anions can be selected to independently and optimally stabilize the target proteins chosen i.e. cTnI and/or cTnT, NT-proBNP, and CRP. Intermixing of protein biomolecules and ensuring cross-reactivity response is well below the noise threshold in signal transduction response from each of the bound antibodies in the detection of their specific target proteins can be achieved.

III. Multi-Configurable Sensing Array

In some embodiments, the plurality of semiconducting nanostructures may be disposed on two or more electrodes comprising of a first electrode and a second electrode. A first capture reagent may be attached to the semiconducting nanostructures on the first electrode and configured to selectively bind to a first target analyte. A second capture reagent may be attached to the semiconducting nanostructures on the second electrode and configured to selectively bind to a second target analyte. The sensing device is capable of simultaneously determining the presence and concentrations of the first and second target analytes upon binding of the target analytes to the respective capture reagents.

Figure 2:
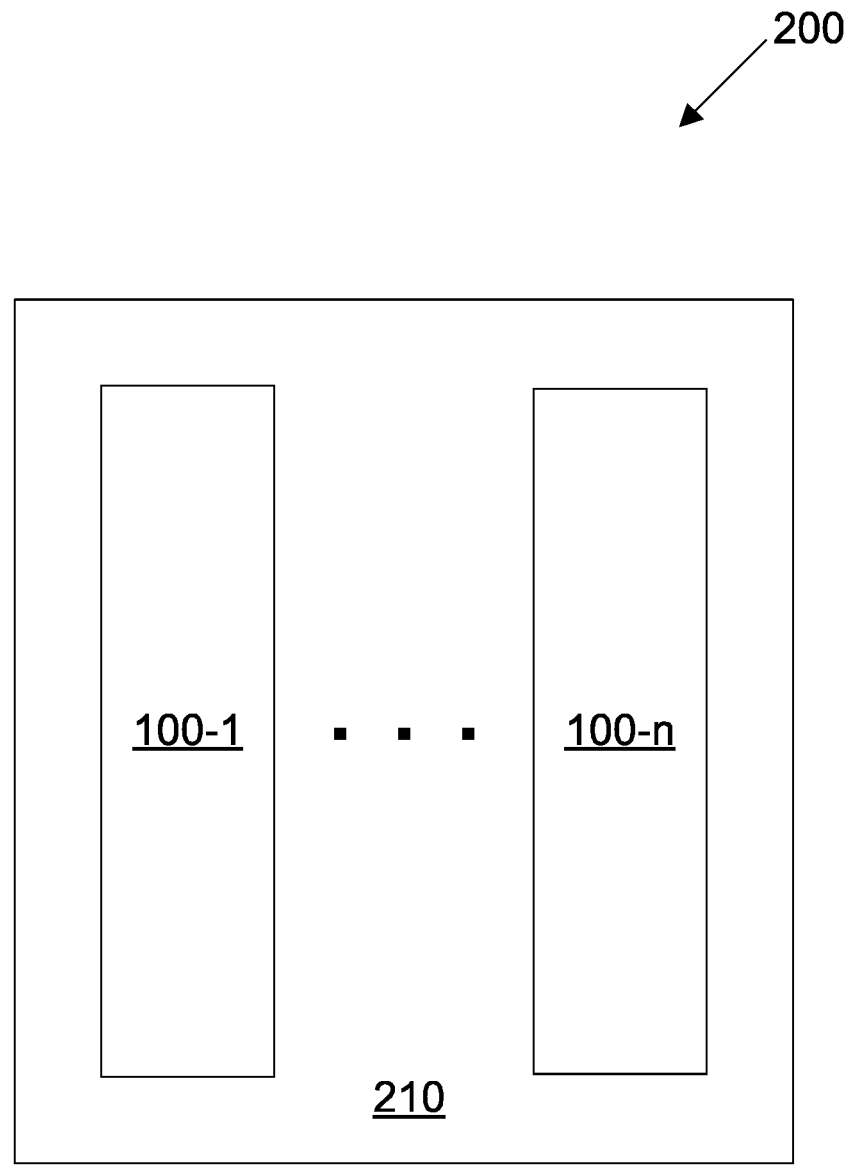
FIG. 2 shows a sensing array comprising a plurality of sensing devices for detecting different target analytes.

In some embodiments, the first electrode may be part of a first sensing device, and the second electrode may be part of a second sensing device. The first and second sensing devices may be provided on a common sensing platform. For example, FIG. 2 shows a sensing array 200 comprising a plurality of sensing devices 100 for detecting a plurality of different target analytes in a fluid sample. The array may comprise two or more sensing devices (e.g., 100-1 through 100-$n$, where n can be any integer greater than two) disposed on a common substrate 210. Alternatively, the sensing devices may be provided separately and then assembled onto the substrate 210. The sensing devices may each comprise a working electrode having a plurality of semiconducting nanostructures disposed thereon and a capture reagent attached to the semiconducting nanostructures. The sensing devices may or may not have the same type of semiconducting nanostructures or materials. The sensing devices may comprise different capture reagents that are configured to selectively bind to the different target analytes in the fluid sample. The selective binding is configured to effect changes to electron and ion mobility and charge accumulation in different regions of the semiconducting nanostructures and the fluid sample. Each of the sensing devices can be configured to determine a presence and concentration of a different target analyte in the fluid sample based on detected changes to the electron and ion mobility and charge accumulation.

A method of detecting a plurality of different target analytes in a fluid sample may include providing the sensing array described herein, and applying the fluid sample containing one or more target analytes to the sensing array. The method may include using each of the sensing devices to determine the presence and concentration of a different target analyte in the fluid sample, based on the detected changes to the electron and ion mobility and charge accumulation in the different regions of the semiconducting nanostructures and the fluid sample.

In some embodiments, an array 200 may comprise a first sensing device 100-1 and a second sensing device 100-2 capable of simultaneously determining the presence and concentrations of first and second target analytes upon binding of the target analytes to the respective capture reagents. In some embodiments, the first and second target analytes may comprise different isoforms of a same type of biomarker. In some embodiments, the target analytes may comprise a plurality of cardiac biomarkers, and the plurality of capture reagents may comprise a plurality of antibodies that are specific to the plurality of cardiac biomarkers.

A. Simultaneous and Multiplexed Detection of Multiple Target Analytes

As noted previously, there is a need for the rapid, quantitative, specific, and multiplex detection and measurement of target analyte concentrations at point of care. The ability to perform multiplexed detection can provide significant advantages for point of care diagnostics in that it allows for the simultaneous monitoring of multiple markers in a single sample. The multiplexing can support the performance of both negative and positive controls in the same sample. Together, these attributes can significantly improve the specificity and sensitivity with which certain diseases and physiological conditions can be detected and diagnosed.

Figure 3:
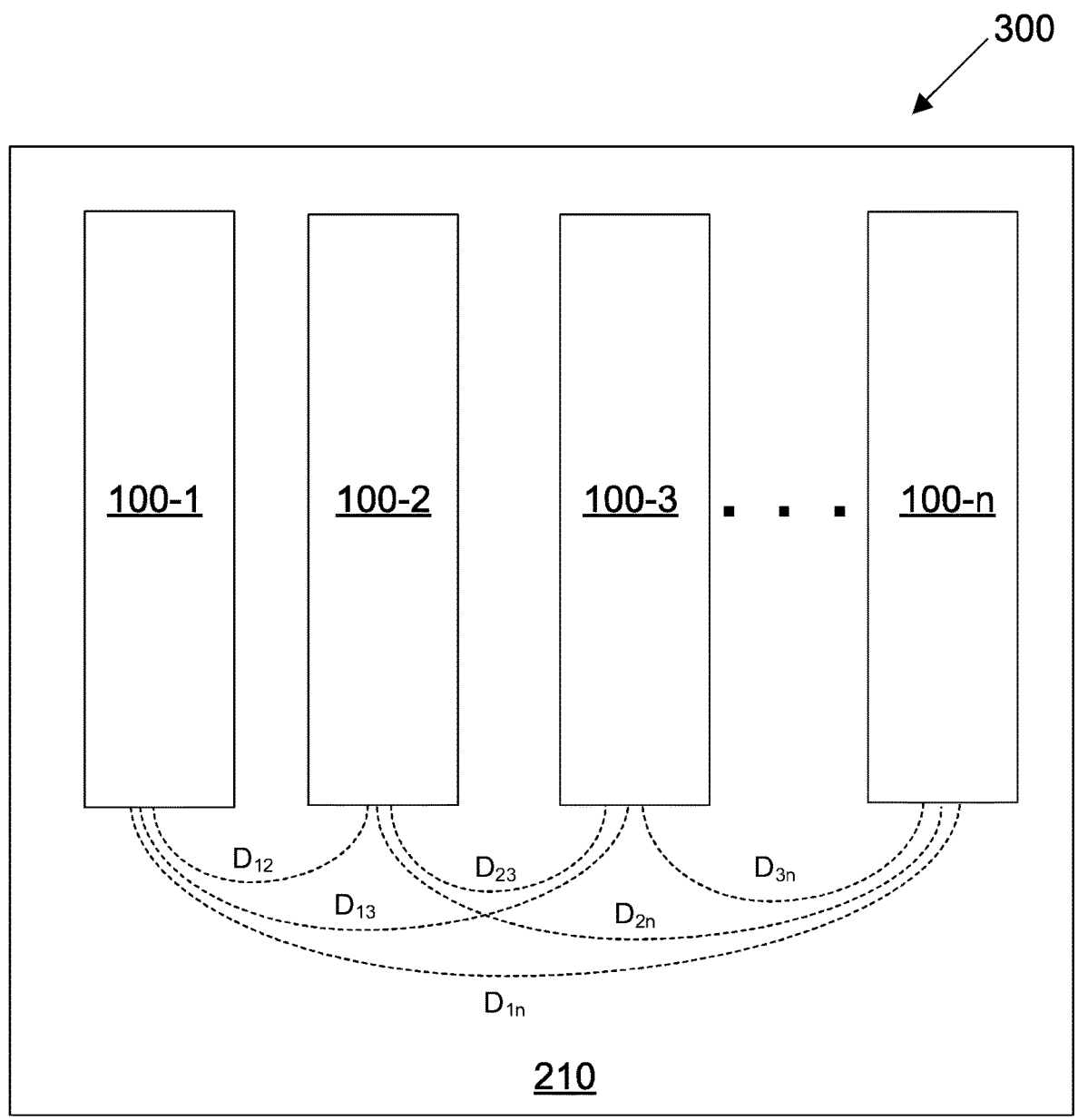
FIG. 3 shows a multi-configurable sensing array comprising a plurality of sensing devices configured for simultaneous and multiplexed detection of a plurality of target analytes.

The array 200 shown in FIG. 2 is capable of simultaneous and multiplexed detection of different target analytes present in a fluid sample using a plurality of electrochemical detection techniques. FIG. 3 shows a multi-configurable sensing array 300 comprising a plurality of sensing devices 100-1, 100-2, 100-3 through 100-$n$. The electrodes of the sensing devices can be connected to sensing circuitry configured for simultaneous acquisition and multiplexing of electrical signals from the sensing devices. The sensing devices can be configured for both catalytic and affinity-based sensing. A working electrode in each sensing device can be independently functionalized for specific detection of a target analyte which may be a biomarker. Different sensing devices in the array 300 may comprise different capture reagents that are configured to selectively bind to the different target analytes in the fluid sample. The output from each sensing device may be independently measured and transduced (e.g., amperometric or impedometric) to provide a combinatorial/multiplexed result relating to the end physiological state being predicted. For example, $D_{12}$ may be the multiplexed result between sensing devices 100-1 and 1002; $D_{23}$ may be the multiplexed result between sensing devices 100-2 and 1003; $D_{13}$ may be the multiplexed result between sensing devices 100-1 and 1003; Din may be the multiplexed result between sensing devices 100-1 and 100-n, and so forth. In some embodiments, the output from more than two sensing devices, or all of the sensing devices, may be independently measured and transduced (e.g., amperometric or impedometric) to provide a combinatorial/multiplexed result relating to the end physiological state being predicted. For example, $D_{123\ldots n}$ may be the multiplexed result between sensing devices 100-1, 100-2, 100-3 through 100-n. Any number or combination of multiplexed results from the sensing devices may be contemplated. The output from the two or more sensing devices can be weighed the same (e.g. each output accorded a same weight) or weighed differentially (e.g. different outputs accorded different weights). In some embodiments, the output from a sensing device may be compared or correlated with the output(s) of one or more other sensing devices. For example, the output from sensing device 100-1 may be compared or correlated with the output(s) of one or more other sensing devices (e.g, 100-2, 100-3) to improve specificity and sensitivity in detecting and diagnosing certain diseases and physiological conditions.

The multi-configurable array 300 can be configured for detection of multiple analytes that may be useful in disease detection. In some embodiments, the array can be used for paired and simultaneous detection of disease markers in body fluids in a non-invasive manner such as: (a) Inflammatory marker, interleukin-6 (IL-6) and diabetes marker, Glucose in human sweat; and/or (b) Inflammatory markers, interleukin-6 (IL-6) and C-reactive protein (CRP) and muscular dystrophy markers, creatine kinase (CK-MB) in finger pricked capillary blood. In some embodiments, the array can be integrated with other sensors within wearable fabric, devices, and medical instruments such as strips, catheters, probes, patches for non-communicable disease diagnosis such as cardiac, cancer, Alzheimer's, muscular dystrophy, inflammatory markers, etc.

The array 300 may be capable of supporting simultaneous detection of multiple target analytes in a single sample volume. The volume may be 150 µL, 140 µL, 130 µL, 120 µL, 110 µL, 100 µL, 90 µL, 80 µL, 70 µL, 60 µL, 50 µL, 40 µL, 30 µL, 20 µL, 10 µL, 1 µL, or any value therebetween. In some embodiments, the array 300 may be capable of supporting simultaneous detection of multiple target analytes in a single, submilliliter sample volume (e.g. <30 µL). In some embodiments, simultaneous and multiplexed detection of the target analytes can be completed in a short time (e.g., on the order of a few minutes or less), and using <20 µL of sample volume. In some embodiments, simultaneous and multiplexed detection of the target analytes can be achieved using about 10-20 µL of sample volume.

B. Electrode Configurations

Figure 4:
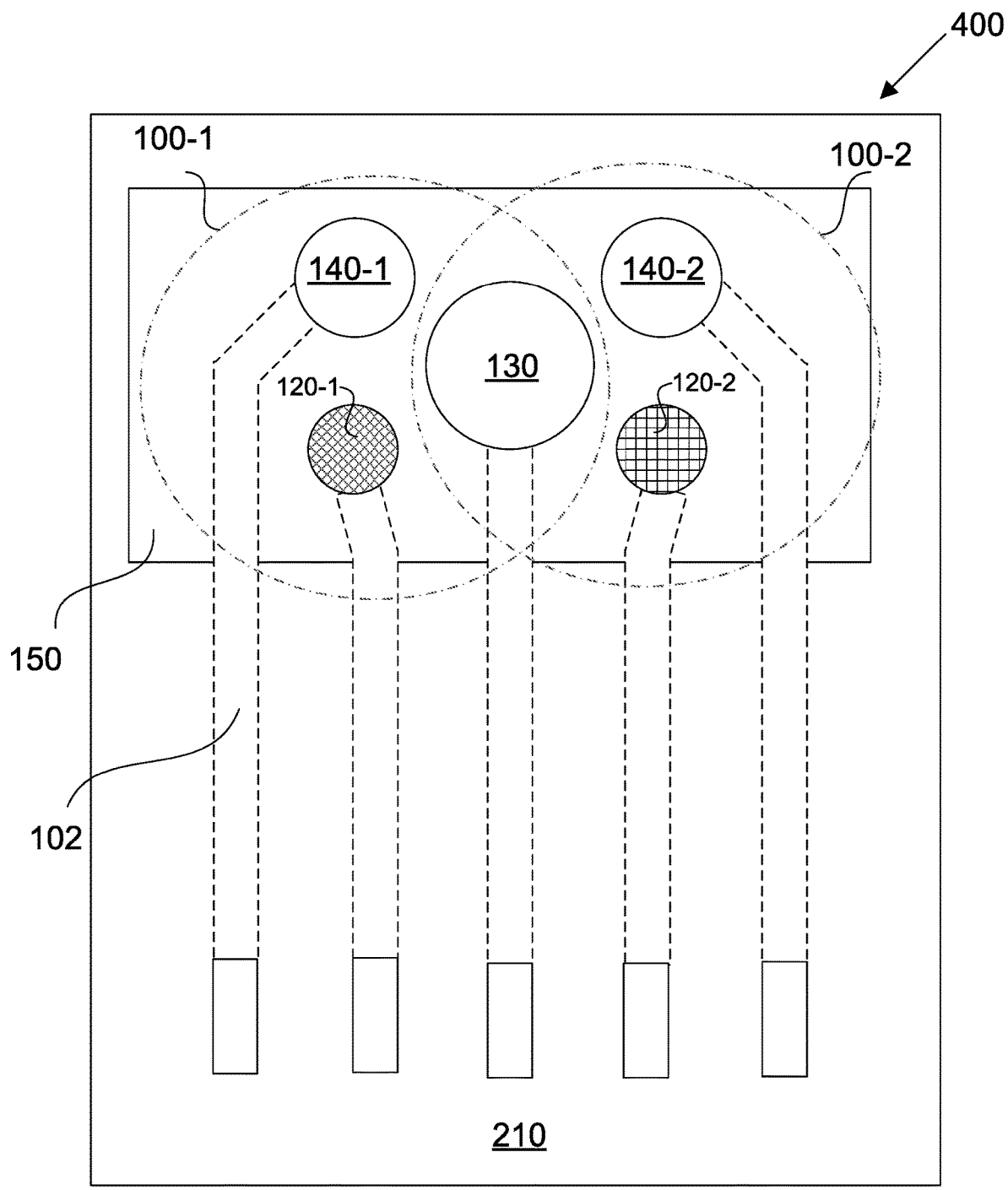
FIG. 4 shows a multi-configurable sensing array in accordance with some embodiments.

FIG. 4 shows an array 400 comprising a first sensing device 100-1 and a second device 100-2 in accordance with some embodiments. The first and second sensing devices may be similar to the sensing devices described elsewhere herein. In the example of FIG. 4, the first and second sensing devices may share a common reference electrode (RE) 130, instead of each sensing device having its own reference electrode. The common reference electrode can provide a stable and known electrode potential to the electrochemical cell comprising of the first and second sensing devices. The first and second sensing devices can operate based on the same reference electrode potential, thereby permitting simultaneous and multiplexed detection of target analytes, and calibration of results between the two sensing devices.

The first sensing device 100-1 may comprise a working electrode (WE) 120-1 and a counter electrode (CE) 140-1. The second sensing device 100-2 may comprise a working electrode (WE) 120-2 and a counter electrode (CE) 140-2. The common RE 130 may be disposed between the working electrodes of the two sensing devices. The common RE 130 may also be disposed between the counter electrodes of the two sensing devices. The WE 120-1, RE 130, and CE 140-1 may be located in proximity to each other in a first region of the substrate 210. The WE 120-2, RE 130, and CE 140-2 may be located in proximity to each other in a second region of the substrate 210. The first and second regions may be part of a test zone 150. The first sensing device may comprise a first capture reagent configured to selectively bind to a first target analyte. The second sensing device may comprise a second capture reagent configured to selectively bind to a second target analyte. In some embodiments, the common RE 130 may have a larger surface area than each of the working electrodes and counter electrodes. For example, the surface areas of WE:CE:RE may be designed in the ratio of 1:1:4 to ensure sufficient output signal response due to binding events at the working electrodes.

IV. Sensing System

Figure 5:
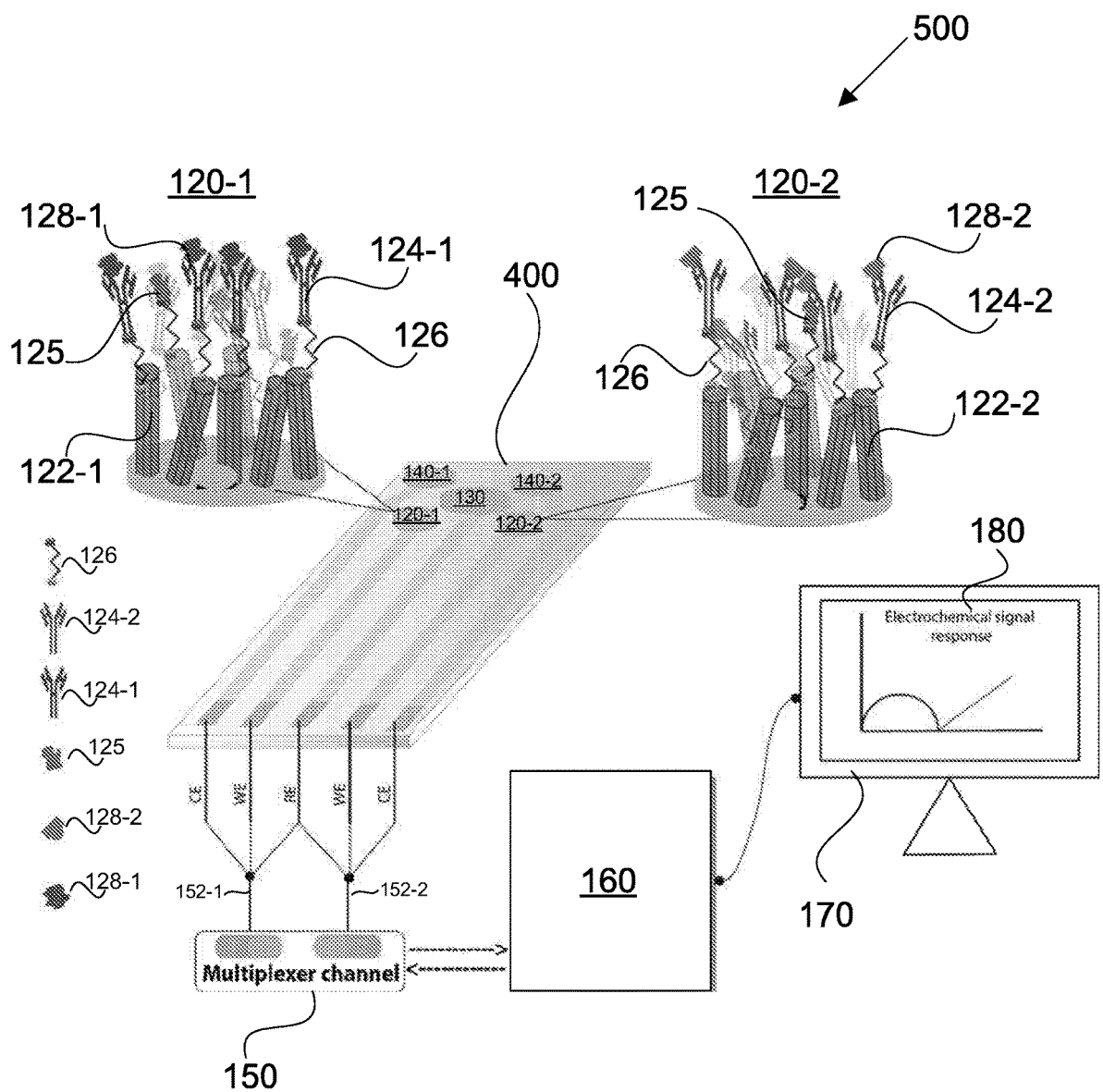
FIG. 5 shows a multi-configurable sensing system in accordance with some embodiments.

FIG. 5 shows a sensing system 500 in accordance with some embodiments. The system 500 may comprise a multi-configurable array of sensing devices, for example array 400 described with reference to FIG. 4. The array 400 may comprise a first sensing device and a second sensing device as described elsewhere herein. The first sensing device may include a first working electrode (WE) 120-1 and a first counter electrode (CE) 140-1. The second sensing device may include a second working electrode (WE) 120-2 and a second counter electrode (CE) 140-1. The first and second sensing devices may share a common reference electrode (RE) 130.

FIG. 5 further shows a magnified schematic view of the functionalized working electrode (WE) 120 of each sensing device. As previously described, each working electrode can be independently functionalized for specific detection of a target biomarker(s). The output from each sensing device can be independently measured and transduced (e.g., amperometric or impedometric) to provide a multiplexed outcome relating to the end physiological state being predicted.

Referring to FIG. 5, a plurality of semiconducting nanostructures 122 may be disposed on the WEs 120. For example, first semiconducting nanostructures 122-1 may be disposed on the surface of the first WE 120-1, and second semiconducting nanostructures 122-2 may be disposed on the surface of the second WE 120-2. In some embodiments, the first and second semiconducting nanostructures may be formed of a same semiconductor or semiconductor alloy material. Alternatively, the first and second semiconducting nanostructures may be formed of different types of semiconductor or semiconductor alloy material. In some instances, each of the first and second semiconducting nanostructures may comprise two or more types of semiconductor or semiconductor alloy material. The semiconducting nanostructures can be grown or deposited on the surface of the working electrodes. In some embodiments, the first and second semiconducting nanostructures may comprise ZnO nanostructures, as described in more detail with reference to FIGS. 6A-C.

Figure 6A:
FIGS. 6A-6C show an SEM micrograph and ATR-FTIR spectra of ZnO nanostructures selectively grown on a working electrode, in accordance with some embodiments.

FIG. 6A shows an SEM micrograph of ZnO nanostructures that are selectively grown on the working electrodes of the sensing array using low temperature aqueous hydrothermal growth mechanism. The nanostructures may be elongated, and may include nanorods or nanopillars. In some embodiments, the nanostructures may have an aspect ratio of about 1:4. The nanostructures may be formed having different shapes, sizes, dimensions, and/or aspect ratios depending on the growth conditions. In some embodiments, the ZnO nanostructures may be grown by tuning the chemical reactions between the precursors $Zn(NO3)2.6H2O$ and HMTA dissolved in water. The thermal decomposition and hydrolysis reactions of these precursors results in the formation of zinc hydroxyl species which upon dehydration form ZnO nuclei. Pre-seeded regions on the working electrodes can then act as nucleation sites for the aligned growth of ZnO nanostructures. The higher surface energy difference between polar and non-polar planes derives faster growth of ZnO along polar planes resulting in c-axis oriented crystalline growth of wurtzite ZnO nanostructures. The SEM micrograph in FIG. 6A shows the morphology of synthesized ZnO nanostructures as vertically grown hexagonal shaped rod-like structures and uniform growth on the working electrodes. The SEM characterization indicates uniform growth of hexagonal shaped ZnO nanostructures at the pre-seeded working electrodes. The as-synthesized ZnO nanostructures can be used to aid detection of various target analytes (e.g. cardiac biomarkers) using the sensing array of FIGS. 4 and 5 as described elsewhere herein.

Figure 6B:
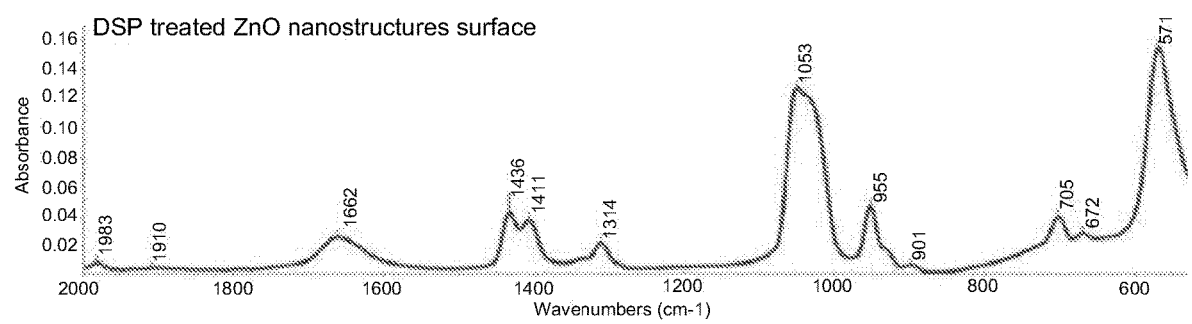
Figure 6C:
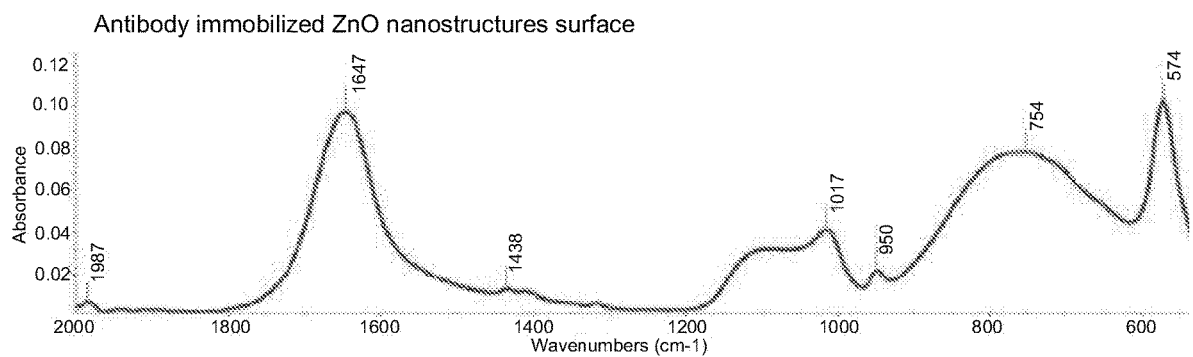

FIG. 6B is an ATR-FTIR spectra showing evidence of DSP functionalization on nanostructured ZnO sensing surface in the range between 2000 cm$^{-1}$ and 500 cm$^{-1}$. FIG. 6C is an ATR-FTIR spectra showing evidence of antibody immobilization on nanostructured ZnO sensing surface in the range between 2000 cm$^{-1}$ and 500 cm$^{-1}$. Referring to FIG. 6B, functionalization of ZnO nanostructures with linking reagent (e.g. thiol-based DSP linker molecules) can provide binding sites for immobilization of the capture reagent (e.g. antibodies). The peak at 571 cm$^{-1}$ is associated with the ZnO nanostructures and is stable as the immunoassay is being conducted on the sensing array. The peaks observed at 1053 cm$^{-1}$ and 1314 cm$^{-1}$ are assigned to stretching vibrations of $v(C-O)$ and $v(N-O)$ respectively. The spectral features $v(C-O)$ is characteristic of the ester linkage and $v(N-O)$ represents the symmetric stretch of nitro groups both of which disappears with immobilization of the antibody molecule. The other succinimidyl identifier groups that show evidence of DSP binding to ZnO surfaces are the carbonyl stretch in primary amides ($v(C=O)$) at 1662 cm$^{-1}$ and bending vibrations of alkane stretch ($v(C-H)$) with two peaks at 2915 cm$^{-1}$ and 3000 cm$^{-1}$ (not shown). Bands assigned at 1411 cm$^{-1}$ and 1436 cm$^{-1}$ are characteristic of methylene scissors deformation in the bound DSP molecule. Referring to FIG. 6C, appearance of broad band between 1200 cm$^{-1}$ and 1020 cm$^{-1}$ in the spectra is characteristic of $v(C-C, C-N)$ and confirms aminolysis of NHS groups in DSP with primary amines in antibody establishing a stable conjugation of the antibody to the linker functionalized ZnO nanostructure surfaces grown on Au working electrodes.

The ATR-FTIR spectras of the surface functionalized ZnO nanostructures (shown in FIGS. 6B and 6C) can be obtained using an FTIR spectrometer equipped with a deuterated, L-alanine doped triglycine sulfate (DLaTGS) Detector with KBr window and validation motor. The spectrometer can be fitted with a sampling stage equipped with a 600 diamond ATR crystal and the sample can be held with a swivel clamp that applied an even and constant force during the acquisition of the spectra. Each FT-IR spectrum collected on the sample represents the average of 200 scans at 4 cm$^{-1}$ resolution in the scan range of 4000-400 cm$^{-1}$.

The samples for FTIR analysis can be prepared as follows: (1) deposit a thin layer of gold (dimensions) on the glass slides followed by ZnO seed deposition; (2) clean the glass slides subsequently in acetone, isopropyl alcohol and deionized water prior to use; (3) grow the ZnO nanostructures on seeded substrates and wash with DI water to remove growth residues; (4) treat the nanostructured ZnO substrates with 10 mM DSP in DMSO for an hour; (5) after DSP functionalization, rinse the substrates with DMSO to remove unbound molecules and stored with silica desiccants for analysis. Some of the samples are washed α-cTnI antibody. After 30 minutes, the antibody treated substrates are washed with PBS and the FTIR analysis is then performed.

Referring back to FIG. 5, a plurality of capture reagents 124 may be directly or indirectly attached to the plurality of semiconducting nanostructures 122. In some embodiments, a sample comprising the target analytes 128 may be provided with a blocking buffer. The blocking buffer may comprise a protein 125 that can block or cap the binding sites of excess linking reagents that did not bind to a capture reagent. The blocking buffer can improve the signal-to-noise ratio of the sensing device. As shown in FIG. 5, a first capture reagent 124-1 may be attached to the first semiconducting nanostructures 122-1 on the first electrode 120-1, and configured to selectively bind to a first target analyte 128-1. A second capture reagent 124-2 may be attached to the second semiconducting nanostructures 122-2 on the second electrode 120-2, and configured to selectively bind to a second target analyte 128-2. In some embodiments, the semiconducting nanostructures 122-1 and 122-2 may be functionalized with a linking reagent 126, and the capture reagents 124-1 and 124-2 may be immobilized onto the semiconducting nanostructures 122-1 and 122-2 via the linking reagent 126, as described in more detail with reference to FIGS. 7A-C.

In some embodiments, a working electrode may preferably include a Au surface which offers ease of functionalization with organic linker molecules with thiol, carboxylic, etc. terminal ends. The terminal ends of the organic linker molecules bind to the Au surface through adsorption processes and are thermodynamically stable. In some embodiments, the WE may have an immersion Au surface finish which has energetically favored sites for binding of the terminal ends of the organic linker molecules in comparison to other types of thin film Au deposition methods (example: evaporation, sputtering, etc.). In other embodiments, the WE may have an immersion Ag surface, except the Ag surface tends to oxidize more easily than Au surface. A sensing WE with semiconducting ZnO, TiO$_2$, or MoS$_2$ layers can be functionalized with selective linker chemistry that subsequently conjugate with capture reagents (e.g. biomolecules, small organic molecules, etc.) required for target analyte recognition. In some embodiments, a sensing WE with semiconducting ZnO, $TiO_2$, or $MoS_2$ layers can be functionalized with non-biological chemical capture reagents, for example for the detection of certain chemicals or chemical compounds in the sample.

The selection of linker molecules can be influenced by several factors including bond-stability, position of functional groups, pH, presence/absence of amine groups for interaction with antibody, surface charge etc. The availability of different functional groups in linker molecules can enable the immobilization of antibody through stable covalent linkage, and the antibody-antigen interactions provide specificity for detection of target analytes. In the embodiments described herein, binding of capture reagents and subsequent biomolecules to the affinity immunoassay leads to changes in the ion diffusion profile near the nanostructures and hence changes in electrical properties (capacitance, resistance, etc.). The electrochemical detection methods described herein include means to directly characterize the capture reagent—target analyte interactions based on charge perturbations at the electrode-electrolyte interface. In some embodiments, functionalization may include the use of thiol and phosphonic acid terminated groups on ZnO nanostructures or thin films.

Figure 7A:
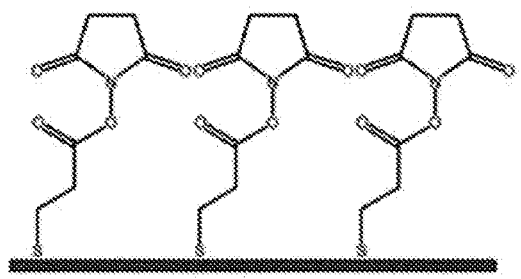
FIGS. 7A-7D show the functionalization of a working electrode in accordance with some embodiments.
Figure 7B:
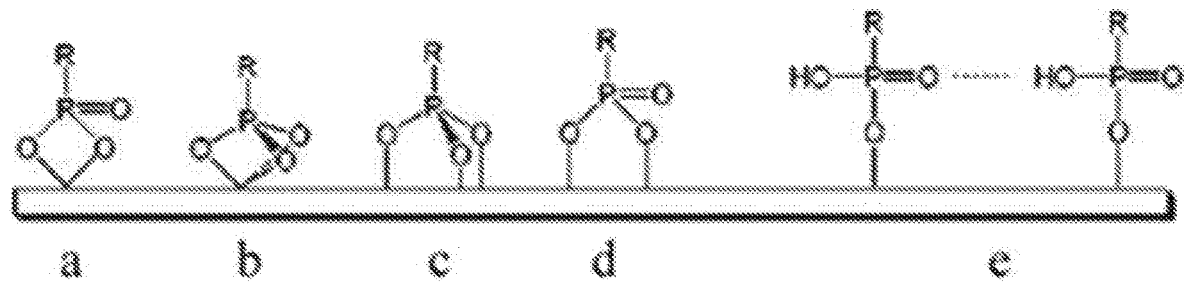
Figure 7C:
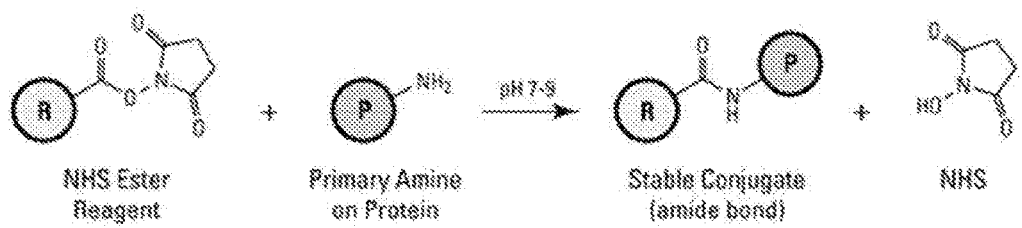
Figure 7D:
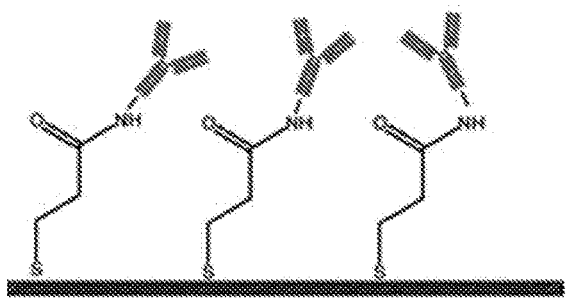

FIG. 7A shows the functionalization of a sensing WE using the linker molecule dithiobis(succinimidyl propionate) (DSP) in accordance with an embodiment. The DSP contains an amine-reactive N-hydroxysuccinimide (NHS) ester at each end of an 8-carbon spacer arm containing a cleavable disulfide bond. The DSP reacts with the Au surface to form stable Au-thiol bonds from which the amine-reactive NHS ester extend. The NHS esters react with primary amines at pH 7-9 to form stable amide bonds, along with release of the N-hydroxy-succinimide leaving group. Proteins, including antibodies, generally have several primary amines in the side chain of lysine (K) residues and the N-terminus of each polypeptide that are available as targets for NHS-ester crosslinking reagents. FIG. 7B shows the functionalization of a sensing WE using phosphoric based organic linker molecules in accordance with another embodiment, that can form stable Au-phoshonic bonds represented by bond configurations a-e. Capture reagents (e.g., biomolecules) can include proteins, small molecules, antibodies, nucleic acids, etc., and can be customized for the binding and detection of specific target analytes of interest. The process of immobilizing the capture reagents on the functionalized sensing WE surfaces and the subsequent detection of biomarkers may be described as an assay. FIG. 7C shows a schematic reaction for amine-reactive NHS ester reagents with primary amines on a protein at pH 7-9 to form stable amide bonds, along with release of the N-hydroxy-succinimide leaving group. Proteins, including antibodies, generally have several primary amines in the side chain of lysine (K) residues and the N-terminus of each polypeptide that are available as targets for NHS-ester crosslinking reagents. FIG. 7D illustrates a DSP functionalized sensing WE surface forming stable amide bonds with the primary amine groups of a selected antibody of interest.

Accordingly, the multi-configurable sensing array described herein may comprise sensing working electrodes that can be independently functionalized with the appropriate linker chemistry and different capture reagents that are specific to the detection of different target analytes. Affinity-based sensors/sensing can leverage the above functionalization strategies. In catalytic-based sensors/sensing, binding of catalysts to the electrode surfaces can ensure that the chemical reaction and electron transfer occur in proximity to the electrode surfaces.

A. Multiplexer and Sensing Circuitry

Referring back to FIG. 5, the sensing system 500 may further comprise a multiplexer 150, sensing circuitry 160, and computing device 170. The array 400 may be electrically connected to the multiplexer 150 and the sensing circuitry 160. The multiplexer may comprise a plurality of channels 152 for multiplexing electrical signals received from the array. The first sensing device 100-1 may be connected to a first channel 152-1 and the second sensing device 100-2 may be connected to a second channel 152-2. Referring to FIG. 5, the first WE 120-1, CE 140-1, and RE 130 may be connected to the first channel 152-1. The second WE 120-2, CE 140-2, and RE 130 may be connected to the second channel 152-2. The multiplexer 150 may be in two-way communication with the sensing circuitry 160. For example, the sensing circuitry can be configured to apply modulation signals to the array via the multiplexer. Output signals from the first and second channels may be transmitted to the sensing circuitry for simultaneous and multiplexed detection of the different target analytes present in the fluid sample.

The sensing circuitry 160 can be configured to take electrochemical measurements. In some embodiments, the sensing circuitry may comprise a potentiostat. The sensing circuitry may be capable of signal generation and signal conditioning. In some embodiments, the sensing circuitry may include converters such as analog-to-digital converters (ADC) and digital-to-analog converters (DAC). The sensing circuitry 160 can be configured to selectively apply a plurality of modulation signals to the two sensing devices 100-1 and 100-2 to enable detection of the plurality of different target analytes in the fluid sample. The sensing circuitry can be configured to individually and selectively control, activate, or modulate the two sensing devices. The plurality of modulation signals can be configured to aid in enhancing detection sensitivity of the different target analytes. The sensing arrays described herein can include any number of electrodes (e.g. working electrodes, counter electrodes, and reference electrodes) in various types of configurations. The sensing circuitry can be configured to individually and selectively control, activate, or modulate any number of sensing devices by applying different signals to the electrodes, for example as shown by the electrical field simulations in FIGS. 17A-17F.

As previously described, the first and second sensing devices 100-1 and 100-2 may comprise different capture reagents 124-1 and 124-2 that are configured to selectively bind to different target analytes 128-1 and 128-2 in a fluid sample. The selective binding is configured to effect changes to electron and ion mobility and charge accumulation in different regions of the semiconducting nanostructures 122-1 and 122-2 and the fluid sample. Each of the sensing devices can be configured to determine a presence and concentration of a different target analyte in the fluid sample based on detected changes to the electron and ion mobility and charge accumulation.

The sensing circuity 160 can be configured for simultaneous acquisition and multiplexing of electrical signals from the sensing devices 100-1 and 100-2. The sensing circuitry is configured to analyze the electrical signals comprising of impedance and capacitance signals. The signals may be indicative of interfacial charge modulation comprising of the changes to the electron and ion mobility. The signals may include capacitance changes to space-charge regions formed in the semiconducting nanostructures upon binding of the different target analytes to the corresponding capture reagents. The changes may comprise simultaneous modulation to the ion mobility in one or more regions adjacent to the semiconducting nanostructures.

The sensing circuitry 160 can be configured to implement a plurality of electrochemical detection techniques for detecting the impedance changes and the capacitance changes. In some embodiments, the plurality of electrochemical detection techniques may comprise a modified EIS technique for measuring the impedance changes and Mott-Schottky technique for measuring the capacitance changes. The modified EIS technique is capable of distinguishing the electrical impedance signals from background noise at low concentrations of the different target analytes in the fluid sample.

The array 400 is capable of simultaneous and multiplexed detection of the different target analytes present in the fluid sample using the plurality of electrochemical detection techniques with aid of the sensing circuitry 160. The sensing circuitry 160 can be configured to perform the simultaneous and multiplexed detection by analyzing the electrical impedance and capacitance signals to determine the presence and concentration of each of the different target analytes. The sensing circuitry can be configured to perform the simultaneous and multiplexed detection substantially in real-time upon binding of the different target analytes to the corresponding capture reagents on the semiconducting nanostructures. The sensing circuitry can be configured to analyze the impedance and capacitance signals by concurrently analyzing a set of Nyquist plots obtained via the modified EIS technique and a set of Mott-Schottky plots obtained via the Mott-Schottky technique.

In some embodiments, the modified EIS technique may comprise (1) sectioning an interfacial charge layer for each of the two or more sensing devices into a plurality of spatial dielectric z-planes along a direction orthogonal to the interface between the fluid sample and the semiconducting nanostructures, and (2) probing each of the plurality of z-planes with a specific frequency selected from a range of frequencies. Specific binding of different target analytes to the corresponding capture reagents may occur at known spatial heights within the plurality of interfacial charge layers for the two or more sensing devices. The sensing circuitry can be configured to determine the presence and concentration of each of the different target analytes by measuring the capacitance and impedance changes at specific frequencies corresponding to their respective z-planes.

In some embodiments, the sensing circuitry 160 may be connected to a computing device 170. The sensing circuitry may or may not be part of the computing device. The computing device may be configured to process and/or display results obtained via the above-described electrochemical detection techniques. For example, the computing device can be configured to display an electrochemical signal response 180 which may include a set of Nyquist plots obtained via the modified EIS technique and/or a set of Mott-Schottky plots obtained via the Mott-Schottky technique. In some embodiments, the electrochemical signal response may be displayed on the computing device 170 for further analysis or data manipulation by a user.

In some embodiments, the first target analyte 128-1 may be cTnI antigen, and the first capture reagent 124-1 may be an antibody that is specific to the cTnI antigen. The second target analyte 128-2 may be cTnT antigen, and the second capture reagent 124-2 may be an antibody that is specific to the cTnT antigen. The semiconducting nanostructures 122-1 and 122-2 on the WEs 120-1 and 120-2 may comprise ZnO nanostructures. The linker reagent 126 may comprise a DSP linker. The surfaces of the ZnO nanostructures may be functionalized with the DSP linker for attaching the antibodies to the nanostructures. Accordingly, the first and second sensing devices can be used for electrochemical detection of the different cardiac biomarker Troponin isoforms cTnI and cTnT. Baseline electrical characterization of the array of sensing devices can be verified based on an electrochemical impedance response at a predefined frequency (e.g., 100 Hz). The detection of cTnI and cTnT in the sample can be achieved using the modified EIS and Mott-Schottky techniques described as follows.

B. Modified EIS

In a conventional EIS technique, impedance changes occurring at the electrode-electrolyte solution interface can be identified and quantified. However, the challenge in using conventional EIS for protein detection has been the inability to distinguish the impedance signal from background noise as the concentration of the target protein diminishes in the complex test solutions such as human serum.

In the modified EIS technique described in various embodiments herein, a small AC voltage (for example <100 mV peak-to-peak) can be applied over a range of frequencies (e.g. from 1 Hz to 15 KHz) across the sensing electrodes (WEs) of a sensing device or an array of sensing devices. In the presence of a fluid on the sensing surface, an electrical double layer (EDL) is formed at the sensing electrode/fluid interface. The capacitive impedance of the EDL reflects the composition of the ions/biomolecules/interferents present at the interface. In conventional EIS, the total capacitive impedance of the EDL is measured and hence it is not possible to distinguish the signal from specific binding events and non-specific interactions, especially when the concentration of the target materials or analytes is very low as compared to the interferent material.

In the modified EIS technique disclosed herein, the EDL can be sectioned along the z-direction, i.e. in the orthogonal direction to the sensing electrode-electrolyte solution interface with subnanometer precision. Each spatial z-plane within the electrical double layer can be probed with a specific frequency. Since the specific binding of the protein with an immobilized antibody capture probe is expected to occur at a known spatial height within the EDL, protein binding even at ultra-low concentrations can be extracted with precision and accuracy by measuring the capacitive impedance changes at a specific frequency corresponding to the z plane in which the protein binding event occurs. The modified EIS technique disclosed herein is advantageous in that resolution is not diminished in the presence of complex media with high concentrations of interferent material.

In the modified EIS technique, the EDL at the sensing electrode/electrolyte buffer interface can be fragmented and analyzed at varying heights from the interface by measuring the impedance response at multiple frequency planes. Specific interactions between a target protein and its specific antibody capture probe can be selectively identified through a maximal change to the measured impedance at a specific frequency which maps to the height from the interface where antibody-target analyte binding happens. The use of the modified EIS technique can enhance specificity of detection. The use of ZnO can aid in achieving heightened sensitivity by leveraging the ionic and semiconducting nature of the semiconducting material. Also, the use of ZnO nanostructures can enhance signal response as a result of biomolecule confinement.

Figure 8A:
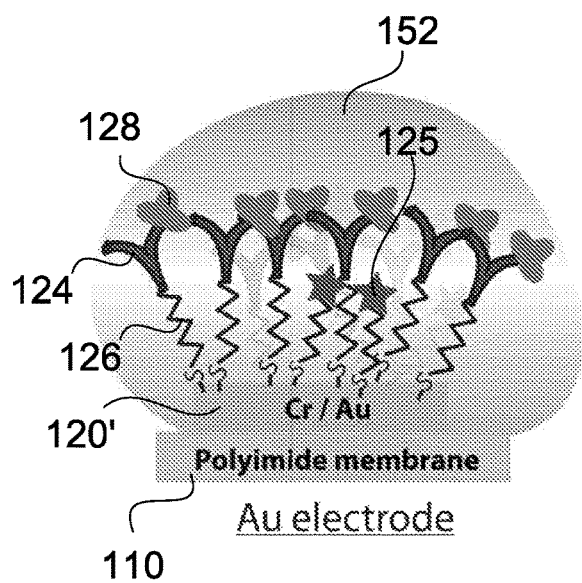
FIGS. 8A-8D show fluid sample absorption onto different working electrodes and z-plane fragmentation using a modified EIS technique.

FIG. 8A illustrates fluid sample absorption onto a working electrode (WE) 120' disposed on a substrate 110. The substrate may comprise a polyimide membrane. The WE 120' may be a Au electrode having a Cr/Au surface finish.

Figure 8B:
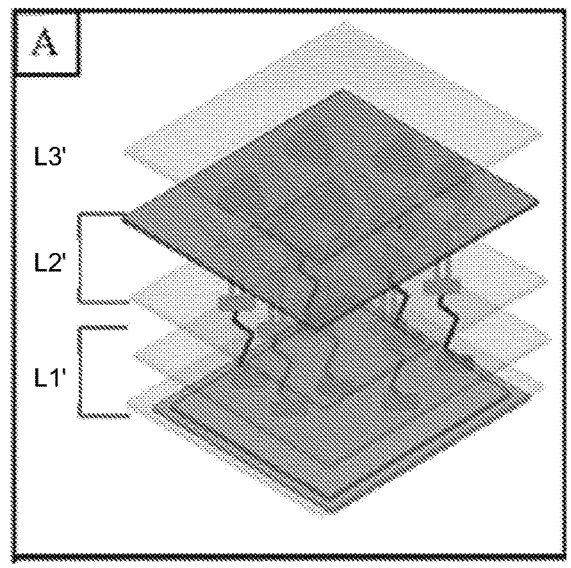

The WE 120' may be substantially planar. The WE 120' may be directly functionalized with a linker 126 that selectively immobilizes a capture reagent 124 (e.g., an antibody) that is specific for a target analyte 128 (e.g., an antigen). In some embodiments, a blocking reagent 125 may be optionally included to block excess binding sites on linker 126. A sample 152 comprising target analytes 128 may be introduced to the sensing device/array and adsorbed on the WE 120'. FIG. 8B illustrates z-plane fragmentation using a modified EIS technique on a plurality of Helmholtz planes at the planar sensor surfaces of FIG. 8A. Levels L1', L2' and L3' as shown may correspond to different spatial z-planes which can be probed using logarithmic frequency scanning (e.g. ranging from 1 Hz-15 kHz).

Figure 8C:
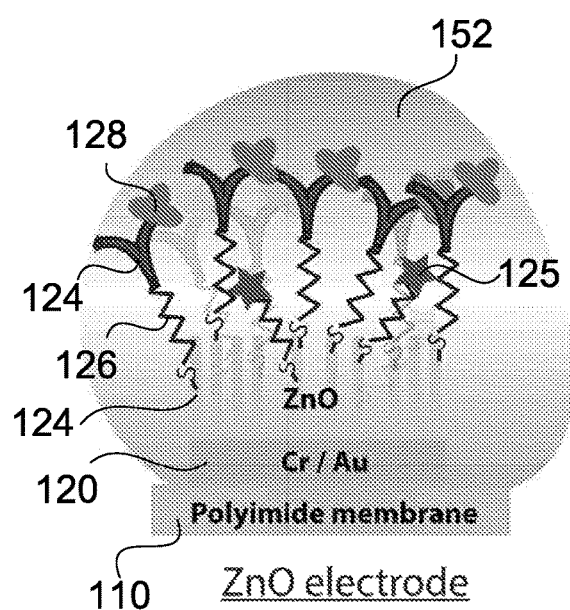
Figure 8D:
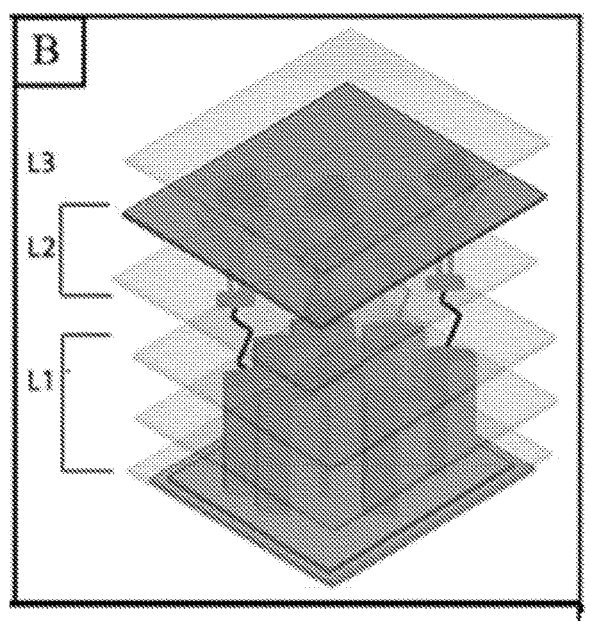

FIG. 8C illustrates fluid sample absorption onto a working electrode (WE) 120 comprising semiconducting ZnO nanostructures 122 disposed on a substrate 110. The WE 120 may functionalized with the linker 126 that selectively immobilizes a capture reagent 124 (e.g., an antibody) that is specific for a target analyte 128 (e.g., an antigen). In some embodiments, a blocking reagent 125 may be optionally included to block excess binding sites on linker 126. A sample 152 comprising target analytes 128 may be introduced to the sensing device/array and adsorbed on the WE 120. FIG. 8D illustrates z-plane fragmentation using a modified EIS technique on a plurality of Helmholtz planes at the EDL interface at the nanostructured sensor surfaces of FIG. 8C. Levels L1, L2 and L3 as shown may correspond to different spatial z-planes which can be probed using logarithmic frequency scanning (e.g. ranging from 1 Hz-15 kHz).

Comparing FIGS. 8B and 8D, it can be observed that the height L1 of the semiconducting ZnO nanostructures is greater than the height L1' of the planar Au electrode layer. Accordingly, the semiconducting ZnO nanostructures can increase the z-height or profile of the working electrode which is advantageous. For example, since the specific binding of a target analyte with an immobilized capture reagent is expected to occur at a known spatial height within the EDL, binding events at ultra-low concentrations can be extracted with precision and accuracy by measuring the capacitive impedance changes at a specific frequency corresponding to the z plane in which the protein binding event occurs. By probing the impedance over a larger L1' plane, the modified EIS technique can maintain its resolution in the presence of complex media with a high concentration of interfering material.

The modified EIS technique can be used to fragment the EDL along the z direction with subnanometer precision by changing the frequency of measured response for stepwise changes to the applied potential within the electrochemical window of the ionic liquid (IL)/electrolyte. Recognition and detection of specific binding events for different protein biomarkers (e.g. cTn, NT-pro BNP, and CRP) in a multiplexed manner can be achieved as a result of dielectric permittivity modulation along the frequency spectrum due to the zwitterion stabilization effect of the ionic liquids in the EDL at the IL/ZnO electrode buffer interface. Bode analysis with collected impedance spectra can be used to identify the frequency range at which capacitive behavior is dominant. The identified frequency range in performing a Nyquist analysis can be used to quantify the effect of charge transfer for varying concentrations of a target biomolecule. Thus the ZnO surfaces can enhance biomolecule detection. The maximum impedance change from different assay steps can be used to design the calibration dose response curve to correlate the concentration of bound target biomolecules and the measured changes in impedance.

C. Simulation and Design

FIG. 9A shows a 2D schematic geometric model of the sensing array of FIG. 4 in COMSOL domain with applied boundary conditions. COSMOL Multiphysics is a finite element software that can be used to virtually simulate the real-time behavior of the sensing array to determine its performance. The simulation results can be used to optimize the design of the multiplexed sensing array to meet certain desired characteristics. The use of simulations can also help to reduce fabrication cost and time.

The COSMOL model encompasses the multi-electrode geometry constructed in three dimensional space. Simulations are performed using an AC/DC module with assumption of no magnetic field effects to establish that the first and second sensing devices of the array have the same baseline electrical performance. The geometric structures of each sensing device comprise three microelectrodes (WE, CE, and RE) built on polyimide substrate and surrounded by a rectangle made of PBS. Electrical properties of gold are assigned to both the counter electrodes (CEs) and the reference electrode (RE). The working electrodes (WEs) are assigned the semiconducting properties of ZnO. A constant applied potential of 10 mV is set at the WE. The boundary condition of both the RE and the CEs is set at zero potential. Electrical insulation with a von Neumann boundary condition (n.J=0) is applied to the PBS layer. The transient electric field is assumed to be confined within the multiplexed electrodes and the surrounding PBS medium and is governed by the following continuity equation.

$$\nabla \cdot J = Q_j \text{ i.e. } \nabla \cdot \sigma E = -\frac{\partial \rho}{\partial t}$$

where σ is the charge density. Based on Ohm's law, a relation between the current density, J (vector quantity) and the electric potential, V (scalar quantity) can be established. The electric field E, can be obtained from the following constitutive relation and the gradient of the scalar potential V as shown.

$$D = \varepsilon_o \varepsilon_r E$$

$$E = -\nabla V$$

In the above equations, D is the displacement current, $\varepsilon_o$ is the permittivity of free space and $\varepsilon_r$ is the relative permittivity of the material/electrolyte used. The discretization of the system into finite elements is based on physics-controlled mesh generation.

FIG. 9B shows the current distribution in the multiplexed sensing array for simulations performed with the above-described boundary conditions. The surface plot shows uniform distribution of current density between the electrodes of the sensing array. Maximum current density is observed near the surface of WEs which indicates that the output current response measured using a modified EIS technique is from the WEs. The direction of the white arrows corroborates that the electric field lines are directed away from the positive surface and that the performed simulations are correct.

FIG. 9C shows the variation in measured current density with distance between WE and CE in the sensing array along the vertical dotted lines depicted in FIG. 9A. FIG. 9D shows the variation in measured current density with distance between WE and RE in the sensing array along the horizontal dotted line depicted in FIG. 9A. The results indicate that both WEs exhibit the same performance along their surfaces and in each three electrode setup. For points that are measured farther away from the WE, current density decreases and with a highest value of $1.7 \times 10^{15}$ A/m$^2$ observed at its surface. The simulation results indicate that both WEs exhibit the same baseline electrical performance under ideal conditions, and thus placement of the electrodes in the multiplexed sensing array has minimal to no variation. Surface modification of the WEs can perturb the charge distribution at the electrode/electrolyte interface. These perturbations are based on realignment of electrons or holes in the electrode surface and ions in the electrolyte solution. Thus, these charge perturbations can be leveraged towards designing the sensing devices/array described herein for multiplexed detection of multiple biomarkers.

D. Baseline Characterization

Figure 10A:
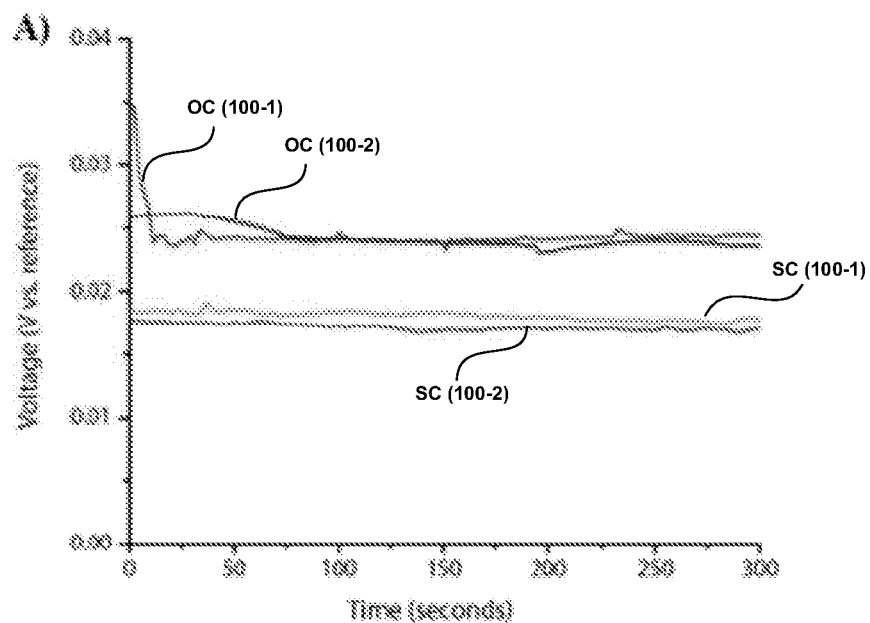
FIGS. 10A and 10B show the baseline electrochemical response of the sensing array of FIG. 5, and the impedance response at each step of the immunoassay.

FIG. 10A shows the baseline electrochemical response of a multiplexed sensing array characterized in the presence of a supporting electrolyte—PBS at 10 mV peak-to-peak at 100 Hz. The open circuit (OC) potential at both the first and second sensing devices is measured to establish that the same electric potential exists on both sensing devices of the array. This corresponds to the potential experienced at the working electrode relative to the reference electrode prior to occurrence of an electrochemical reaction, and is estimated at 0.02 V, i.e. 25.0±1.8 mV in the first sensing device and 24.6±1.6 mV in the second sensing device. Similarly, the short circuit (SC) potential is measured in presence of PBS and was observed at 0.01 V, i.e. 18.2±0.8 mV in the first sensing device, and 17.2±0.5 mV in the second sensing device.

Figure 10B:
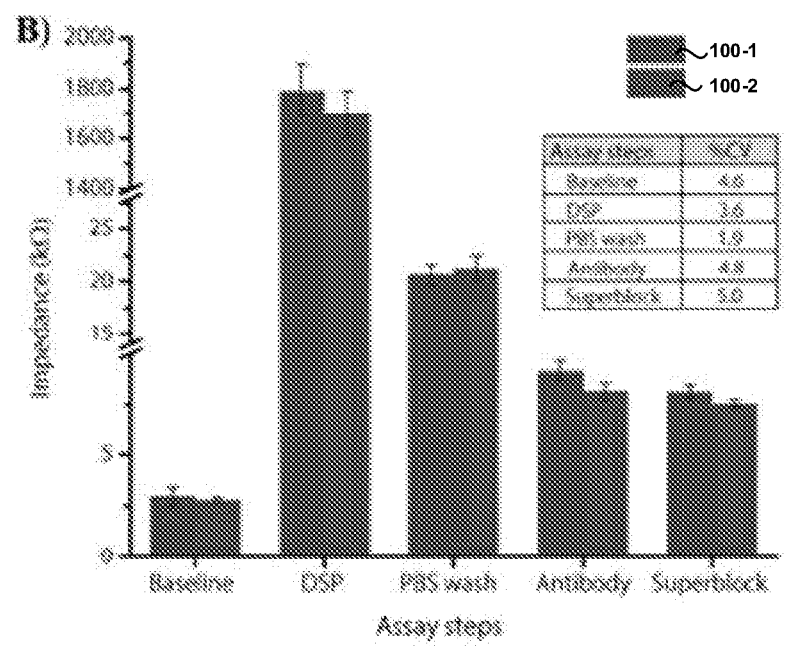

FIG. 10B shows the impedance response at each step of immunoassay for both the first and second sensing devices of the array. Upon functionalization of ZnO surfaces with DSP, the thiol functional group in DSP binds to the Zn sites in the nanostructures forming Zn—S bond. The charged working electrodes in the presence of an ionic buffer medium experience alignment of charges at the electrode surface forming an electrical double layer (EDL). A modified Randles equivalent circuit can be used to study the contribution due to capacitive and resistive elements. The charge conduction between the working electrode and the ionic buffer constitute the charge transfer resistance ($R_{ct}$), and the resistance offered by the buffer constitutes the solution resistance ($R_s$) in the electrochemical signal response. The amine reactive 8-carbon spacer molecule in DSP is highly resistive and hence higher impedance response is obtained. The impedance for the DSP step is increased from baseline impedance of 2 kΩ to 1792 kΩ in the first sensing device, and 2.7 kΩ to 1701 kΩ in the second sensing device. The difference in impedance between the first and second sensing devices can be attributed to density of functionalization and is within the acceptable coefficient of variation (CV) for electrical sensing arrays (for example, CV<10%). In some cases, the CV may be 9%, 8%, 7%, 6%, 5%, or less.

Prior to functionalization, the working electrodes comprising ZnO nanostructures can be prepared for antibody immobilization by performing a 3× wash with DMSO followed by 3×PBS wash. A decrease in impedance observed with PBS wash post functionalization may be due to the conducting molecules that are present in the buffer. For these characterization studies, cTnT is used to establish consistency in electrical performance between the first sensing device and the second sensing device during the immunoassay steps. When antibody (α-cTnT) is immobilized, the charges in the outer plane realign and this arrangement is analogous to that of a parallel plate capacitor that constitute double layer capacitance ($C_{dl}$). The impedance response at the first sensing device and the second sensing device decreased to 9.1 kΩ and 8.1 kΩ respectively due to binding of α-cTnT to linker molecule. Post wash step with PBS, the multiplexed sensing array is treated with a blocking buffer containing a blocking reagent (e.g. 125) to block any unbound DSP sites, and the measured impedance is 8.1 kΩ and 7.5 kΩ respectively at the first sensing device and the second sensing device. The order of testing the first and second sensing devices did not affect the impedance responses of the multiplexed sensing array. The sensing array is then washed with PBS to prepare it for performing antigen dose response studies. The noise in the sensing array is estimated as a change in output signal response between pre- and post-buffer wash after a superblock step. The recommendation for signal noise threshold for any electrical sensing array is usually 3 times the noise, and noise estimation for both electrochemical detection techniques is described elsewhere herein.

Immunoassays for cTnI detection can be performed at the first sensing device and that for cTnT detection can be performed at the second sensing device using the array shown in FIG. 5, for establishing multiplexed and simultaneous detection of cTnI and cTnT. The sensing array preparation for detection of these cardiac biomarkers may comprise of the immunoassay steps described elsewhere herein. The prepared sensing array is first tested with neat human serum (HS) which consists of zero concentration of measured protein biomarker to establish zero dose measurement. This is used to characterize signal change as a function of antigen binding to antibody immobilized surfaces. Different concentrations of cTnI antigen starting with the lowest concentration on α-cTnI immobilized ZnO nanostructure surface can be tested at the first sensing device. Similarly, different doses of cTnT antigen can be tested on α-cTnT immobilized ZnO nanostructure surface at the second sensing device. The change in output signal response for subsequent doses is calculated from zero dose measurement to obtain a calibration curve for cTnI and cTnT detection. The percentage change in measured signal is used to represent the multiplexed sensing array performance. Detection of cTnI and cTnT can be achieved using both the modified EIS technique and Mott-Schottky technique described herein.

E. Electrochemical Signal Responses

FIGS. 11A and 11B show Nyquist plots representing the detection of cTnI and cTnT using the multiplexed sensing array of FIG. 5. The Nyquist plots can be obtained via the modified EIS technique described herein. A decrease in capacitive impedance is observed with increasing concentration of tested protein biomarker as shown in the Nyquist plots. Analysis of corresponding Bode phase plots reveals the lag in output signal response (59° for cTnI detection and 62° for cTnT detection) which corroborates the maximum contribution to output signal response is dominated by capacitance at the double layer, $C_{dl}$. With increasing concentrations of tested biomarker binding to antibody immobilized ZnO surfaces, the charge distribution at EDL is perturbed resulting in a dominating capacitive impedance observed at 100 Hz.

FIGS. 11C and 11D show calibration curves representing the detection of cTnI and cTnT using the multiplexed sensing array of FIG. 5. Similarly, the calibration curves can be obtained via the modified EIS technique described herein. The linear response of detection for cTnI and cTnT is across the tested concentration ranges 0.1 pg/mL to 1E5 pg/mL. A dynamic change of 58% for cTnI detection resulting from impedance range is observed between 4.7 kΩ and 1.9 kΩ.

Similarly, the range of impedance observed for cTnT detection is between 5.8 kΩ and 2.2. kΩ resulting in dynamic range of 61% for cTnT detection. The signal noise threshold is calculated as three times the change in impedance response between pre- and post-buffer wash post blocking step in immunoassay. The observed signal noise threshold for cTnI detection at the first sensing device is 8.8% and for cTnT detection at the second sensing device is 7.4%. In some embodiments, the lowest concentration that can reliably be detected using the multiplexed sensing array is evaluated to be 1 pg/mL for cTnI detection and 0.1 pg/mL for cTnT detection.

Figure 12A:
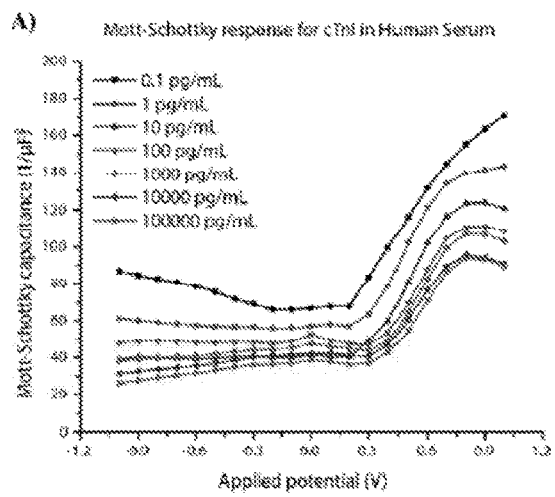
FIGS. 12A-12D show Mott-Schottky capacitance and calibration curves plotted as a function of applied potential for cTnI and cTnT detection using the sensing array of FIG. 5.
Figure 12B:
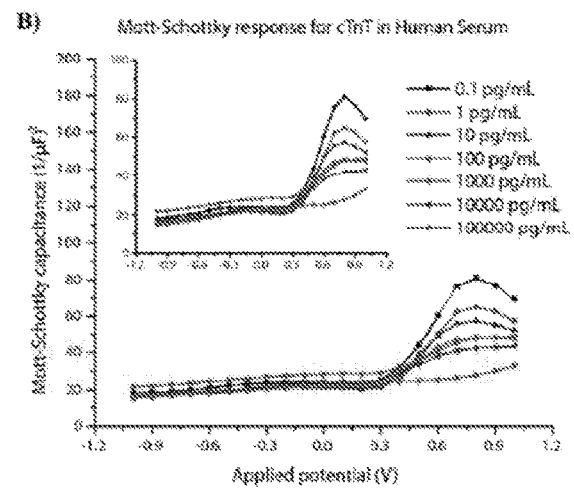

FIGS. 12A and 12B show Mott-Schottky capacitance ($1/C^2$) plotted as a function of applied potential for cTnI and cTnT detection using the multiplexed sensing array of FIG. 5. The Mott-Schottky plots are obtained with a voltage sweep of −1 V to +1V and input signal amplitude of 10 mV peak-to-peak at 1000 Hz. A smaller change in capacitance ($1/C^2$) with increasing concentrations of tested doses of cardiac biomarker is obtained. FIG. 12A shows linear increase in $1/C^2$ at potentials higher than 0.3 V for cTnI detection which is as expected for an n-type ZnO. At applied potential higher than 0.7 V, the response $1/C^2$ reaches its limiting value and hence 0.7 V is chosen to represent change in $1/C^2$ with cTnI antigen binding. A similar response is observed for cTnT detection as shown in FIG. 12B. The range of $1/C^2$ obtained is between 144.8 and 86.4 $(1/F)^2$ for cTnI whereas for cTnT detection, $1/C^2$ values obtained is in the lower range from 76.12 to 26.38 $(1/F)^2$ with increasing concentrations of tested dose. The trend from the Mott-Schottky plots is consistent with the Nyquist plots obtained via the modified EIS technique.

Figure 12C:
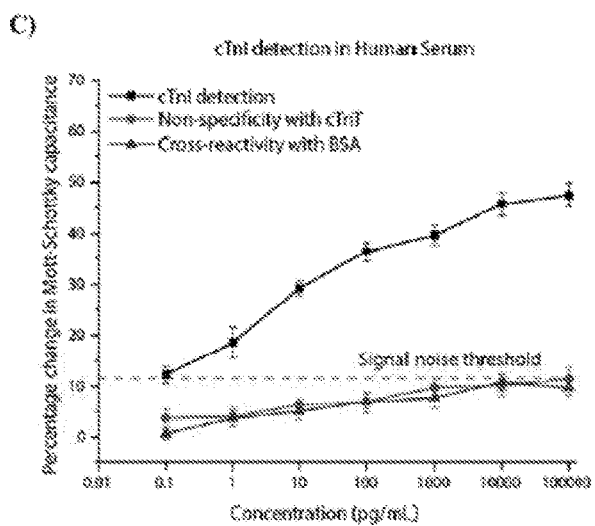
Figure 12D:
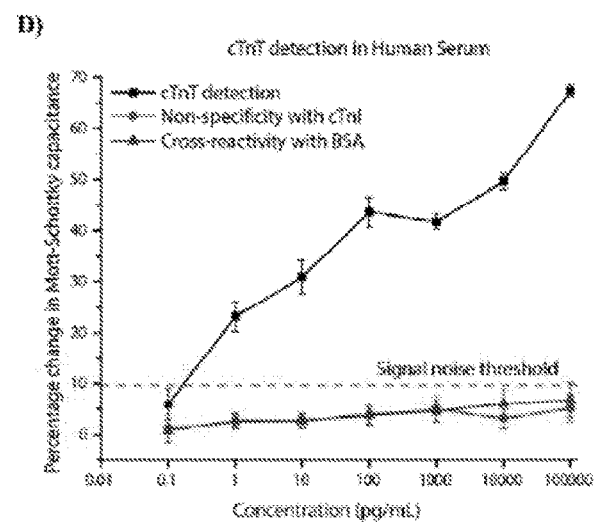

FIGS. 12C and 12D show calibration curves representing the percentage change in Mott-Schottky capacitance with varying concentrations of cTNI and cTnT. FIG. 12C shows the calibration curve for cTnI with 47% dynamic change in output response. The signal noise threshold is estimated at 11.5% and hence the reliably detected lowest concentration of cTnI with MS is 1 pg/mL. Similarly, the calibration curve for cTnT detection is shown in FIG. 12D. The dynamic change of 67% is obtained with detectable lowest cTnT concentration at 1 pg/mL. The estimated noise threshold for cTnT array is 9.2%. It is noted that the slightly higher signal noise threshold on the Mott-Schottky capacitances relative to that of the modified EIS plots may be due to the microelectrode layout. An analysis of the Mott-Schottky plots shows donor densities of $10^{22}$ cm$^{-3}$ for the semiconducting ZnO nanostructures.

The sensing devices and arrays described herein are capable of detecting a target isoform of protein biomarkers in the presence of other similar protein biomarkers. In some embodiments described herein, the non-specificity of α-cTnT for cTnI isoform and α-cTnI for cTnT isoform is tested over the range of concentrations between 0.1 pg/mL and 1E5 pg/mL. The electrochemical signal responses in FIGS. 11C, 11D, 12C, and 12D indicate that only the corresponding target isoform shows a decrease in capacitive impedance (i.e. increase in percentage change in EIS impedance and Mott-Schottky capacitance) with increasing dose concentration, while the signal response due to the non-specific isoform is well within the established signal noise threshold. The non-specificity of α-cTnI and α-cTnT for alternating isoforms with the modified EIS is shown in FIGS. 11C and 11D respectively, and with Mott-Schottky in FIGS. 12C and 12D, respectively. In addition to target protein biomarkers, a test sample may further comprise a range of different biomolecules and therefore there exists a probability for the capture reagents to interact with those biomolecules and interfere in the detection of the target protein. This cross-reactivity for α-cTnI and α-cTnT is tested on a multiplexed sensing array with BSA using varying concentrations diluted in HS in absence of protein biomarkers. BSA is chosen, as albumin is the main protein in human blood plasma. The measured EIS response is shown in FIGS. 11C and 11D, and the measured Mott-Schottky capacitance response is shown in FIGS. 12C and 12D, respectively. The maximum percentage change in impedance observed with BSA using the modified EIS is 5.8% and 5.5% respectively with α-cTnI and α-cTnT immobilized ZnO nanostructured sensing surfaces and is well within the established signal noise threshold. The maximum percentage change in capacitance observed with BSA using Mott-Schottky is 10% and 7% respectively with α-cTnI and α-cTnT immobilized ZnO nanostructured sensing surfaces. Although the Mott-Schottky for BSA shows relatively high signal response, it is still within the established signal noise threshold. Thus, the multiplexed sensing array having ZnO nanostructures demonstrates good specificity and satisfactory level of cross-reactivity for target cardiac biomarkers. The above also demonstrates the feasibility of detection in complex biological medium with both the modified EIS and Mott-Schottky techniques.

Figure 13A:
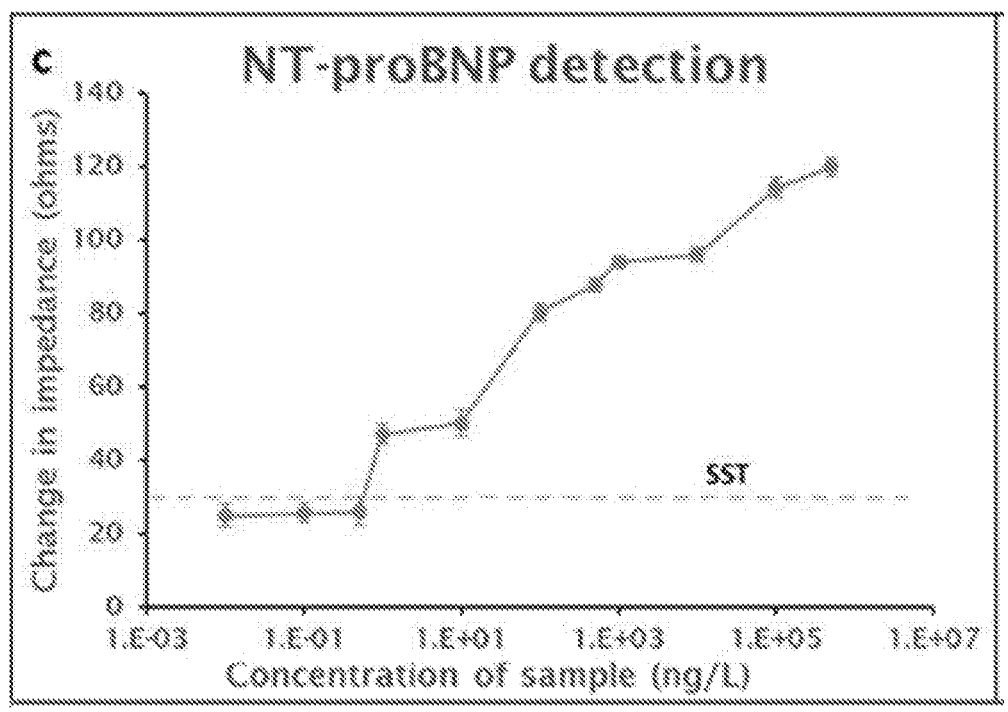
FIG. 13A shows a calibration curve representing the detection of NT-proBNP using the sensing array of FIG. 5.
Figure 13B:
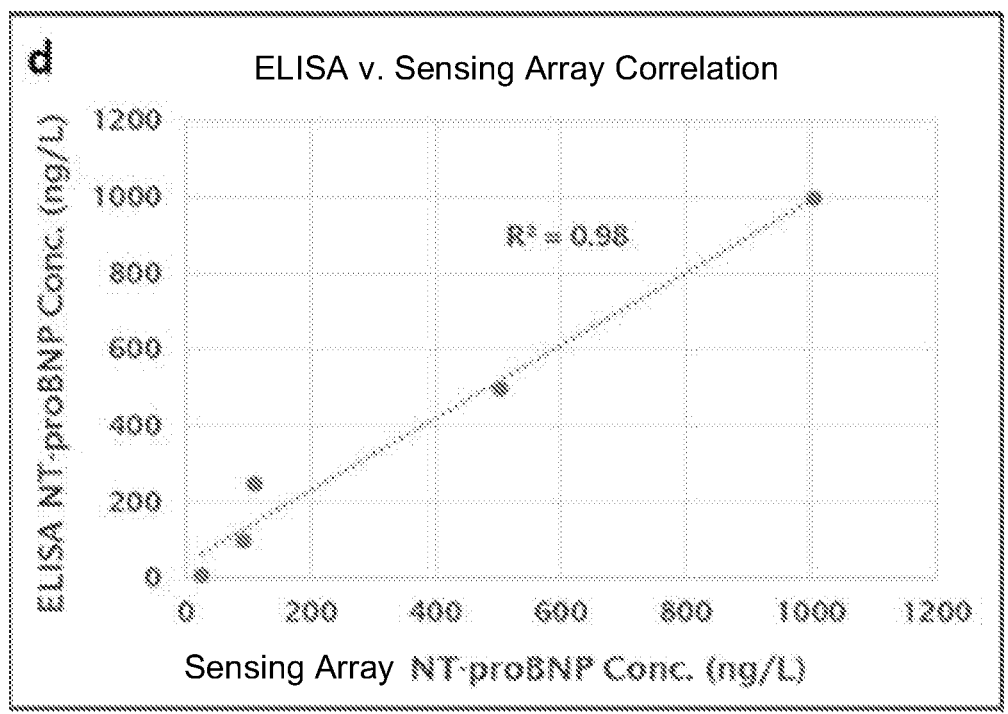
FIG. 13B shows the correlation between NT-proBNP detection using an exemplary sensing array and NT-proBNP detection using a conventional enzyme-linked immunosorbent assay (ELISA)

FIG. 13A shows a calibration curve representing the detection of NT-proBNP using the multiplexed sensing array of FIG. 5. The calibration curve can be obtained via the modified EIS technique described herein. The linear response of detection for NT-proBNP is across the tested concentration ranges 0.1 ng/L to 1E5 ng/L. The range of impedance observed for NT-proBNP detection is between 30Ω and 120 kΩ resulting in dynamic range of 75% for NT-proBNP detection. The signal noise threshold is calculated as three times the change in impedance response between pre- and post-buffer wash post blocking step in immunoassay. The observed signal noise threshold for NT-proBNP detection is at 30%. In some embodiments, the lowest concentration that can reliably be detected using the multiplexed sensing array is evaluated to be 1 ng/L for NT-proBNP detection. FIG. 13B shows a strong correlation between NT-proBNP detection using the exemplary sensing array described herein and NT-proBNP detection using a conventional enzyme-linked immunosorbent assay (ELISA). As shown in FIG. 13B, the $R^2$ value is 0.98 over a tested range from 1ng/L to 1000 ng/L.

V. Sensing Platforms

A. Diagnostics Reader Device

Physicians currently use a combination of imaging and laboratory analysis for disease diagnosis in a clinical setting. Samples from patients can be tested for a multitude of biomolecular markers. This type of analysis, while precise and repeatable, requires significant processing time and hence not applicable for POC diagnostics. The development of successful sensing device for POC disease diagnostics relies on four major attributes: rapid detection, sensitivity of detection, specificity of detection, and ease of use. The incorporation of these key features can allow clinicians to efficiently provide the necessary feedback and care to their patients regarding diagnosis, prognosis and response to therapy. However, current handheld POC devices for cardiac biomarkers often lack the ability to provide diagnostics in real-time and with high accuracy and consistency at patient bedside outside the ED and hospital environment such as primary care, assisted/independent living care, and ambulatory environments.

Figure 14:
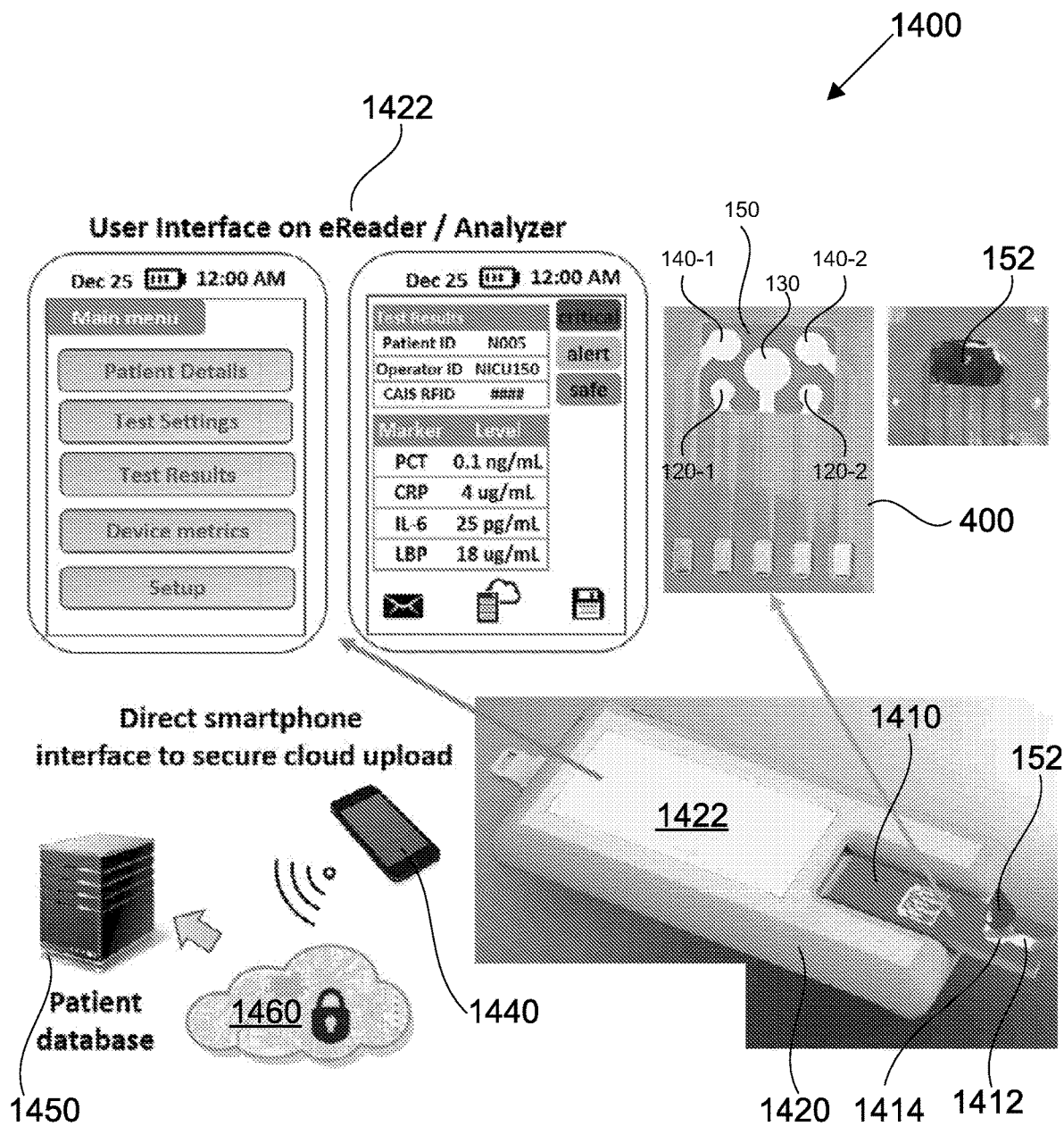
FIG. 14 shows a sensing platform comprising a test strip and a diagnostic reader device, in accordance with some embodiments.

The above needs can be addressed using the sensing platform shown in FIG. 14 in accordance with some embodiments. The sensing platform may be configured to perform immunoassays as described elsewhere herein.

Referring to FIG. 14, a sensing platform 1400 may include a test strip 1410 and a diagnostic reader device 1420. The test strip may include a sensing device or sensing array. For example, the sensing array 400 shown in FIG. 4 may be provided on the test strip. In some cases, the test strip is composed of a material comprising a plurality of capillary beds such that, when contacted with a sample fluid, the sample fluid is transported laterally across the test strip. The sample fluid may be flowed along a flow path of the test strip from a proximal end to the distal end of the test strip. The sample is flowed by capillarity or wicking. Non-limiting examples of test strips may include porous paper, or a membrane polymer such as nitrocellulose, polyvinylidene fluoride, nylon, Fusion 5™, or polyethersulfone.

The test strip 1410 may also include a wicking pad 1412. The wicking pad may be composed of, e.g., filter paper. Other optional features may include a cover for supporting and/or protecting the test strip. The cover may be composed of a sturdy material such as plastic (e.g., high-impact polystyrene). The cover may, e.g., may protect from inadvertent splashing of a sample onto the test strip (e.g., when the device is applied to a urine stream), and to protect the sensitive areas of the test strip (e.g., the sensing array). The cover may include various openings or windows along the test strip. For example, the cover may include a sample application zone 1414 for applying the fluid sample 152 to the wicking pad 1412.

The test strip may comprise a zone and/or region for conducting an immunoassay. The test strip may define a flow path. The zone and/or region for conducting immunoassays in accordance with the disclosure may be positioned along a flow path of the test strip such that a fluid sample may be flowed (e.g., by capillarity) from the sample application zone 1414 on a proximal end of the strip to a test zone 150 of the sensing array 400. In some alternative embodiments, instead of transporting the sample via capillary flow, the fluid sample 150 may be dispensed (e.g. by pipetting) directly onto the test zone 150.

A test strip may comprise sensing array that are functionalized to detect analytes of interest. Test strips comprising different types of sensing arrays can be provided. The sensing arrays may have different sensing electrode materials (e.g. semiconducting materials), linker chemistries, and capture reagents for binding with a variety of different target analytes, depending on the desired sensing/biosensing application and end physiological state to be predicted.

The diagnostic reader device 1420 can be configured for use with the test strip. The reader device can be a hand-held electronic device. The reader device can be configured to receive the test strip. For example, the test strip can be inserted into a receiving port or chamber of the reader device, thereby establishing electrical connection with the reader device. The reader device may comprise, for example the multiplexer 150, sensing circuitry 160, and/or computing device 170 shown in FIG. 5. The reader device can be configured to perform electro-analytical diagnostics on the test strip substantially in real-time. The electro-analytical diagnostics may include collecting and analyzing the electrochemical signal responses as described elsewhere herein.

In the example of FIG. 14, the test strip is shown inserted into the receiving chamber of the reader device. The reader device can generate measurement results (e.g., concentration or relative amounts of analytes present in the sample) from a completed assay performed on the test strip, as described throughout. The reader device can display the measurement results on a screen 1422 of the reader device. In some embodiments, data containing the measurement results can be transmitted from the reader device to a mobile device 1440 and/or to a server. The data may be transmitted via one or more wireless or wired communication channels. The wireless communication channels may comprise Bluetooth®, WiFi, 3G, and/or 4G networks.

In some embodiments, the data containing the measurement results may be stored in a memory on the reader device when the reader device is not in operable communication with the mobile device and/or the server. The data may be transmitted from the reader device to the mobile device and/or the server when operable communication between the reader device and the mobile device and/or the server is re-established.

A network 1460 can be configured to provide communication between the various components of the embodiments described herein. The network may be implemented, in some embodiments, as one or more networks that connect devices and/or components in the network layout for allowing communication between them. For example, one or more diagnostic test devices, mobile devices and/or servers may be in operable communication with one another over a network. Direct communications may be provided between two or more of the above components. The direct communications may occur without requiring any intermediary device or network. Indirect communications may be provided between two or more of the above components. The indirect communications may occur with aid of one or more intermediary device or network. For instance, indirect communications may utilize a telecommunications network. Indirect communications may be performed with aid of one or more router, communication tower, satellite, or any other intermediary device or network. Examples of types of communications may include, but are not limited to: communications via the Internet, Local Area Networks (LANs), Wide Area Networks (WANs), Bluetooth®, Near Field Communication (NFC) technologies, networks based on mobile data protocols such as General Packet Radio Services (GPRS), GSM, Enhanced Data GSM Environment (EDGE), 3G, 4G, or Long Term Evolution (LTE) protocols, Infra-Red (IR) communication technologies, and/or Wi-Fi, and may be wireless, wired, or a combination thereof. In some embodiments, the network may be implemented using cell and/or pager networks, satellite, licensed radio, or a combination of licensed and unlicensed radio. The network may be wireless, wired, or a combination thereof.

One or more reader devices, mobile devices and/or servers may be connected or interconnected to one or more databases 1450. The databases may be one or more memory devices configured to store data. Additionally, the databases may also, in some embodiments, be implemented as a computer system with a storage device. In one aspect, the databases may be used by components of the network layout to perform one or more operations consistent with the disclosed embodiments. In some embodiments, the databases 1450 may include patient databases.

In some embodiments, one or more graphical user interfaces (GUIs) 1422 may be provided on the reader device 1420. Additionally or optionally, the GUIs may be provided on the mobile device 1440. The GUIs may be rendered on a display screen. A GUI is a type of interface that allows users to interact with electronic devices through graphical icons and visual indicators such as secondary notation, as opposed to text-based interfaces, typed command labels or text navigation. The actions in a GUI are usually performed through direct manipulation of the graphical elements. In addition to computers, GUIs can be found in hand-held devices such as MP3 players, portable media players, gaming devices and smaller household, office and industry equipment. The GUIs may be provided in a software, a software application, a web browser, etc. The GUIs may be provided through a mobile application. The GUIs may be rendered through an application (e.g., via an application programming interface (API) executed on the mobile device). The GUIs may show images that permit a user to monitor levels of analytes of interest.

As depicted in FIG. 14, the sensing platform may further comprise means for transmitting data generated by the reader device and sensing array. In some cases, the data may be transmitted to and/or read from a mobile device (e.g., a cell phone, a tablet), a computer, a cloud application or any combination thereof. The data may be transmitted by any means for transmitting data, including, but not limited to, downloading the data from the system (e.g., USB, RS-232 serial, or other industry standard communications protocol) and wireless transmission (e.g., Bluetooth®, ANT+, NFC, or other similar industry standard). The information may be displayed as a report 1430. The report may be displayed on the screen 1422 of the reader device 1420 or a computer. The report may be transmitted to a healthcare provider or a caregiver. In some instances, the data may be downloaded to an electronic health record. Optionally, the data may comprise or be part of an electronic health record. For example, the data may be uploaded to an electronic health record of a user of the devices and methods described herein. In some cases, the data may be transmitted to a mobile device and displayed for a user on a mobile application.

Data collected by and transmitted by the reader device may include results of the immunoassay test performed on the test strip. For example, the data may include the concentrations of different analytes present in a sample. The concentrations may include relative concentrations or absolute concentrations. For example, the GUI 1422 in FIG. 14 shows the levels of different markers such as PCT, CRP, IL-6, and LBP. The data may also include an outcome such as a diagnostic outcome or a prognostic outcome. The data may also include alerts to the user (e.g. critical, alert, safe). In some cases, the alerts may be color-coded to generate awareness to the user.

Additional data that may be transmitted by the reader device include, without limitation, patient information/details, test settings, device metrics, device setup, time and date of the immunoassay tests, system status (testing temperature, battery status, system self-testing and calibration results), error codes or error messages, etc.

Current handheld POC devices typically offer detection of a single biomarker on a single parameter test strip or cartridge. In contrast, the sensing platform 1400, particularly the sensing array 400 with multiplexer 150 and sensing circuitry 160, can provide simultaneous detection of multiple biomarkers for rapid diagnostic and prognostic on a single electrochemical test strip. The simultaneous and multiplexed detection of multiple biomarkers on a single electrochemical test strip obviates the need to use multiple discrete test strips for detecting different biomarkers.

Additionally, the sensing platform 1400 is capable of analyzing multiple biomarkers using very small volumes (e.g. ≤30 µL) of the fluid sample (e.g. finger-pricked blood) performed substantially in real-time at the patient's bedside.

The sensing platform can lower health care costs through reduced cost of the disposable test strip for multiple biomarker detection, and providing diagnostic and prognostic analysis at the patient bedside in non-clinical environments thus generating savings on physician costs and hospitalization costs. The data analyzed can be securely transmitted to a secure cloud server for the primary physician managing the patient to be able to access, review, and manage guidance and therapies. In the example of FIG. 14, the sensing platform can aid in assessing congestive heart failure (CHF) risk based on the measured levels of the different markers, and is therefore of immediate benefit to primary care and ED physicians. Furthermore, rapid availability of the immunoassay testing can facilitate a rule-out protocol in a busy emergency department.

An example of a POC application using the sensing platform 1400 is next described. A disposable sensing array comprising of IL/ZnO hybrid liquid/solid semiconducting electrode, is functionalized with antibodies that are receptors for the panel of protein biomarkers to be tested. A test sample comprising of ≤20 µL (1-2 drops) blood serum, blood plasma can be dispensed onto the sensor electrodes through standard capillary wicking methods common to lateral flow immunoassays, which yields immunoassay formation at the RTIL/ZnO-buffer interface. The sensing array can be connected to sensing circuitry in the reader device. The sensing circuitry may include a potentiostat, and the reader device may be a hand-held electronic device. After an incubation period sufficient for diffusion limited processes, the sensing circuitry in the reader device measures the impedance over a range of frequencies in the electrochemical window of the RTIL. Based on reference sigmodial calibration, the concentration of a panel of protein biomolecules (e.g., cTn, NT-proBNP, and CRP) can be determined and displayed on the reader device. The sensing platform 1400 is capable of ultrasensitive detection of Troponin and NT-proBNP cardiac markers with high specificity and minimal cross-reactivity in human serum samples. The protein binding and detection process for Troponin and NT-proBNP can be achieved by using a single capture immunoassay (e.g., primary monoclonal antibody-antigen interaction) without the use of any secondary antibody.

In another embodiment, the sensing platform 1400 can be used in aptasensing for K+ detection. Aptamer oligonucleotides that contain single or multiple guanine-rich segments are known to form specific four-stranded helical conformations in solution with an extraordinary selectivity for potassium. In the absence of potassium, the aptamer containing multiple guanine-rich segments adopts a random-coil structure that upon exposure to potassium ion (K+) solution displaces the equilibrium in favor of the G-quadruplex form, the G-quadruplex being a conformation of guanine-rich DNA resulting from the association of sets of four guanine residues into planar arrays. The sensing platform 1400 is capable of higher sensitivity and specificity in the detection of aptamers, as compared to the use of standard ion-selective electrodes for electrolyte sensing.

Accordingly, the sensing platform 1400 can be used for affinity-based impedimetric sensing of troponin (cTnI, cTnT) and NT-proBNP using specific antibodies and affinity based amperometric sensing of K+ and other similar ions using specific aptamers from human blood. As previously described, the human blood can be transported by capillary action on the test strip to the test zone. The test strip can be inserted into the reader device to provide rapid diagnostic and therapeutic response to a physician at the patient's bedside. The sensing platform 1400 can be used for near-patient cardiovascular diagnosis and assessment in primary care, EDs, assisted/independent living care, and ambulatory environments, towards real-time detection and monitoring levels of a panel of cardiac biomarkers (cTnI, NT-proBNP) and sodium, potassium, calcium levels from finger-pricked capillary blood.

B. Wearable Device

Figure 15:
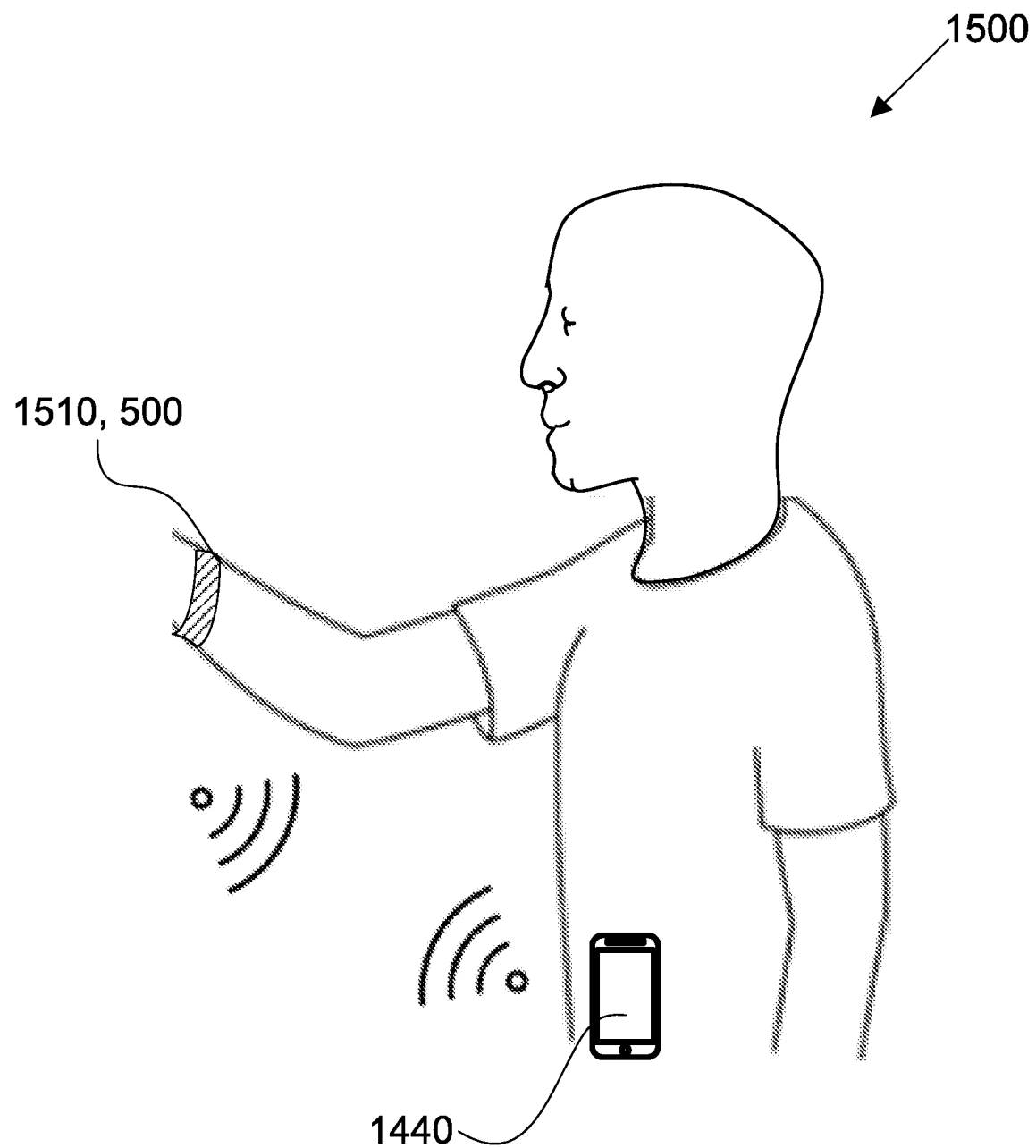
FIG. 15 shows a sensing platform comprising a wearable device in accordance with some embodiments.

In some embodiments, the sensing devices and arrays described herein may be provided on a wearable sensing platform 1500 as shown in FIG. 15. For example, the sensing system 500 shown in FIG. 5 may be provided on a wearable device 1510. Examples of wearable devices may include smartwatches, wristbands, glasses, gloves, headgear (such as hats, helmets, virtual reality headsets, augmented reality headsets, head-mounted devices (HMD), headbands), pendants, armbands, leg bands, shoes, vests, motion sensing devices, etc. The wearable device may be configured to be worn on a part of a user's body (e.g., a smartwatch or wristband may be worn on the user's wrist). The wearable device may include one or more types of sensors. Examples of types of sensors may include heart rate monitors, external temperature sensors, skin temperature sensors, capacitive touch sensors, sensors configured to detect a galvanic skin response (GSR), and the like.

In some embodiments, the sensing system on the wearable device can be capable of transdermally monitoring alcohol content. For example, the sensing system can be configured to monitor blood alcohol levels in real time from ambient perspired sweat. A wearable device (e.g. in the form of a bracelet) can unobtrusively house the sensing systems described herein for simultaneous monitoring of Ethanol and paired Ethyl glucuronide (EtG), Ethyl Sulfate (EtS), Phosphatidylethanol (PEth) levels from ambient perspired sweat. The wearable device can be capable of transdermal measurement of blood alcohol content by detecting and quantifying ethanol paired with simultaneous detection of non-volatile metabolites EtG, EtS, PEth, etc. from ambient perspired sweat. This multi-parameter information can be transmitted via wireless data transmission from the wearable device to portable, hand-held devices such as a smart phone. EtG and EtS are stable, non-oxidative metabolites of alcohol and can be detected in body fluids including sweat. Simultaneous detection of Ethanol and paired EtG, EtS in perspired sweat using unobtrusive and comfortable wearable devices can offer the potential to dramatically improve the ability to accurately assess the responses to treatments, and build longer term behavioral patterns of the individual which is of significant value for research and clinical purposes.

The wearable sensing platform can provide enhanced ability for users and health professionals to collect consumption and exposure assessment data in a variety of scenarios, leading to a greater understanding of the relationship between personal alcohol consumption and exposures and to user physiology, psychology, and disease origins. This can be advantageous in providing assessments for susceptible and at-risk groups, such as young adults, recovering addicts, and people with existing chronic diseases. The wearable sensing platform can be configured to differentiate results for varying alcohol consumption in varying social settings, while collecting data from individuals at the point of exposure. In some cases, wearable sensing platform can also account for individual mobility/variability as people move though different, possibly spatially heterogeneous environments (e.g. via GPS triangulation).

Enzyme-based ethanol sensing technologies are generally based on monitoring of NADH in the case of ADH based sensing devices and $O_2$ consumption or $H_2O_2$ production in the case of alcohol oxidase (AOX) sensing devices. Alcohol dehydrogenase (ADH; Alcohol:NAD$^+$ oxidoreductase, EC 1.1.1.1) catalyzes the reversible oxidation of primary aliphatic and aromatic alcohols other than methanol. Alcohol oxidase (AOX; Alcohol:$O_2$ oxidoreductase, EC 1.1.3.13) catalyzes the conversion of alcohols into corresponding aldehydes or ketones, but not the reverse reaction similar to that catalyzed by the ADH (Scheme 1a). AOX requires flavin-based cofactors, while ADH requires NAD-based cofactors. The FAD in AOX is avidly associated with the redox center of the enzyme and is involved in transferring the hydride ion originated from alcohol substrate to molecular oxygen leading to the formation of $H_2O_2$. The oxidation of alcohols by AOX is irreversible, due to the strong oxidizing character of $O_2$. The NAD$^+$ (or NADP$^+$) involved in ADH catalysis is a strong oxidizing agent that accepts the hydride ion directly from the substrate during the catalysis and generating the corresponding reduced form, NADH/NADPH.

In some embodiments, the sensing system on the wearable device 1510 is configured for catalytic sensing using amperometric methods, which can be used to detect the presence of alcohol in perspired human sweat through either of the above described mechanisms. The ADH or AOX enzyme would be bound to the sensing electrode surface through the linker chemistry, and NAD$^+$ or FAD$^+$ co factor would be applied to the sensing electrode surface. The electrochemical reaction being endothermic (negative $\Delta G$) will primarily proceed in the presence of the catalyst and under an applied potential. Thus when alcohol is present in the solution, the reaction with NAD$^+$ or FAD$^+$ takes place at the sensing electrode surface where the catalyst ADH or AOX is respectively bound and the resulting electrons transfer is measured and used to quantify in real-time the amount of alcohol present in the solution.

In some embodiments, the sensing system on the wearable device 1510 is configured for EtG detection in pooled human sweat using affinity based sensing of bound specific antibodies to Au and ZnO surfaces using the linker chemistry and with the modified EIS technique described elsewhere herein.

The sensing system can employ affinity based impedimetric sensing of EtG and EtS, and PEth using specific antibodies and catalytic enzymatic based amperometric sensing of alcohol with affinity bound enzymes on a multi-configurable electrochemical sensing platform with human sweat sample. This can be used to monitor personal alcohol consumption and abstinence, and can also be used to establish behavioral patterns in social settings.

Figure 16:
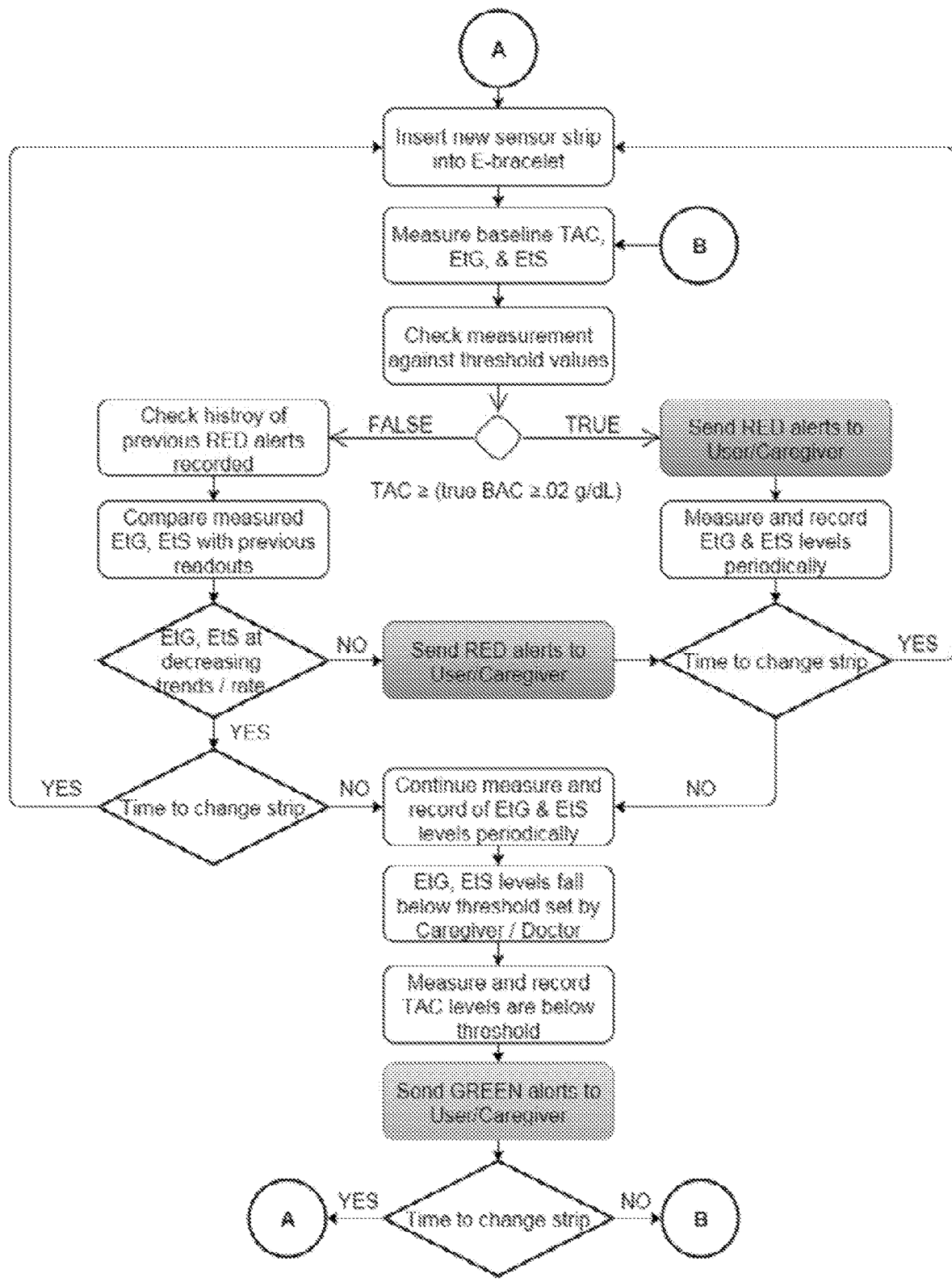
FIG. 16 is a flowchart showing a method for continuous, real-time detection of alcohol, EtG, and EtS in accordance with some embodiments.

FIG. 16 is a flowchart showing a method for continuous, real-time detection of alcohol, EtG, and EtS in accordance with some embodiments. A wearable device (e.g. an e-bracelet) can be configured to receive and perform an immunoassay on a test strip. A test strip containing bodily fluids may be inserted into the wearable device, and the total alcohol content (TAC), EtG, and EtS are measured. Next, the measurements are compared against threshold values. If the TAC is greater than or equal to the threshold values, a negative alert may be sent to the user and/or to a caregiver, while the wearable device continues to measure and record the EtG and EtS levels periodically. Conversely, if the TAC is less than the threshold values, the history of previously recorded negative alerts may be analyzed. The current measured EtG and EtS levels may be compared with previous readouts, to determine if there is an increasing or decreasing trend/rate. If there is an increasing trend/rate in the measured EtG and EtS levels, a negative alert may be sent to the user/caregiver. If there is a decreasing trend/rate in the measured EtG and EtS levels, the wearable device may continue to measure and record the EtG and EtS levels periodically. When the measured EtG and EtS levels falls below predefined values set by the user/caregiver, the TAC may be measured to confirm that TAC levels are below the threshold values, and a positive alert may be subsequently sent to the user/caregiver. In some embodiments, the method may include various steps at which the user is notified by the wearable device whether the test strip needs to be changed. A person of ordinary skill in the art will recognize many variations, alterations and adaptations based on the disclosure provided herein. For example, additional steps may be added as appropriate. Some of the steps may comprise sub-steps. Some of the steps may be automated (e.g., autonomous sensing), whereas some of the steps may be manual (e.g., requiring manual handling, input or responses from a user). The systems and methods described herein may comprise one or more instructions to perform at least one or more steps of method 1500.

V. Multi-Configurable Modular Sensing Device/Array

Various modifications can be made to the sensing devices or arrays described elsewhere herein. In some cases, the sensing devices or arrays can be modular in nature and customized for different sensing applications. For example, a substrate can be modified to receive and interchange thereon a plurality of discrete sensors. The plurality of discrete sensors may comprise different capture reagents that are configured to selectively bind to different target analytes in a fluid sample. Providing a practically unlimited diversity of discrete sensors can result in better health monitoring and outcomes for users, for a variety of biological and chemical sensing applications.

FIGS. 18A-C show an example of a modular sensing device 1800 in accordance with some embodiments. The device 1800 can be configured to detect one or more targets in a fluid sample. The device may include a base module 1810. The base module 1810 may be similar to the substrate (e.g. 110) described elsewhere herein except the base module comprises a receiving portion 1812. The receiving portion may include a recess, cavity, or slot. The base module can be configured to releasably couple to one or more discrete sensors 1820 via the receiving portion 1812. The discrete sensor(s) are configured to be mechanically and electrically coupled to the base module. The discrete sensor(s) can be used to determine a presence and concentration of one or more target analytes in a fluid sample based on detected changes to electron and ion mobility and charge accumulation when the discrete sensor(s) are coupled to the base module and the fluid sample is applied to the sensing device.

The base module 1810 may include a plurality of electrodes. For example, the base module may include at least one reference electrode (e.g. 140) and at least one ground electrode (e.g. 130). In some embodiments, the receiving portion 1812 may be located in a region between a ground electrode 130 and a reference electrode 140.

FIG. 18B shows a plurality of discrete sensors 1820-1 through 1820-*n* that can be interchangeably coupled to the base module of FIG. 18A. The plurality of discrete sensors can be configured to be interchanged and/or mounted onto the base module using a quick release mechanism and/or without the use of tools. FIG. 18C shows an example of a first discrete sensor 1820-1 being coupled to the base module 1810 via the receiving portion 1812.

Referring to FIG. 18B, each of the discrete sensors 1820 may comprise a working electrode 120 having a plurality of semiconducting nanostructures 122 disposed thereon, and a capture reagent 124 attached to the semiconducting nanostructures. The discrete sensors may include the same or different types of semiconducting nanostructures. The discrete sensors may comprise different capture reagents (124-1 through 124-*n*) that are configured to selectively bind to different target analytes in a fluid sample. The selective binding is configured to effect changes to the electron and ion mobility and charge accumulation in different regions of the semiconducting nanostructures and the fluid sample. The plurality of discrete sensors can be used for determining the presence and concentration of the different target analytes in the fluid sample, as described in many embodiments elsewhere herein.

In some embodiments, a first discrete sensor may be releasably coupled to the base module thereby electrically and mechanically connecting the first discrete sensor to the base module. Next, a fluid sample suspected to contain a first target analyte may be applied to the modular sensing device. The first discrete sensor can be used to determine a presence and concentration of the first target analyte in the fluid sample based on detected changes to electron and ion mobility and charge accumulation specific to the first target analyte. The first discrete sensor may be detached from the base module after the presence and concentration of the first target analyte has been determined.

Next, a second discrete sensor may be releasably coupled to the base module thereby electrically and mechanically connecting the second discrete sensor to the base module. Another fluid sample suspected to contain a second target analyte may be applied to the modular sensing device. The second discrete sensor can be used to determine a presence and concentration of the second target analyte in the fluid sample based on detected changes to the electron and ion mobility and charge accumulation specific to the second target analyte.

Figure 19A:
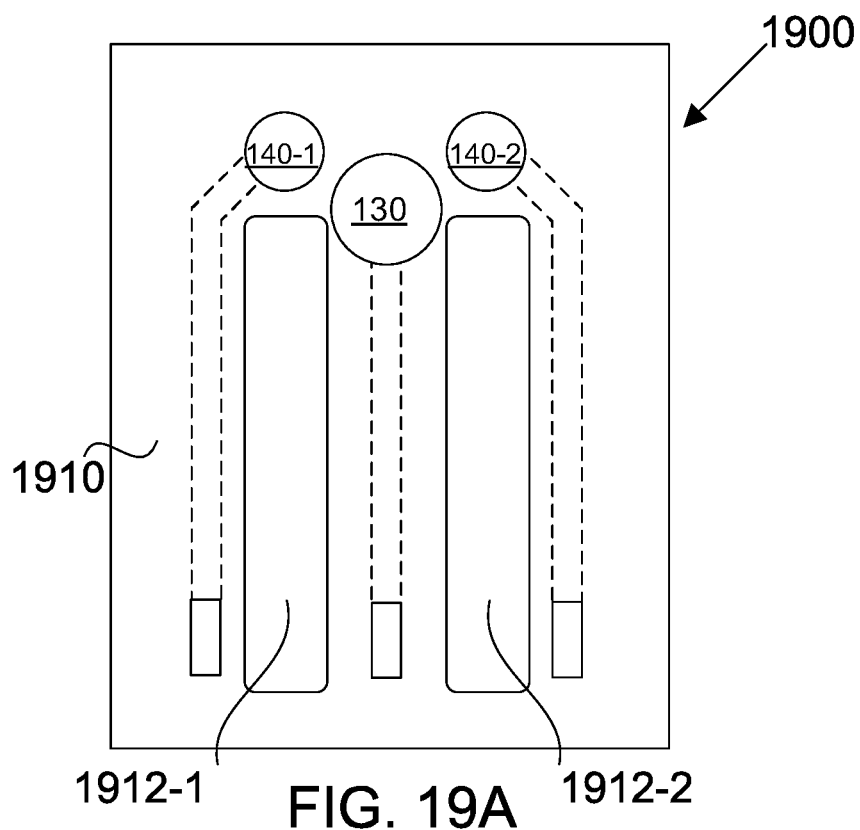
FIGS. 19A and 19B show a multi-configurable modular sensing array in accordance with some embodiments.
Figure 19B:
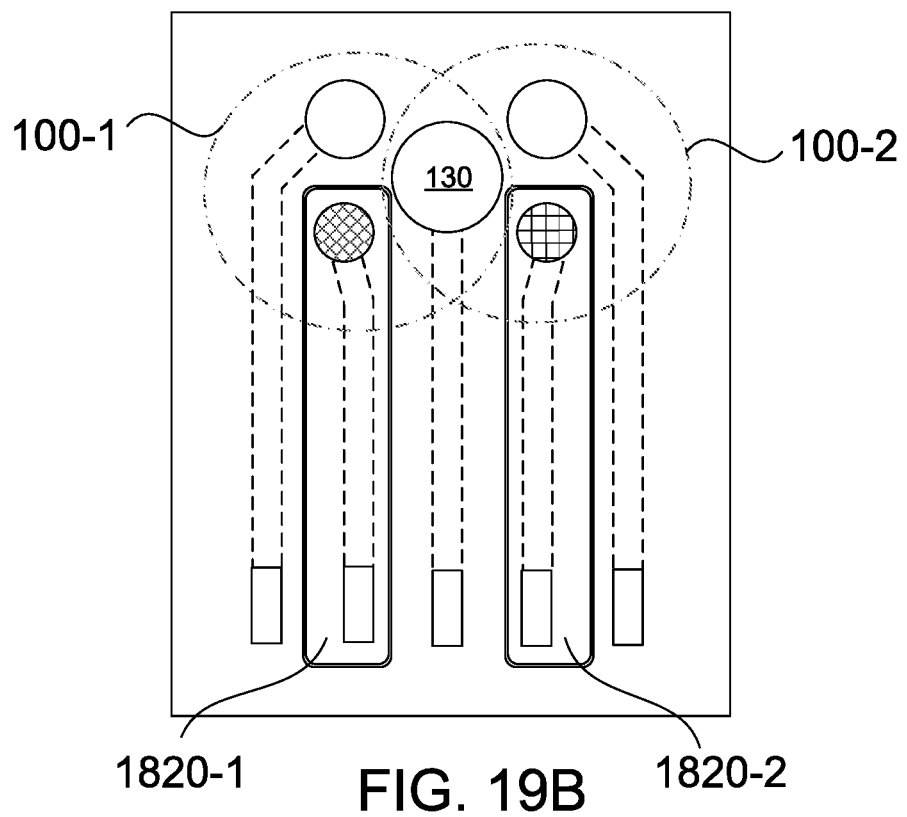

The modular sensing device of FIGS. 18A-C may be modified into a modular sensing array for example as shown in FIGS. 19A and 19B. A modular sensing array 1900 can be configured for simultaneous and multiplexed detection of two or more target analytes in a fluid sample. The array may include a base module 1910 configured to releasably couple to two or more discrete sensors. In the example of FIGS. 19A-C, the base module may comprise (1) a first receiving portion 1912-1 configured to couple to a first discrete sensor 1820-1, and (2) a second receiving portion 1912-2 configured to couple to a second discrete sensor 1820-2. The discrete sensors 1810-1 and 1810-2 are configured to be mechanically and electrically coupled to the base module. Each of the discrete sensors may comprise a working electrode 120 having a plurality of semiconducting nanostructures 122 disposed thereon, and a capture reagent 124 attached to the semiconducting nanostructures. The plurality of discrete sensors comprises different capture reagents that are configured to selectively bind to different target analytes in a fluid sample. The selective binding is configured to effect changes to the electron and ion mobility and charge accumulation in different regions of the semiconducting nanostructures and the fluid sample. The discrete sensors can be used to determine a presence and concentration of at least two different target analytes in the fluid sample based on detected changes to electron and ion mobility and charge accumulation when the discrete sensors are coupled to the base module and the fluid sample is applied to the sensing array.

The base module may comprise at least one reference electrode and at least one counter electrode. For example, the base module may comprise counter electrodes 140-1 and 140-2, and a common reference electrode 130. A first sensing device 1800-1 can be formed by coupling the first discrete sensor 1820-1 to the first receiving portion 1812-1. The first sensing device 1800-1 may comprise the first counter electrode 140-1, the working electrode 120-1, and the reference electrode 130. A second sensing device 1800-2 can be formed by coupling the second discrete sensor 1820-2 to the second receiving portion 1812-2. The second sensing device 1800-2 may comprise the second counter electrode 140-2, the working electrode 120-2, and the reference electrode 130. Accordingly, the first and second sensing devices 1800-1 and 1800-2 may share a common reference electrode. The first sensing device 1800-1 can be configured to determine the presence and concentration of a first target analyte, and the second sensing device 1800-2 can be configured to determine the presence and concentration of a second target analyte, similar to the embodiments described elsewhere herein.

In some embodiments, a method of using a modular sensing array for detecting one or more target analytes in a fluid sample may include providing a base module configured to releasably couple to one or more discrete sensors. The method may also include coupling the one or more discrete sensors to the base module thereby electrically and mechanically connecting said discrete sensors to the base module. The method may further include applying the fluid sample to the modular sensing array, and using the one or more discrete sensors to determine a presence and concentration of the one or more target analytes in the fluid sample based on detected changes to electron and ion mobility and charge accumulation specific to each of the one or more target analytes.

In some embodiments, the above method may include coupling a first discrete sensor and a second discrete sensor to the base module thereby electrically and mechanically connecting the first and second discrete sensors to the base module. A fluid sample suspected to contain a first target analyte and a second target analyte may be applied to the modular sensing array. The first discrete sensor can be to determine a presence and concentration of the first target analyte in the fluid sample based on detected changes to electron and ion mobility and charge accumulation specific to the first target analyte. Similarly, the second discrete sensor can be used to determine a presence and concentration of the second target analyte in the fluid sample based on detected changes to the electron and ion mobility and charge accumulation specific to the second target analyte.

VII. Kits

Further provided herein are kits which may include any number of immunoassay test devices and/or reader devices of the disclosure. In one aspect, a kit is provided for determining qualitatively or quantitatively the presence and concentration of at least a first analyte and a second analyte in a fluid sample, the kit comprising: a) a sensing device or array according to one or more embodiments of the disclosure; and b) instructions for using the kit.

In some cases, a kit may provide a sensing device or array to enable a user to conduct a test on more than one occasion. In some cases, a kit may include a plurality of test strips each configured for a single use (i.e., are disposable). A kit may include a plurality of test devices to enable a user to perform a test once a day, once every 2 days, once every 3 days, once every 4 days, once every 5 days, once every 6 days, once every week, once every 2 weeks, once every 3 weeks, once every 4 weeks, once every 5 weeks, once every 6 weeks once every 7 weeks, once every 8 weeks or more.

In some cases, kits may include a plurality of immunoassay test devices, each capable of detecting different analytes. In some embodiments, kits may include a plurality of discrete sensors for detecting different analytes. In a particular embodiment, a kit may include the sensing array disclosed herein, that is capable of detecting the presence of cTnI and/or cTnT, NT-proBNP, and CRP in a biological sample such as blood. In another particular embodiment, a kit may include a sensing array disclosed herein, that is capable of detecting the presence and concentration of alcohol content, EtG, and EtS in a biological sample such as sweat.

In some cases, kits can be provided with instructions. The instructions can be provided in the kit or they can be accessed electronically (e.g., on the World Wide Web). The instructions can provide information on how to use the devices and/or systems of the present disclosure. The instructions can provide information on how to perform the methods of the disclosure. In some cases, the kit can be purchased by a physician or health care provider for administration at a clinic or hospital. In other cases, the kit can be purchased by the subject and self-administered (e.g., at home). In some cases, the kit can be purchased by a laboratory.

Kits may further comprise a diagnostic reader device or wearable device of the disclosure. The diagnostic reader device or wearable device may be configured to be used with the sensing devices or arrays of the disclosure. The diagnostic reader device or wearable device may be configured to be in operable communication with the sensing devices or arrays.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus comprising:
  an array of a plurality of sensing devices provided on a substrate, wherein each sensing device in the array is configured to detect a respective one of a plurality of different target analytes, and each sensing device in the array comprises:
  a respective working electrode with semiconducting nanostructures disposed thereon;
  a capture reagent coupled to the semiconducting nanostructures to selectively bind to the respective one of the plurality of different target analytes in a sample; and
  a respective counter electrode,
  wherein:
    a pair of sensing devices in the plurality of sensing devices comprises a shared reference electrode,
    the shared reference electrode is a single reference electrode shared between the pair of sensing devices as a single common reference electrode for the pair of sensing devices,
    the single common reference electrode is proximate to and located between each respective working electrode of the pair of sensing devices and between each respective counter electrode of the pair of sensing devices, the semiconducting nanostructures are only disposed on each respective working electrode of the plurality of sensing devices and omitted from each respective counter electrode of the plurality of sensing devices and the shared reference electrode of the pair of sensing devices, the pair of sensing devices comprise a first sensing device and a second sensing device, the respective working electrode and the respective counter electrode of the first sensing device are located in proximity to each other in a first region of the substrate, and the respective working electrode and the respective counter electrode of the second sensing device are located in proximity to each other in a second region of the substrate, and the single common reference electrode is located between the respective working electrode and the respective counter electrode of the first sensing device and the respective working electrode and the respective counter electrode of the second sensing device.

2. The apparatus of claim 1, further comprising sensing circuitry to determine both presence and concentration of each of the plurality of different target analytes from the array of the plurality of sensing devices.

3. The apparatus of claim 2, wherein the sensing circuitry is to simultaneously detect changes to electron and ion mobility and charge accumulation in the array of the plurality of sensing devices when the capture reagent in the array of the plurality of sensing devices selectively binds to corresponding target analyte.

4. The apparatus of claim 2, wherein the apparatus is to detect any one of the plurality of different target analytes present in the sample using the array of the plurality of sensing devices and the sensing circuitry.

5. The apparatus of claim 4, wherein the array of the plurality of sensing devices comprises sensing devices with different capture reagents to selectively bind to different analytes in the plurality of different target analytes.

6. The apparatus of claim 4, wherein the apparatus is configured to detect the plurality of different target analytes in the sample, wherein the sample has a volume of less than 30 μL.

7. The apparatus of claim 1, wherein the single common reference electrode, each respective working electrode of the pair of sensing devices, and each respective counter electrode of the pair of sensing devices are each circular in shape.

8. The apparatus of claim 1, wherein the first sensing device comprises a first capture reagent that selectively binds to a first target analyte in the sample, and the second sensing device comprises a second capture reagent that selectively binds to a second target analyte in the sample.

9. The apparatus of claim 8, wherein the first and second target analytes are different biomarkers.

10. The apparatus of claim 8, wherein the first and second target analytes are different isoforms of a same type of biomarker.

11. The apparatus of claim 1, wherein two or more of the plurality of sensing devices in the array comprise working electrodes having a same type of semiconducting nanostructures.

12. The apparatus of claim 1, wherein two or more of the plurality of sensing devices in the array comprise working electrodes having different types of semiconducting nanostructures.

13. The apparatus of claim 1, wherein the sample comprises at least one of sweat, blood, serum, or urine of a human subject.

14. The apparatus of claim 1, wherein the apparatus further comprises a sensing circuitry configured for:
collecting electrical signals from the array of the plurality of sensing devices;
simultaneously detecting changes to electron and ion mobility and charge accumulation from the collected electrical signals, wherein the electronic and ion mobility and the charge accumulation change when the capture reagent selectively binds to the respective one in the plurality of different target analytes in the sample; and
determining, based on the detected changes, a presence of the respective one in the plurality of different target analytes in the sample.

15. The apparatus of claim 14, wherein the sensing circuitry is further configured for detecting, based on the detected changes, a concentration of the respective one in the plurality of different target analytes in the sample.

16. The apparatus of claim 1, wherein the capture reagent is immobilized on a surface of the respective working electrode.

17. The apparatus of claim 1, wherein the substrate comprises flexible printed circuit board (PCB) materials.

18. The apparatus of claim 1, wherein:
the substrate comprises a flexible and porous polyimide material.

19. The apparatus of claim 1, wherein the substrate comprises at least one of: porous paper, nitrocellulose, polyvinylidene fluoride, nylon, and polyethersulfone.

20. The apparatus of claim 1, wherein the substrate comprises at least one material selected from: silicon, glass, polyurethane, polycarbonate, polyamide, and polyimide.

* * * * *